(12) United States Patent
Cohen

(10) Patent No.: US 8,512,961 B2
(45) Date of Patent: Aug. 20, 2013

(54) **METHODS OF DETECTING AND TREATMENT OF CANCERS USING *SCUTELLARIA BARBATA* EXTRACT**

(75) Inventor: Isaac Cohen, Piedmont, CA (US)

(73) Assignee: Bionovo, Inc., Emeryville, CA (US)

( * ) Notice: Subject to any disclaimer, the term of this patent is extended or adjusted under 35 U.S.C. 154(b) by 504 days.

(21) Appl. No.: 12/274,215

(22) Filed: Nov. 19, 2008

(65) Prior Publication Data

US 2009/0130684 A1    May 21, 2009

Related U.S. Application Data

(60) Provisional application No. 60/989,065, filed on Nov. 19, 2007.

(51) Int. Cl.
*G01N 33/53* (2006.01)
*A61K 36/00* (2006.01)

(52) U.S. Cl.
USPC ............................................ 435/7.1; 424/725

(58) Field of Classification Search
None
See application file for complete search history.

(56) References Cited

U.S. PATENT DOCUMENTS

| | | | |
|---|---|---|---|
| 5,032,580 A | 7/1991 | Wantanabe et al. | |
| 5,164,182 A | 11/1992 | Meybeck et al. | |
| 5,650,433 A | 7/1997 | Wantanabe et al. | |
| 5,874,084 A | 2/1999 | Yng-Wong | |
| 6,238,707 B1 | 5/2001 | Chun | |
| 6,280,715 B1 | 8/2001 | Seguin et al. | |
| 6,309,825 B1 | 10/2001 | Thomas | |
| 6,348,204 B1 | 2/2002 | Touzan | |
| 6,551,627 B1 | 4/2003 | Yoon et al. | |
| 6,599,540 B1 | 7/2003 | Fabre et al. | |
| 2003/0170292 A1 | 9/2003 | Yong et al. | |
| 2003/0190375 A1 | 10/2003 | Erdelmeier et al. | |
| 2004/0101576 A1 | 5/2004 | Yagi et al. | |
| 2005/0032882 A1 | 2/2005 | Chen | |
| 2005/0118290 A1 | 6/2005 | Yong et al. | |
| 2005/0196409 A1* | 9/2005 | Dao et al. | 424/195.15 |
| 2005/0208070 A1 | 9/2005 | Dao et al. | |
| 2005/0208159 A1 | 9/2005 | Kang et al. | |
| 2005/0267193 A1 | 12/2005 | Zelig | |
| 2006/0100238 A1 | 5/2006 | Kelley et al. | |
| 2006/0134243 A1 | 6/2006 | Cohen | |
| 2006/0134245 A1 | 6/2006 | Cohen | |
| 2006/0166231 A1 | 7/2006 | Baker et al. | |
| 2006/0210657 A1 | 9/2006 | Chou | |
| 2006/0222721 A1 | 10/2006 | Cohen | |
| 2007/0050865 A1 | 3/2007 | Ayabe | |
| 2007/0105133 A1 | 5/2007 | Clarke et al. | |
| 2007/0110832 A1 | 5/2007 | Cohen | |
| 2007/0122492 A1 | 5/2007 | Behr et al. | |
| 2007/0122501 A1 | 5/2007 | Harley et al. | |
| 2007/0203136 A1 | 8/2007 | Lu et al. | |
| 2007/0265318 A1 | 11/2007 | Greenlee et al. | |
| 2008/0069909 A1 | 3/2008 | Olalde | |
| 2008/0319051 A1 | 12/2008 | Cohen | |
| 2009/0041867 A1 | 2/2009 | Cohen | |
| 2009/0042818 A1 | 2/2009 | Cohen | |
| 2009/0068293 A1 | 3/2009 | Cohen | |
| 2009/0068298 A1 | 3/2009 | Cohen | |
| 2009/0068299 A1 | 3/2009 | Cohen | |
| 2009/0258942 A1 | 10/2009 | Cohen | |
| 2009/0304825 A1 | 12/2009 | Cohen | |
| 2009/0311349 A1 | 12/2009 | Cohen | |
| 2009/0312274 A1 | 12/2009 | Cohen | |
| 2009/0312437 A1 | 12/2009 | Cohen | |

FOREIGN PATENT DOCUMENTS

| | | |
|---|---|---|
| CN | 1183297 A | 6/1998 |
| CN | 1294009 A | 5/2001 |
| EP | 0499467 A2 | 9/1992 |
| JP | 2001-122871 | 5/2001 |
| JP | 2002-029980 | 1/2002 |
| JP | 2004-155779 | 6/2004 |
| KR | 10-0221762 B1 | 9/1999 |
| KR | 10-2003-0006736 | 1/2003 |
| KR | 10-2003-0027208 | 4/2003 |
| KR | 10-2006-0057291 | 5/2006 |
| WO | WO-03-016527 A2 | 2/2003 |
| WO | WO-03-040134 A | 5/2003 |
| WO | WO-2004-096020 A2 | 11/2004 |
| WO | WO-2005-044182 A2 | 5/2005 |
| WO | WO-2006-065599 A1 | 6/2006 |
| WO | WO-2006-065608 A2 | 6/2006 |

OTHER PUBLICATIONS

Zips et al. (2005, In Vivo, 19:1-7).*
Wong et al (Cancer Biotherapy and Radiopharmaceuticals, 1996, 11:51-56).*
Albert, A. et al., "Efficacy and safety of phytoestrogen preparation derived from *Glycine max* (L.) Merr in climacteric symptomatology: a multicentric, open, prospective and non-randomized trial," Phytomedicine 9:85-92 (2002).
An, J. et al., "Estrodiol repression of tumor necrosis factor-alpha transcription requires estrogen receptor activation function-2 and is enhanced by coactivators," PNAS USA 96:15161-15166 (1999).
An, J. et al., "Estrgen receptor beta-selective transcriptional activity and recruitment of coregulators by phytoestrogens," J. Biol. Chem. 276:17808-17814 (2001).

(Continued)

*Primary Examiner* — Laura B Goddard
(74) *Attorney, Agent, or Firm* — Wilson, Sonsini, Goodrich & Rosati

(57) ABSTRACT

An extract of *Scutellaria Barbata* D. Don is effective in the arrest of cancer cell growth. The extract of *Scutellaria Barbata* D. Don may be used as a therapeutic treatment for patients who have been identified as having cancer. In some situations, a patient is identified as having a type of cancer by detecting the presence of a biomarker for that cancer in the patient's system and by further determining the level of that biomarker in the patient's system. If the level of the biomarker is above a predetermined threshold level for that biomarker, the patient may be diagnosed with cancer. Subsequently, treatment using an extract of *Scutellaria Barbata* D. Don may begin. Biomarkers of interest in the detection of the presence of metastitic breast cancer include 8-oxoguanine and lactate dehydrogenase.

5 Claims, 9 Drawing Sheets

(56) References Cited

OTHER PUBLICATIONS

Anderson, G.L. et al., Effects of conjugated equine estrogen in postmenopausal women with hysterectomy: the Women's Health Initiative randomized controlled trial, JAMA 291:1701-1712 (2004).

Baek, J. et al., "Effects of Methyl Chloride (MC) Fraction Isolated from *Scutellaria barbata* on Apoptosis of a Human Lymphoma Cell Line (U937) Cells," Blood 100(11):279B, Abstract 4650 (2002).

Barbieri, RL "The initial fertility consultation: Recommendations concerning cigarette smoking, body mass index, and alcohol and caffeine consumption" American Journal of Obstetrics and Gynecology vol. 185, No. 5 (Nov. 2001) 1168-1173.

Barkhem, T. et al., "Differential response of estrogen receptor alpha and estrogen receptor beta to partial estrogen agonists/antagonists," Mol. Pharma. 54:105-112 (1998).

Bensky, D. et al., Chinese Herbal Medicine: Formulas & Strategies (1990), Eastland Press, Inc., Seattle, Washington, pp. 117, 224, 379, 380, 383 and 384.

Bernhardt, et al., "Standardized Kinetic Microassay to Quantify Differential Chemosensitivity on the Basis of Proliferative Activity," J. Cancer Res. Clin Oncol 118:35-43 (1992).

Bjornstrom, L., "Estrogen receptor-dependent activation of AP-1 via non-genomic signalling," Nuclear Receptor 2:3 (2004).

Campbell, M.J. et al., "Antiproliferative Activity of Chinese Medicinal Herbs on Breast Cancer Cells In Vitro," Anticancer Research 22:3843-3852 (2002).

Chlebowski, R.T. et al., "Influence of estrogen plus progestin on breast cancer and mammography in healthy postmenopausal women: the Women's Healt Initiative Randomized Trial, " JAMA 289:3243-3253 (2003).

Chui, C.H. et al., "Anti-cancer potential of traditional Chinese herbal medicines and microbial fermentation products," Minerva Biotech 17:183-191 (2005).

Chui, C.H. et al., "Activities of fresh juice of *Scutellaria barbata* and warmed water extract of Radix Sophorae Tonkinensis on anti-proliferation and apoptosis of human cancer cell lines," Intl J Mol Med 16:337-341 (2005).

Coope J. "Hormonal and non-hormonal interventions for menopausal symptoms" Maturitas, vol. 23 No. 2 (Mar. 1996) 159-168.

Cranney, A. and Adachi, J.D., "Benefit-risk assessment of raloxifene in postmenopausal osteoporosis," Drug Saf. 28:721-730 (2005).

Cvoro, A. et al., "Selective activation of estrogen receptor-beta transcriptional pathways by an herbal extract," Endocrinology 148:538-547 (2007).

Cvoro, A. et al., "Distinct Roles of Unliganded and Liganded Estrogen Receptors in Transcriptional Repression," Mol. Cell 21:555-564 (2006).

Delmas, P. et al., "Effects of raloxifene on bone mineral density, serum cholesterol concentrations, and uterine endometrium in postmenopausal women," N. Eng. J. Med. 337:1641-1647 (1997).

Ducki, S. et al., "Isolation of E-1-(4'-Hydroxyphenyl)-but-1-en-3-one from Scutellaria barbata," Planta Medica 62:185-186 (1996).

Duffy, R. et al., "Improved cognitive function in postmenopausal women after 12 weeks of consumption of a soya extract containing isoflavones," Pharacol. Behavior 75(3):721-729 (2003).

Evans, M.L. et al., "Management of postmenopausal hot flushes with venlafaxine hydrochloride: a randomized, controlled trial," Obstet. Gynecol. 105:161-166 (2005).

Ferrier, R.J. and Blatter, R., "NMR SPectroscopy and Conformational Features, Ch. 21, Carbohydrate Chemistry-Monosaccharides, Disaccharides and Specific Oligosaccharides: A Review," pub. Royal Society of Chemistry, vol. 32:312-314 (2001).

Fingl, et al., In the Pharmacological Basis of Therapeutics (Ed. Goodman & Gilman, MacMillan, NY) Chapter 1, p. 1 (1975).

Fong et al., "Poster Presentation," Proceedings of the American Association for Cancer Research 95th Annual Meeting, 2007 AACR Annual Meeting, Apr. 14-18, 2007, Los Angeles, Abstract 4837.

Fu, B. et al., "Isolation and identification of flavonoids in licorice and a study of their inhibitory effects on tyrosinase," J. Agric. Food Chem. 53:7408-7414 (2005).

Goh, D. et al., "Inhibitory Effects of a Chemically Standardized Extract from *Scutellaria barbata* in Human Colon Cancer Cell Lines, LoVo," J Agric. Food Chem. 53:8197-8204 (2005).

Haber, "Chromatin Immunoprecipitation," Jul. 18, 2005 http://www.bio.brandeis.edu/haberlab.jehsite/protocol.html.

Harris, H.A. et al., "Evaluation of an estrogen receptor-beta agonist in animal models of human disease," Endocrinology 144:4241-4249 (2003).

Hewitt, S.C. et al., "Lessons in estrogen biology from knockout and transgenic animals," Annu. Rev. Physiol. 67:285-308 (2005).

Hsu, H.Y. et al., Oriental Materia Medica: A Concise Guide (1986):Keats Publishing Inc., USA, pp. 119, 120, 144, 145, 272, 273, 524 and 525.

Jordan, V.C., "Selective estrogen receptor modulation: concept and consequences in cancer," Cancer Cell 5:207-213 (2004).

Jordan, V.C., "The ups and downs of the estrogen receptor," J. Clin, Onc. 21:3-4 (2004).

Kim, D. et al., "Regulation of IGF-1 production and proliferation of human leiomyomal smooth muscle cells by *Scutellari barbata* D. Don in vitro: isolation of flavonoids of apigenin and luteolon as acting compounds," Toxicology and Applied Pharmacology 205:213-224 (2005).

Klein, O.K. et al., "Estrogen bioactivity in fo-ti and other herbs used for their estrogen-like effects as determined by a recombinant cell bioassay," J. Clin. Endocrin. Metab. 88:4077-4079 (2003).

Klinge, C.M., "Estrogen receptor interaction with estrogen response elements," Nucleic Acids Res. 29(14):2905-2919 (2001).

Kuiper, G.G. et al., "Interaction of estrogenic chemicals and phyytoestrogens with estrogen receptor beta," Endocrinology 139:4252-4263 (1998).

Kummalue, T., "Molecular Mechanism of Herbs in Human Lung Cancer Cells," J. Med. Assoc.Thai. 88(11):1725-1734 (2005).

Lacroix, M. and Leclercq, G., "Relevance of breast cancer cell lines as models for breast tumors: an update," Breast Cancer Res. Treat. 83:249-289 (2004).

Laganiere, J. et al., "Locational analysis of estrogen receptor alpha target promoters reveals that FOXA1 defines a domain of the estrogen response," PNAS 102(33):11651-11656 (2005).

Lawrence, N.J. et al., "The Chemistry and Biology of Antimitotic Chalcones and Related Enone Systems," Current Pharmaceutical Design 11:1670-1693 (2005).

Lee, T.K. et al., "*Scutellaria barbata* D.Don induces c-fos gene expression in human uterine leiomyomal cells by activating β2-adrenergic receptors," Int. J. Gynecol. Cancer 14:526-531 (2004).

Lee, T.K. et al., "Inhibitory effects of *Scutellaria barbata* D. Don on human uterine leiomyomal smooth muscle cell proliferation through cell cycle analysis," Intl. Immunol. 4:447-454 (2004).

Levy,N. et al., "Multiple Transcription Factor Elements Collaborate with ER(alpha) to Activate an Inducible Estrogen Response Element in the NKG2E gene," Endocrinoloy 148(7):3449-3458 (2007).

Liu, C.W. et al., "Estrogen receptor assays of *Scutellariae barbatae* Herba, Lithospermix Radix and Oldenlandiae Herba," Pharm. Res. 12(Suppl.):s126 (1995).

Loprinzi, C.L., et al., "Venlafaxine in management of hot flashes in survivors of breast cancer: a randomised controlled trial," Lancet 356:2059-2063 (2000).

Loprinzi, L. et al., "Pilot evaluation of gabapentin for treating hot flashes," Mayo Clin. Proc. 77:1159-1163 (2002).

Love, R. et al., "Effects of tamoxifen on bone mineral density in postmenopausal women with breast cancer," N. Engl. J. Med. 326:852-856 (1992).

Lu, H.C., Chinese Herbs with Common Foods:Recipes for Health and Healing (1997), Japan; Kodansha International Inc., pp. 94, 115, 119, and 120.

MacGregor, J.I. and Jordan, V.C., "Basic Guide to the Mechanisms of Antiestrogen Action," Pharmacol. Rev. 50(2):151-196 (1998).

Maggioline, M. et al., "Estrogenic and antiproliferative activities of isoliquiritigenin in MCF7 breast cancer cells," J. Steroid Biochem. Mol. Biol. 82:315-322 (2002).

Manson, J.E. et al., "Estrogen plus progestin and the risk of coronary heart disease," N. Engl. J. Med. 349:523-534 (2003).

Marsh, M.M. et al., "Protection against atherosclerosis by estrogen is independent of plasma cholesterol levels in LDL receptor-deficient mice," J. Lipid Res. 40:893-900 (1999).

McHenry, A.M. et al., "Modulation of apoptosis in LNCaPcells by the Chinese medicinal herb *Scutellaria barbata*," AACR Meeting Abstracts Online, Abstract 721, Proc. Amer. Assoc. Cancer Res. 45 (2004) http://.www.aacrmeetingabstacts.org/cpi/content/abstract/2004/1/167.

Miller, H. et al., "Modulation of estrogen signaling by interaction of heat shock protein 27, a biomarker for atherosclerosis, and estrogen receptor beta: mechanistic insight into the vascular effects of estrogens," Atheroscler. Thromb. Vasc. Biol. 25:10-14 (2005).

Newman, et al., "Natural Products as Sources of New Drugs Over the Period 1981-2002," J. Nat. Prod 66:1022-1037 (2003).

Nilsson, S. and Gustafsson, J.A., "Estrogen receptor transcription and transactivation: basic aspects of estrogen action," Breast Cancer Res. 2:360-366 (2000).

Parmar, H. et al., "A novel method for growing human breast epithelium in vivo using mouse and human mammary fibroblasts," Endocrinology 143:4886-4896 (2002).

Paruthiyil, S. et al., "Estrogen receptor beta inhibits human breast cancer cell proliferation and tumor formation by causing a G2 cell cycle arrest," Cancer Res. 64:423-428 (2004).

Powell, C.B. et al., "Aqueous extract of herba *Scutellaria barbatae*, a chinese herb used for ovarian cancer, induces apoptosis of ovarian cancer cell lines," Gynecologic Oncology 91:332-340 (2003).

Ricke, W.A. et al., "Steroid hormones stimulate human prostate cancer progression and metastasis," Int. J. Cancer 118:2123-2131 (2006).

Rossouw, J.E. et al., "Postmenopausal hormone therapy and risk of cardiovascular disease by age and years since menopause," JAMA 297:1465-1477 (2007).

Rugo, H. et al., "Phase I trial and antitumor effects of BZL101 for patients with advanced breast cancer," Breast Cancer Res Treat 105(1):17-28 (2007) DOI 10.1007/s10549-006-9430-6, Springer Science-Business Media B.V. 2006.

Sato, S. et al., "Total Synthesis of three naturally occuring 6,8-di-C-glycosylflavanoids: phloretin, naringenin, and apigenin bis-C-b-D-glucosides," Carbohydrate Res. 341:964-970 (2006).

Semmar, N. et al., "New flavonol tetraglycosides from *Astragalus caprinus*," Chem. Pharm. Bull. 50(7):981-984 (2002).

Shoemaker, M. et al., "In Vitro Anticancer Activity of Twelve Chinese Medicinal Herbs," Phytotherapy Research 19:649-651 (2005).

Shumaker, S.A. et al., Conjugated equine estrogens and incidence of probable dementia and mild cognitive impairment in postmenopausal women: Women's Health Initiative Memory Study,: JAMA 291:2947-2958 (2004).

Shumaker, S.A. et al., "Estrogen plus progestin and the incidence of dementia and mild cognitive impairment in postmenopausal women: the Women's Health Initiative Memory Study: a randomized controlled trial," JAMA 289:2651-2662 (2003).

Sicat, B.L. and Brokaw, D.K., "Nonhormonal alternatives for the treatment of hot flashes," Pharmacotherapy 24:79-93 (2004).

Simoni, D. et al., Novel combrestatin analogues awith antitumor activity, J. Med. Chem. 49:3143-3152 (2006).

Song, H.Z. et al., "In Vitro Study of the Chemopreventive Effects of Chinese Herbs against Hepatocarcinogenesis," J. Clin. Biochem. Nutri. 35:1-5 (2004).

Strom, A. et al., "Estrogen receptor beta inhibits 17beta-estradiol-stimulated proliferation of the breast cancer cell line. T47D," PNAS USA 101:1566-1571 (2004).

Suthar, A.C. et al., "Pharmacological activities of genistein an isoflavone from soy (*Glycine max*):Part II. Anti-cholesterol activity, effects on osteoporosis & menopausal symptoms," Indian J. Exp. Biol. 39(6):520-525 (2001).

Tagliaferri, M. et al., "A phase I trial of *Scutellaria barbata* (BZL101) for metastatic breast cancer," Abstract 1079, Breast Cancer Research and Treatment 94 ( Suppl. 1 ): p. S66 2005.

Tan, B.K.H. et al., "Traditional Chinese Medicines in Breast Cancer: Clinical and Experimental Data," Abstract 356, Intl J Mol Med 12(Supp 1):S68 (2003).

Tee, M.K., "Estrogen Receptor Modulators Differentially Regulate Target Genes with Estrogen Receptors alpha and beta," Mol. Biol. Cell 15:1262-1272 (2004).

Tzagarakis-Foster, C. et al., "Estradiol represses human T-cell leukemia virus type 1 Tax activation of tumor necrosis factor-alpha gene transcription," J. Biol. Chem. 277:44772-44777 (2002).

Upchurch, D.M. et al., "Complementary and alternative medicine use among American women: findingf from the National Health Interview Survey, 2002, " J. Women Health (Larchmt) 16:102-113 (2007).

Voskoglou-Nomikos et al., "Clinical Predictive Value of the in Vitro Cell Line, Human Xenograft, and Mouse Allograft Preclinical Cancer Models," Clin. Cancer Res. 9:4227-4239 (2003).

Wang, P. et al., "Mechanisms of Ageing and Development (2003);HDTIC-1 and HDTIC-2, two components extracted from Astragali Radix, delay replicative senescence of human diploid fibroblasts," Mechanisms of Aging and Dev. 124:1025-1034 (2003.

Wassertheil-Smoller, S. et al., "Effect of estrogen plus progestin on stroke in postmenopausal women: the Women's Health Initiative: a randomized trial," JAMA 28:2673-2684 (2003).

Wong, B.Y. et al., "Chinese Medicinal Herb *Scutellaria barbata* Modulates Apoptosis in TRAMP-C1 Prostate Cancer Cells and Tumor Development in TRAMP Mice," American Assoication for Cancer Research Conference on Frontiers in Cancer Prevention Research, Oct. 26-30, 2003, Phoenix, AZ, Cancer Epidemiology, Biomarkers & Prevention 12(Supp):1326s, Poster Session B, Nov. 2003, Poster B190.

Wong, B.Y. et al., "Modulation of Apoptosis and Cell Survival in Human Prostate Cancer Cells by the Chinese Medicinal Herb *Scutellaria barbata*," American Association for Cancer Research Conference on Frontiers in Cancer Prevention Research, Oct. 30-Nov. 2, 2005, Baltimore, MD Poster Session B, Biomarkers and Early Detection:Health Disparities, Cell,Molecular and Tumor Biology: Cell Death, Poster B21, p. 104.

Writing Group for the Women's Health Initiative Investigators, 2002, "Risks and benefits of estrogen plus progesin in healthy postmeopausal women: principal results," From the Women's Health Initiative randomized controlled trial, JAMA 288:321-333 (2002).

Xiao-fan, Z. et al., Chinese Medicine Teas:Simple, Proven Folk Formulas for Common Disease Promoting Health (Aug. 2004, Blue Poppy Press, Third Printing USA; pp. 122, 123, 252, 253-255 and 263.

Yin, X. et al., "Anticancer activity and mechanism of *Scutellaria barbata* extract on human lung cancer cell line A549," Life Sciences 75:2233-2244 (2004).

Yu, H. et al., "Anti-tumor effect of Chinese herbal medicines "*Scutellaria barbata* and *Oldenlandia diffusa*" on cancer cell lines and C3H-AVy mouse with spontaneous hepatocellular carcinoma," J Traditional Medicines 17(4):165-169 (2000).

Zhang, et al., "In Vitro Estrogenic Activities of Chinese Medicinal Plants Traditionally Used for the Management of Menopausal Symptoms," J. of Ethnopharmacology 98:3:295-300 (Apr. 2005).

Zhu, F. et al., "Regulative Effect of Traditional Chinese Medicine on Gene-expression Related to Precancerous Lesion of Gastric Cancer," Chinese J. Integrative Med. 11(1):76-80 (2005).

PCT/US05/44292 Search Report dated May 15, 2006.
PCT/US08/75493 Search Report dated Dec. 3, 2008.
PCT/US08/75405 Search Report dated Nov. 24, 2008.
PCT/US08/75499 Search Report dated Nov. 24, 2008.
PCT/US08/75468 Search Report dated Nov. 19, 2008.
PCT/US08/72651 Search Report dated Nov. 7, 2008.
PCT/US08/67495 Search Report dated Sep. 18, 2008.
PCT/US06/11862 Search Report dated Oct. 30, 2008.
PCT/US06/044224 Search Report dated Nov. 7, 2007.

Chrzan et al., "Phytoestrogens activate estrogen receptor β1 and estrogenic responses in human breast and bone cancer cell lines," Mol. Nutr. Food Res. 51:171-177 (2007).

Guo et al., "Anticancer effect of aloe-emodin on cervical cancer cells involves G2/M arrest and inductions of differentiation," Acta Pharmacol. Sin. 28(12):1991-1995 (2007).

Harris et al., "Phytoestrogens Induce Differential Estrogen Receptor Alpha- or Beta-Mediated Responses in Transfected Breast Cancer Cells," Exp. Biol. Med. 230(8):558-568 (2005.

Matsuda et al., "Phytoestrogens from the roots of *Polygonum cuspidatum* (polygonaceae): structure-Requirement of hydroxyanthraquinones for estrogenic activity," Bioorganic and Medicinal Chemistry Letters 11(14):1839-1842 (2001).

Mueller et al., "Occurrence of Emodin, Chrysophanol and Physcion in Vegetables, Herbs and Liquors," Food and Chemical Toxicology 37(5):481-484 (1999).

Srinivas et al., "Emodin induces apoptosis of human cervical cancer cells through poly(ADP-ribose) polymerase cleavage and activation of caspase-9," Eur. J. Pharmacology 473:117-125 (2003).

PCT/US09/040557 Search Report dated Dec. 14, 2009.
PCT/US09/042915 Search Report dated Dec. 22, 2009.
PCT/US09/003427 Search Report dated Jan. 18, 2010.
PCT/US09/46496 Search Report dated Jan. 12, 2010.
EP05853254 Supplementary Search Report dated Jun. 11, 2009.
PCT/US08/84079 Search Report dated Jun. 24, 2009.
PCT/US05/44362 Search Report dated Jun. 22, 2006.

Boyce et al., "Src Inhibitiors in Metastatic Bone Disease," Clin. Cancer Res. 12(20 Suppl.):6291s-6295s (2006).

Camidge et al., "A first-in-man phase I tolerability and pharmacokinetic study of the cyclin-dependent kinase-inhibitor AZD5438 in healthy male volunteers," Cancer Chemother. Pharmacol. 60:391-398 (2007).

Centro Nacional De Investigaciones Oncologicas 2006, "CNIO Cancer Conference Medicinal Chemistry in Oncology," CNIO Cancer Conferences 2006:1-112.

Paez et al., "Response in Gefitinib Therapy," Science 304:1497-1500 (2004).

Rosano et al., "ZD4054, a Potent Endothelin Receptor A Antagonist, Inhibits Ovarian Carcinoma Cell Proliferation," Exp. Biol. Med. 231:1132-1135 (2006).

Ruff, "Targeted Therapy in Cancer in the $21^{st}$ Century," CME 25(2):77-80 (2007).

Yeh et al., "Biological Characterization of ARRY-142886 (AZD6244), a Potent, Highly Selective Mitogen-Activated Protein Kinase 1/2/ Inhibitor," Clin. Cancer Res. 13(5):1576-1583 (2007).

PCT/US08/84082 Search Report dated Feb. 3, 2009.
PCT/US08/84085 Search Report dated Feb. 4, 2009.
PCT/US08/84087 Search Report dated Feb. 5, 2009.
EP058852777 Supplementary Search Report and Opinion Oct. 18, 2010.

Fong et al., "Molecular mechanisms underlying selective cytotoxic activity of BZL101, an extract of *Scutellaria barbata*, towards breast cancer cells," Cancer Biol. Ther. 7(4):577-586 (2008).

* cited by examiner

Dose-response curves showing the response of several solid cancer tumor cells to BZL100.

Dose-response curves showing the response of breast solid cancer tumor cells to BZL101.

Dose-response curves comparing the response of breast solid cancer tumor cells and normal breast epithelium to BZL101.

Gel electrophoresis plate which demonstrates that nuclear DNA disintegration occurs during apoptosis of solid tumor cancer cells in contact with aqueous extracts of BZL101

BZL101 administered intraperitoneally (IP) reduces the growth of xenograft tumors in a mouse model.

- Day 0 – $10^5$ MCNeuA tumor cells, sc
- Herbs – 0.5 ml or 1.0 ml per mouse, i.p., every 2 days beginning day 0

The effect of the BZL101 administered by oral gavages and in interaction with cyclophosphamide administered in low dose in the drinking water on the tumors of mice in a xenograph model.

- Day 0 – $10^5$ tumor cells, sc
- CY – ~25 mg/kg/day, orally, beginning day 0
- Herb – 0.5 ml/mouse, every 3 days, beginning day 0

BZL101 induces apoptosis without activating caspases

BZL101 Does Not Induce Caspase Activation (CK18 cleavage assay)

BZL101 in cell cycle analysis arrests the cells at the G1 phase.

BZL101 arrests breast cancer cells in the G1 phase of the cell cycle and induces apoptosis as measured by a sub-G1 population of cells 8-Oxo-guanine

METHODS OF DETECTING AND TREATMENT OF CANCERS USING *SCUTELLARIA BARBATA* EXTRACT

CROSS REFERENCE

This application claims benefit of priority under 35 U.S.C. §119(e) from provisional patent application 60/989,065, filed Nov. 19, 2007, which is incorporated herein by reference in its entirety.

BACKGROUND OF THE INVENTION

While advances in early detection and adjuvant therapy for breast cancer have had a favorable impact on patient survival in general, patients who develop advanced metastatic breast cancer are generally likely to face a less favorable prognosis. Commonly used hormonal and chemotherapeutic agents can lead to transient regression of tumors and can also palliate symptoms related to cancer. However, these treatments are often accompanied by toxicities and intolerable side effects and eventually become ineffective in controlling advanced stage breast cancer and its symptoms. Improvements in survival are modest, even with newer targeted biological agents. Moreover, in most metastatic cancers resistance to available conventional treatment ultimately develops or excessive side effects are seen with conventional therapies.

It is interesting to note that greater than 60% of all chemotherapeutic agents used in the treatment of breast cancer are derived from natural substances (Newman 2003). A fairly recent example is the development of taxanes from the Pacific yew tree, *Taxus brevifolia*. Throughout the world, it is estimated that approximately 80% of the world population still relies on botanical medicine as the primary source of therapy. In the West botanical medicine is considered a popular form of complementary and alternative medicine among patients diagnosed with cancer. However, few clinical trials have been conducted to firmly assess the safety and efficacy of botanical agents for the treatment of breast cancer, despite anecdotal case reports of cures and clinical efficacy in women who have relied solely on botanical medicine for treatment. It has previously been shown that the aqueous extract of *Scutellaria Barbata* can lead to growth inhibition of breast cancer cell lines in vitro ("Antiproliferative activity of Chinese medicinal herbs on breast cancer cells in vitro," Anticancer Res., 22(6C):3843-52 (2002)). BZL101, a concentrated aqueous extract of *Scutellaria Barbata*, was evaluated for antiproliferative activity on five breast cancer cell lines (SK-BR-3, MCF7, MDA-MB-231, BT-474, and MCNeuA). These cell lines represent important prognostic phenotypes of breast cancer expressing a range of estrogen and HER2 receptors. BZL101, tested at a 1:10 dilution (15 µg/ml), demonstrated >50% growth inhibition on four of the five cell lines (Campbell, 2002). BZL101 showed >50% growth inhibition on a panel of lung, prostate and pancreatic cancer cell lines. BZL101 at the same dose did not cause >25% of growth inhibition on normal human mammary cells (HuMEC), demonstrating selectivity to cancer cells (Table 1). More so, BZL101 had a mild mitogenic effect on normal human lymphocytes. In cell cycle analysis, BZL101 caused an S phase burst and G1 arrest. BZL101 also attenuated mitochondrial membrane potential causing caspase-independent high molecular grade (HMG) apoptosis.

SUMMARY OF THE INVENTION

The inventor has recognized a need for improved methods of treating various types of cancer, especially ER$^-$ (e.g. ERα$^-$ and/or ERβ$^-$) breast cancer. Various embodiments of the invention provided herein meet the foregoing need and provide related advantages as well.

Some embodiments described herein provide a method of treating cancer in a patient, comprising: obtaining a tumor sample from the patient; (a) contacting a portion of the tumor sample with a composition comprising an extract of *Scutellaria barbata* D. Don; (b) detecting a level of a marker of DNA oxidation in the sample from the patient; and (c) if the level of marker of DNA oxidation in the sample exceeds a predetermined threshold, administering to the patient an effective amount of an extract of *Scutellaria Barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the level of the marker of DNA oxidation is determined by mass spectrometry.

A method of deciding whether to continue anticancer chemotherapeutic treatment with an extract of *Scutellaria barbata* D. Don, comprising: (a) obtaining a sample from a cancer patient treated with an extract of *Scutellaria barbata* D. Don; (b) determining a level of a marker of DNA oxidation in the sample; and (c) if the level of marker of DNA oxidation in the sample exceeds a predetermined level, continuing treatment with the extract of *Scutellaria barbata* D. Don. In some embodiments, the cancer is a breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the sample is a bodily fluid or a solid tissue. In some embodiments, the sample is a bodily fluid. In some embodiments, the bodily fluid is blood serum or urine. In some embodiments, the marker of DNA oxidation is 8-oxoguanine or lactate.

Some embodiments described herein provide a method of treating cancer in a patient, comprising: (a) treating the patient with a first dosage of extract of *Scutellaria barbata* D. Don; (b) obtaining a sample from the patient; (c) detecting in the sample a level of a marker of DNA oxidation; (d) if the level of the marker of DNA oxidation exceeds a predetermined level, continuing treatment with the first dosage of extract of *Scutellaria barbata* D. Don; and (e) if the level of the marker of DNA oxidation does not exceed the predetermined level, discontinuing treatment with *Scutellaria barbata* D. Don. In some embodiments, the cancer is a breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the sample is a bodily fluid or a solid tissue. In some embodiments, the sample is a bodily fluid. In some embodiments, the bodily fluid is blood serum or urine. In some embodiments, the marker of DNA oxidation is 8-oxoguanine or lactate.

Some embodiments described herein provide a method of treating cancer in a patient, comprising: (a) treating the patient with a first dosage of extract of *Scutellaria barbata* D. Don; (b) obtaining a sample from the patient; (c) detecting in the sample a level of a marker of DNA oxidation; (d) if the level of the marker of DNA oxidation exceeds a predetermined level, continuing treatment with the first dosage of extract of *Scutellaria barbata* D. Don; and (e) if the level of the marker of DNA oxidation does not exceed the predetermined level, increasing the dose of extract of *Scutellaria barbata* D. Don and continuing treatment. In some embodiments, the cancer is a breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the sample is a bodily fluid or a solid tissue. In some embodiments, the sample is a bodily fluid. In some embodiments, the bodily fluid is blood serum or urine. In some embodiments, the marker of DNA oxidation is 8-oxoguanine or lactate.

Some embodiments described herein provide a method of treating cancer in a patient, comprising: (a) obtaining a tumor sample from the patient; (b) contacting a portion of the tumor sample with a composition comprising an extract of *Scutellaria barbata* D. Don; (c) detecting a level of a gene that is up-regulated in a cell in which an extract of *Scutellaria barbata* D. Don is cytotoxic and which has been contacted with *Scutellaria barbata* D. Don; and (d) if the level of the gene exceeds a predetermined threshold, administering to the patient an effective amount of an extract of *Scutellaria Barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the method further comprises detecting a level of a second gene that is up-regulated in a cell in which an extract of *Scutellaria barbata* D. Don is cytotoxic and which has been contacted with *Scutellaria barbata* D. Don. In some embodiments, the method further comprises detecting a level of a third gene that is up-regulated in a cell in which an extract of *Scutellaria barbata* D. Don is cytotoxic and which has been contacted with *Scutellaria barbata* D. Don.

Some embodiments provide method of deciding whether to continue anticancer chemotherapeutic treatment with an extract of *Scutellaria barbata* D. Don, comprising: (a) obtaining a sample from a cancer patient treated with an extract of *Scutellaria barbata* D. Don; (b) determining a level gene that is up-regulated in a cell in which an extract of *Scutellaria barbata* D. Don is cytotoxic and which has been contacted with *Scutellaria barbata* D. Don; and (c) if the level of gene that is up-regulated exceeds a predetermined level, continuing treatment with the extract of *Scutellaria barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, L8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the method further comprises detecting a level of a second gene that is up-regulated in a cell in which an extract of *Scutellaria barbata* D. Don is cytotoxic and which has been contacted with *Scutellaria barbata* D. Don. In some embodiments, the method further comprises detecting a level of a third gene that is up-regulated in a cell in which an extract of *Scutellaria barbata* D. Don is cytotoxic and which has been contacted with *Scutellaria barbata* D. Don.

Some embodiments described herein provide a method of treating cancer in a patient, comprising: (a) treating the patient with a first dosage of extract of *Scutellaria barbata* D. Don; (b) obtaining a sample from the patient; (c) detecting in the sample a level of a gene that is up-regulated in a cell in which an extract of *Scutellaria barbata* D. Don is cytotoxic and which has been contacted with *Scutellaria barbata* D. Don; (d) if the level of the gene that is up-regulated in a cell in which an extract of *Scutellaria barbata* D. Don is cytotoxic exceeds a predetermined level, continuing treatment with the first dosage of extract of *Scutellaria barbata* D. Don; and (e) if the level of the gene does not exceed the predetermined level, discontinuing treatment with *Scutellaria barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the method further comprises detecting a level of a second gene that is up-regulated in a cell in which an extract of *Scutellaria barbata* D. Don is cytotoxic and which has been contacted with *Scutellaria barbata* D. Don. In some embodiments, the method further comprises detecting a level of a third gene that is up-regulated in a cell in which an extract of *Scutellaria barbata* D. Don is cytotoxic and which has been contacted with *Scutellaria barbata* D. Don.

Some embodiments described herein provide a method of treating cancer in a patient, comprising: (a) treating the patient with a first dosage of extract of *Scutellaria barbata* D. Don; (b) obtaining a sample from the patient; (c) detecting in the sample a level of a gene that is up-regulated in a cell in which an extract of *Scutellaria barbata* D. Don is cytotoxic and which has been contacted with *Scutellaria barbata* D. Don; (d) if the level of the a level of the gene that is up-regulated in a cell in which an extract of *Scutellaria barbata* D. Don is cytotoxic and which has been contacted with *Scutellaria barbata* D. Don exceeds a predetermined level, continuing treatment with the first dosage of extract of *Scutellaria barbata* D. Don; and (e) if the level of the gene does not exceed the predetermined level, discontinuing treatment with *Scutellaria barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the method further comprises detecting a level of a second gene that is up-regulated in a cell in which an extract of *Scutellaria barbata* D. Don is cytotoxic and which has been contacted with *Scutellaria barbata* D. Don. In some embodiments, the method further comprises detecting a level of a third gene that is up-regulated in a cell in which an extract of *Scutellaria barbata* D. Don is cytotoxic and which has been contacted with *Scutellaria barbata* D. Don.

Some embodiments described herein provide a kit comprising a therapeutically effective amount of an extract of *Scutellaria barbata* D. Don and a means for determining a level of a marker of DNA oxidation in a sample from the patient. In some embodiments, the marker of DNA oxidation is 8-oxoguanine or lactate.

Some embodiments described herein provide a kit comprising a therapeutically effective amount of an extract of *Scutellaria barbata* D. Don and a means for detecting a level of a gene that is up-regulated in a cell in which an extract of *Scutellaria barbata* D. Don is cytotoxic and which has been contacted with *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the gene participates in a xenobiotic response pathway, an oxidative response pathway, a NFκB pathway or an apoptosis/cell death pathway.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
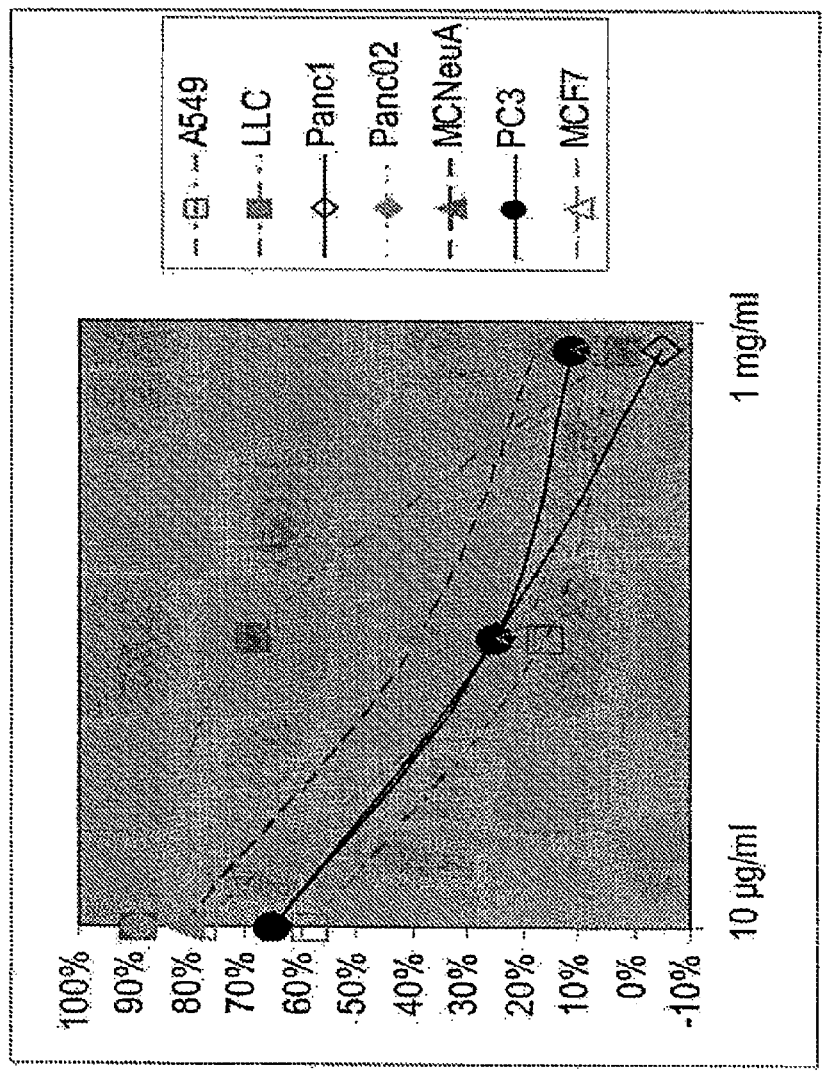
FIG. 1 shows dose-response curves showing the response of several solid cancer tumor cells to aqueous extract of the herb of this invention.

Some embodiments described herein provide a method of treating cancer in a patient, comprising: obtaining a tumor sample from the patient; (a) contacting a portion of the tumor sample with a composition comprising an extract of *Scutellaria barbata* D. Don; (b) detecting a level of a marker of DNA oxidation in the sample from the patient; and (c) if the level of marker of DNA oxidation in the sample exceeds a predetermined threshold, administering to the patient an effective amount of an extract of *Scutellaria Barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the level of the marker of DNA oxidation is determined by mass spectrometry.

A method of deciding whether to continue anticancer chemotherapeutic treatment with an extract of *Scutellaria barbata* D. Don, comprising: (a) obtaining a sample from a cancer patient treated with an extract of *Scutellaria barbata* D. Don; (b) determining a level of a marker of DNA oxidation in the sample; and (c) if the level of marker of DNA oxidation in the sample exceeds a predetermined level, continuing treatment with the extract of *Scutellaria barbata* D. Don. In some embodiments, the cancer is a breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the sample is a bodily fluid or a solid tissue. In some embodiments, the sample is a bodily fluid. In some embodiments, the bodily fluid is blood serum or urine. In some embodiments, the marker of DNA oxidation is 8-oxoguanine or lactate.

Some embodiments described herein provide a method of treating cancer in a patient, comprising: (a) treating the patient with a first dosage of extract of *Scutellaria barbata* D. Don; (b) obtaining a sample from the patient; (c) detecting in the sample a level of a marker of DNA oxidation; (d) if the level of the marker of DNA oxidation exceeds a predetermined level, continuing treatment with the first dosage of extract of *Scutellaria barbata* D. Don; and (e) if the level of the marker of DNA oxidation does not exceed the predetermined level, discontinuing treatment with *Scutellaria barbata* D. Don. In some embodiments, the cancer is a breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the sample is a bodily fluid or a solid tissue. In some embodiments, the sample is a bodily fluid. In some embodiments, the bodily fluid is blood serum or urine. In some embodiments, the marker of DNA oxidation is 8-oxoguanine or lactate.

Some embodiments described herein provide a method of treating cancer in a patient, comprising: (a) treating the patient with a first dosage of extract of *Scutellaria barbata* D. Don; (b) obtaining a sample from the patient; (c) detecting in the sample a level of a marker of DNA oxidation; (d) if the level of the marker of DNA oxidation exceeds a predetermined level, continuing treatment with the first dosage of extract of *Scutellaria barbata* D. Don; and (e) if the level of the marker of DNA oxidation does not exceed the predetermined level, increasing the dose of extract of *Scutellaria barbata* D. Don and continuing treatment. In some embodiments, the cancer is a breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the marker of DNA oxidation is 8-oxoguanine or lactate. In some embodiments, the sample is a bodily fluid or a solid tissue. In some embodiments, the sample is a bodily fluid. In some embodiments, the bodily fluid is blood serum or urine. In some embodiments, the marker of DNA oxidation is 8-oxoguanine or lactate.

Some embodiments described herein provide a method of treating cancer in a patient, comprising: (a) obtaining a tumor sample from the patient; (b) contacting a portion of the tumor sample with a composition comprising an extract of *Scutellaria barbata* D. Don; (c) detecting a level of a gene that is up-regulated in a cell in which an extract of *Scutellaria barbata* D. Don is cytotoxic and which has been contacted with *Scutellaria barbata* D. Don; and (d) if the level of the gene exceeds a predetermined threshold, administering to the patient an effective amount of an extract of *Scutellaria Barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the gene is up-regulated by at least about 1.8 fold over cellular expression in the absence of *Scutellaria barbata* D. Don. In some embodiments, the gene is selected from the group consisting of consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1 and HA-1. In some embodiments, the gene is up-regulated by at least about 1.9 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD and LTB4R. In some embodiments, the gene is up-regulated by at least about 2.0 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2 and TUBB2. In some embodiments, the gene is up-regulated by at least about 2.1 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL and SLC2A6. In some embodiments, the gene is up-regulated by about 2.2 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1 and CXCL16. In some embodiments, the gene is up-regulated by at least about 2.7 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6 and BBC3. In some embodiments, the gene is a gene involved in a cellular xenobiotic response. In some embodiments, the gene is CYP1A1, CYP1B1, HSPA6, CYP27B1. In some embodiments, the gene is a gene involved in the oxidative response pathway. In some embodiments, the gene is selected from the group consisting of HMOX1, TNFAIP3, OKL38, GCLM, CBS, ATF3, and TXNRD1. In some embodiments, the gene is involved in the NFκB pathway. In some embodiments, the gene is selected from the group consisting of HMOX1, CXCL1, CYP1B1, TNFAIP3, IGFL1, TNF, CLC, BIRC3, ICAM1, IL8, RELB, CCL2, SQSTM1, CLC, TIPARP, CCL2, PLAUR, TNFRSF21, GCLM, CBS, BBC3, ATF3, GADD45A, CCL11, RASD1, NFKBIE, PANX1, IRF1, TRAF3, EDN1, PBEF1, NEK6, NFKBIB, TPST1 and CDKN1A. In some embodiments, the gene is involved in the apoptosis/cell death pathway. In some embodiments, the gene is selected from the group consisting of TNFAIP3, TNF, BIRC3, CCL2, SQSTM1, CLC, TNFRSF21, BBC3, GADD45A, SAT, CCL11, NFKBIE, TRAF3, MMD and CDKN1A. In some embodiments, the method further comprises detecting a level of a second gene that is up-regulated in a cell in which an extract of Scutellaria barbata D. Don is cytotoxic and which has been contacted with Scutellaria barbata D. Don. In some embodiments, the method further comprises detecting a level of a third gene that is up-regulated in a cell in which an extract of Scutellaria barbata D. Don is cytotoxic and which has been contacted with Scutellaria barbata D. Don.

Some embodiments provide method of deciding whether to continue anticancer chemotherapeutic treatment with an extract of Scutellaria barbata D. Don, comprising: (a) obtaining a sample from a cancer patient treated with an extract of Scutellaria barbata D. Don; (b) determining a level gene that is up-regulated in a cell in which an extract of Scutellaria barbata D. Don is cytotoxic and which has been contacted with Scutellaria barbata D. Don in the sample; and (c) if the level of gene that is up-regulated exceeds a predetermined level, continuing treatment with the extract of Scutellaria barbata D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the gene is up-regulated by at least about 1.8 fold over cellular expression in the absence of Scutellaria barbata D. Don. In some embodiments, the gene is selected from the group consisting of consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1 and HA-1. In some embodiments, the gene is up-regulated by at least about 1.9 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD and LTB4R. In some embodiments, the gene is up-regulated by at least about 2.0 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2 and TUBB2. In some embodiments, the gene is up-regulated by at least about 2.1 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL and SLC2A6. In some embodiments, the gene is up-regulated by about 2.2 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1 and CXCL16. In some embodiments, the gene is up-regulated by at least about 2.7 fold over cellular expression in the absence of Scutellaria barbata D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6 and BBC3. In some embodiments, the gene is a gene involved in a cellular xenobiotic response. In some embodiments, the gene is CYP1A1, CYP1B1, HSPA6, CYP27B1. In some embodiments, the gene is a gene involved in the oxidative response pathway. In some embodiments, the gene is selected from the group consisting of HMOX1, TNFAIP3, OKL38, GCLM, CBS, ATF3, and TXNRD1. In some embodiments, the gene is involved in the NFκB pathway. In some embodiments, the gene is selected from the group consisting of HMOX1, CXCL1, CYP1B1, TNFAIP3, IGFL1, TNF, CLC, BIRC3, ICAM1, IL8, RELB, CCL2, SQSTM1, CLC, TIPARP, CCL2, PLAUR, TNFRSF21, GCLM, CBS, BBC3, ATF3, GADD45A, CCL11, RASD1, NFKBIE, PANX1, IRF1, TRAF3, EDN1, PBEF1, NEK6, NFKBIB, TPST1 and CDKN1A. In some embodiments, the gene is involved in the apoptosis/cell death pathway. In some embodiments, the gene is selected from the group consisting of TNFAIP3, TNF, BIRC3, CCL2, SQSTM1, CLC, TNFRSF21, BBC3, GADD45A, SAT, CCL11, NFKBIE, TRAF3, MMD and CDKN1A. In some embodiments, the method further comprises detecting a level of a second gene that is up-regulated in a cell in which an extract of Scutellaria barbata D. Don is cytotoxic and which has been contacted with Scutellaria barbata D. Don. In some embodiments, the method further comprises detecting a level of a third gene that is up-regulated in a cell in which an extract of Scutellaria barbata D. Don is cytotoxic and which has been contacted with Scutellaria barbata D. Don.

Some embodiments described herein provide a method of treating cancer in a patient, comprising: (a) treating the patient with a first dosage of extract of Scutellaria barbata D. Don; (b) obtaining a sample from the patient; (c) detecting in the sample a level of a gene that is up-regulated in a cell in which an extract of *Scutellaria barbata* D. Don is cytotoxic and which has been contacted with *Scutellaria barbata* D. Don; (d) if the level of the gene that is up-regulated exceeds a predetermined level, continuing treatment with the first dosage of extract of *Scutellaria barbata* D. Don; and (e) if the level of the gene does not exceed the predetermined level, discontinuing treatment with *Scutellaria barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the gene is up-regulated by at least about 1.8 fold over cellular expression in the absence of *Scutellaria barbata* D. Don. In some embodiments, the gene is selected from the group consisting of consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1 and HA-1. In some embodiments, the gene is up-regulated by at least about 1.9 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD and LTB4R. In some embodiments, the gene is up-regulated by at least about 2.0 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2 and TUBB2. In some embodiments, the gene is up-regulated by at least about 2.1 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL and SLC2A6. In some embodiments, the gene is up-regulated by about 2.2 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1 and CXCL16. In some embodiments, the gene is up-regulated by at least about 2.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6 and BBC3. In some embodiments, the gene is a gene involved in a cellular xenobiotic response. In some embodiments, the gene is CYP1A1, CYP1B1, HSPA6, CYP27B1. In some embodiments, the gene is a gene involved in the oxidative response pathway. In some embodiments, the gene is selected from the group consisting of HMOX1, TNFAIP3, OKL38, GCLM, CBS, ATF3, and TXNRD1. In some embodiments, the gene is involved in the NFκB pathway. In some embodiments, the gene is selected from the group consisting of HMOX1, CXCL1, CYP1B1, TNFAIP3, IGFL1, TNF, CLC, BIRC3, ICAM1, IL8, RELB, CCL2, SQSTM1, CLC, TIPARP, CCL2, PLAUR, TNFRSF21, GCLM, CBS, BBC3, ATF3, GADD45A, CCL11, RASD1, NFKBIE, PANX1, IRF1, TRAF3, EDN1, PBEF1, NEK6, NFKBIB, TPST1 and CDKN1A. In some embodiments, the gene is involved in the apoptosis/cell death pathway. In some embodiments, the gene is selected from the group consisting of TNFAIP3, TNF, BIRC3, CCL2, SQSTM1, CLC, TNFRSF21, BBC3, GADD45A, SAT, CCL11, NFKBIE, TRAF3, MMD and CDKN1A. In some embodiments, the method further comprises detecting a level of a second gene that is up-regulated in a cell in which an extract of *Scutellaria barbata* D. Don is cytotoxic and which has been contacted with *Scutellaria barbata* D. Don. In some embodiments, the method further comprises detecting a level of a third gene that is up-regulated in a cell in which an extract of *Scutellaria barbata* D. Don is cytotoxic and which has been contacted with *Scutellaria barbata* D. Don.

Some embodiments described herein provide a method of treating cancer in a patient, comprising: (a) treating the patient with a first dosage of extract of *Scutellaria barbata* D. Don; (b) obtaining a sample from the patient; (c) detecting in the sample a level of a gene that is up-regulated in a cell in which an extract of *Scutellaria barbata* D. Don is cytotoxic and which has been contacted with *Scutellaria barbata* D. Don; (d) if the level of the a level of the gene that is up-regulated exceeds a predetermined level, continuing treatment with the first dosage of extract of *Scutellaria barbata* D. Don; and (e) if the level of the gene does not exceed the predetermined level, discontinuing treatment with *Scutellaria barbata* D. Don. In some embodiments, the cancer is breast cancer. In some embodiments, the cancer is metastatic breast cancer. In some embodiments, the cancer is selected from the group consisting of sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some embodiments, the gene is functionally involved in a xenobiotic response pathway, an oxidative response pathway, a NFκB pathway or an apoptosis/cell death pathway. In some embodiments, the gene is up-regulated by at least about 1.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the gene is unregulated by at least about 1.8 fold over cellular expression in the absence of *Scutellaria barbata* D. Don. In some embodiments, the gene is selected from the group consisting of consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1 and HA-1. In some embodiments, the gene is up-regulated by at least about 1.9 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD and LTB4R. In some embodiments, the gene is up-regulated by at least about 2.0 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4AT, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2 and TUBB2. In some embodiments, the gene is up-regulated by at least about 2.1 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL and SLC2A6. In some embodiments, the gene is up-regulated by about 2.2 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1 and CXCL16. In some embodiments, the gene is up-regulated by at least about 2.7 fold over cellular expression in the absence of *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6 and BBC3. In some embodiments, the gene is a gene involved in a cellular xenobiotic response. In some embodiments, the gene is CYP1A1, CYP1B1, HSPA6, CYP27B1. In some embodiments, the gene is a gene involved in the oxidative response pathway. In some embodiments, the gene is selected from the group consisting of HMOX1, TNFAIP3, OKL38, GCLM, CBS, ATF3, and TXNRD1. In some embodiments, the gene is involved in the NFκB pathway. In some embodiments, the gene is selected from the group consisting of HMOX1, CXCL1, CYP1B1, TNFAIP3, IGFL1, TNF, CLC, BIRC3, ICAM1, IL8, RELB, CCL2, SQSTM1, CLC, TIPARP, CCL2, PLAUR, TNFRSF21, GCLM, CBS, BBC3, ATF3, GADD45A, CCL11, RASD1, NFKBIE, PANX1, IRF1, TRAF3, EDN1, PBEF1, NEK6, NFKBIB, TPST1 and CDKN1A. In some embodiments, the gene is involved in the apoptosis/cell death pathway. In some embodiments, the gene is selected from the group consisting of TNFAIP3, TNF, BIRC3, CCL2, SQSTM1, CLC, TNFRSF21, BBC3, GADD45A, SAT, CCL11, NFKBIE, TRAF3, MMD and CDKN1A. In some embodiments, the method further comprises detecting a level of a second gene that is up-regulated in a cell in which an extract of *Scutellaria barbata* D. Don is cytotoxic and which has been contacted with *Scutellaria barbata* D. Don. In some embodiments, the method further comprises detecting a level of a third gene that is up-regulated in a cell in which an extract of *Scutellaria barbata* D. Don is cytotoxic and which has been contacted with *Scutellaria barbata* D. Don.

Some embodiments described herein provide a kit comprising a therapeutically effective amount of an extract of *Scutellaria barbata* D. Don and a means for determining a level of a marker of DNA oxidation in a sample from the patient. In some embodiments, the marker of DNA oxidation is 8-oxoguanine or lactate.

Some embodiments described herein provide a kit comprising a therapeutically effective amount of an extract of *Scutellaria barbata* D. Don and a means for detecting a level of a gene that is up-regulated in a cell in which an extract of *Scutellaria barbata* D. Don is cytotoxic and which has been contacted with *Scutellaria barbata* D. Don. In some embodiments, the gene is selected from the group consisting of CYP1A1, HMOX1, LOC255324, CXCL1, CYP1B1, LOC440449, TNFAIP3, IGFL1, NPAS2, TNF, CLC, BIRC3, OKL38, ICAM1, IL8, RELB, CCL2, SQSTM1, CLC, CDH5, TIPARP, CCL2, PLAUR, TNFRSF21, GCLM, CBS, RNF24, AMSH-LP, ADM, HSPA6, BBC3, ELL2, ATF3, C20orf139, GADD45A, SAT, SLCO4A1, NKX3-1, CCL11, MGAM, RASD1, ZSWIM4, NFKBIE, P53AIP1, NICAL, CCRN4L, RAPGEFL1, CA8, ARRDC2, NELF, PHLDA2, CLDN1, IER5, PIK3CD, PANX1, CXCL16, KRT5, MYEOV, SNAPC4, ERBP, UBE2E2, ZFP36, PLK2, SQRDL, SLC2A6, TUBB6, RCL1, ABCC2, LRFN1, MGC35521, IRF1, SAT, OPTN, SESN2, TUBB2, CPEB2, FADS3, NCOA7, TRAF3, TRIM21, EGR1, MOBKL2C, PEO1, DDX31, TXNRD1, EDN1, TIGA1, TM4SF14, AXIN1, MMD, CEBPD, LTB4R, PBEF1, WDR3, NEK6, PLEKHF1, PLEK2, FKSG27, CORO1C, SNAI1, MOBKL1A, CYP27B1, PUS1, NFKBIB, UBE2E1, HA-1, PWP2H, TPST1, CDKN1A and ZNF529. In some embodiments, the gene participates in a xenobiotic response pathway, an oxidative response pathway, a NFκB pathway or an apoptosis/cell death pathway.

Pharmaceutical Compositions and Modes of Administrations

An extract of this invention can be administered to a patient either as a "tea," without combination with any other substances or further manipulation, or it can be administered as a pharmaceutical composition where the extract is mixed with suitable carriers or recipient(s). In treating a patient exhibiting a disorder of interest, a therapeutically effective amount of the extract is administered. A therapeutically effective amount refers to that amount of the extract that results in amelioration of symptoms or a prolongation of survival in a patient, and may include destruction of a malignant tumor of a microbial infection.

When administered without combination with any other substances, the composition comprising extract of *Scutellaria Barbata* (especially *Scutellaria Barbata* D. Don) may be encased in a suitable capsule, such as a gelatin capsule. When administered in admixture with other excipients, adjuvants, binders, diluents, disintegrants, etc., the dry extract of *Scutellaria Barbata* may be compressed into a capsule or caplet in a conventional manner that is well-known in the art.

Toxicity and therapeutic efficacy of the extracts, i.e., determining the LD50 (the dose lethal to 50% of the population) and the ED50 (the dose therapeutically effective in 50% of the population) can be determined by standard pharmaceutical procedures in cell cultures or experimental animals. The dose ratio between toxic and therapeutic effects is therapeutic index and it can be expressed as the ratio LD50/ED50. Extracts that exhibit large therapeutic indices are preferred. The data obtained from these cell culture assays and animal studies can be used in formulating a range of dosages for use in humans, in particular for internal use, that include ED50 with little or no toxicity. The dosage may vary within this range depending upon the dosage form employed and the route of administration utilized. In general, since the extracts used in the methods of this invention have been used in TCM, they are known to be relatively non-toxic to humans and therefore it is expected that they will exhibit large therapeutic indices.

For any extract used in the method of invention, therapeutically effective dose can be estimated initially from cell culture assays. For example, a dose can be formulated in animal models to achieve a circulating plasma concentration range that includes the IC50 as determined in cell culture. Such information can be used to more accurately determine useful doses in humans. Levels in plasma may be measured, for example, by HPLC.

The exact formulation, route of administration and dosage can be chosen by the individual physician in view of the patient's condition and based on knowledge of TCM. (See e.g. Fingl et al., in The Pharmacological Basis of Therapeutics, 1975, Ch. 1, p. 1). It should be noted that the attending physician would know how and when to terminate, interrupt, or adjust administration due to toxicity, or organ dysfunction. Conversely, the attending physician would also know to adjust treatment to higher levels if the clinical response is not adequate. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

If desired, standard western medicine techniques for formulation and administration may be used, such as those found in *Remington's Pharmaceutical Sciences*, $18^{th}$ ed., Mack Publishing Co., Easton, Pa. (1990). Suitable routes may include: oral, rectal, transdermal, vaginal, transmucosal, or intestinal administration; parenteral delivery, including intramuscular, subcutaneous, intramedullary injections; as well as intrathecal, direct intraventricular, intravenous, intraperitoneal, intranasal, or intraocular injections, to name a just a few. In particular embodiments, the extract of the invention is administered orally.

For injection, an extract of this invention may be formulated in aqueous solutions, preferably in physiologically compatible buffers such as Hanks's solution, Ringer's solution, or physiological saline buffer, For such transmucosal administration, penetrants appropriate to the barrier to be permeated are used in the formulation. Such penetrants are generally known in the art.

Use of pharmaceutically acceptable carriers to formulate an extract herein use in the methods disclosed for the practice of this invention in dosages suitable for systemic administration is within the scope of the invention. With proper choice of carrier and suitable manufacturing practice, an extract of the present invention, in particular those formulated as solutions, may be administered parenterally, such as by intravenous injection. Likewise, an extract can be formulated, using pharmaceutically acceptable carriers well known in the art, into dosages suitable for oral administration. Such carriers enable extracts to be formulated as tablets, pills, capsules, liquids, gels, syrups, slurries, suspensions and the like, for oral ingestion by a patient to be treated.

Pharmaceutical compositions suitable for use in the present invention are compositions wherein an extract is contained in an effective amount to achieve its intended purpose. Determination of the effective amount is well within the capability of those skilled in the art, especially in light of the detailed disclosure provided herein. A pharmaceutical composition may contain suitable pharmaceutically acceptable carriers including excipients and auxiliaries that facilitate processing of the extracts into preparations that can be used pharmaceutically. The preparations formulated for oral administration may be in the form of tablets, dragees, capsules, or solutions. The pharmaceutical compositions of the present invention may be manufactured in a manner that is itself known, e.g., by means of convention mixing, dissolving, granulating, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutically formulations for parenteral administration include aqueous solutions of an extract in water-soluble form. Additionally, suspensions of an extract may be prepared as appropriate oily injection suspensions may contain substances that increase the viscosity of the suspension, such as sodium carboxymethyl cellulose, sorbitol, or dextran. Optionally, the suspension may also contain suitable stabilizers or agents that increase the solubility of an extract to allow for the preparation of highly concentrated solutions.

Pharmaceutical preparations for oral use can be obtained by combining an extract with solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum Arabic, talc, polyvinyl pyrrolidone, carpool gel, polyethylene glycol, and/or titanium dioxide, lacquer solutions, and suitable organic solvents or solvent mixtures. Dyestuffs or pigments may be added to the tablets or dragee coatings for identification or to characterize different combinations of extracts and/or doses.

Pharmaceutical preparations that can be used orally include push-fit capsules made of gelatin, as well as soft, sealed capsules made of gelatin and a plasticizer, such as glycerol or sorbitol. The push-fit capsules contain the extract in admixture with fillers such as lactose, binders such as starches, and/or lubricants such as talc or magnesium separate and, optionally, stabilizers. In soft capsules, the extract may be dissolved or suspended in suitable liquids, such as fatty oils, liquid paraffin, or liquid polyethylene glycols.

The dosage of extract of *Scutellaria barbata* D. Don will vary depending upon the tumor type, the stage of disease, the species of patient and the individual patient. In some embodiments, the amount of extract of *Scutellaria barbata* D. Don (BZL) administered to a human patient will be the dry solid residue extracted from about 0.1 g to about 20,000 g of dried solid plant parts of BZL. In some embodiments, the effective dose is the dry solid residue extracted from about 1 to about 1000 g of BZL. In some embodiments, the effective dose will be the dry solid residue extracted from about 10 to about 800 g of BZL.

Treatment of Cancers

Extracts of *Scutellaria barbata* D. Don may be used to treat solid tumors. Such tumors may include so-called estrogen receptor negative (ER$^-$) breast cancer, estrogen receptor positive (ER$^+$) cancer, and other solid tumor cancers. As used herein, the terms "estrogen receptor negative breast cancer" and "estrogen receptor positive breast cancers," have meanings commonly ascribed to them in the art. The person skilled in the art will recognize that the terms "positive" and "negative" are relative terms describing levels of expression in a cell. In general, saying that a cell is "negative" for expression of a particular cell product means that the level of expression detected, if any, falls below a predetermined threshold. That threshold may be a detection limit, a background noise level or some arbitrary cutoff known and understood by one of skill in the art. As extracts of *Scutellaria barbata* D. Don do not necessarily require presence of ERα or ERβ in order to induce apoptosis in solid cancer cells, it is considered that doses of *Scutellaria barbata* D. Don may be used to treat, inter alia, either ER$^+$ or ER$^-$ breast cancers as well as other solid tumors. The dose of *Scutellaria barbata* D. Don extract may vary, however it is considered that a dose comprising the dry soluble portion of a hot water or ethanolic extract of about 1 to about 20,000 g, especially about 50 to about 10,000 g of dry aerial portions of *Scutellaria barbata* D. Don, is a therapeutically effective dose. When used in combination with another chemotherapeutic agents, the dose may be lowered to take advantage of synergetic effects. C that extracts of *Scutellaria barbata* D. Don may be used to treat include sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma and retinoblastoma. In some particular embodiments, the Kits Also provided herein are kits for treatment of cancer. In some embodiments, the kits comprise an extract of *Scutellaria barbata* D. Don. In some embodiments, a the extract of *Scutellaria barbata* D. Don is in an oral dosage form. In some embodiments, the kit will contain sufficient extract of *Scutellaria barbata* D. Don for administration over 1, 2, 3, 4 or more weeks. In some embodiments, the dosage of extract of *Scutellaria barbata* D. Don will be divided into daily or twice daily doses. The daily dose of extract of *Scutellaria barbata* D. Don may vary depending on the second chemotherapeutic agent, the disease to be treated, the condition of the patient, etc. In general, the daily dose of extract of *Scutellaria barbata* D. Don will be the dried soluble extract of about 1 to 20,000 g, 10 to 10,000 g or 50 to 5000 g of dried aerial portion of *Scutellaria barbata* D. Don. The daily dose may be divided into 2, 3, 4 or more doses per day. When administered as a tea, the doses may be combined with a flavor or flavor-masking agent in order to enhance palatability.

Some embodiments described herein provide a kit for treatment of cancer, comprising a therapeutically effective amount of a first chemotherapeutic agent comprising an extract of *Scutellaria Barbata* D. Don and a means for testing a level of expression of a gene that is up-regulated in a cell in which an extract of *Scutellaria barbata* D. Don is cytotoxic and which has been contacted with *Scutellaria barbata* D. Don. The means for testing may include reagents and/or instructions for work-up methods for preparing a sample for evaluation on a gene chip or by mass spectrometry or both. The means may include antibodies (including labeled antibodies) for ELISA or similar methods. The means may include PCR probes and/or mass spectrometry standards for mass spectrometry measurements.

EXAMPLES

The herb from which the extracts of this invention were obtained were purchased from Shen Nong Herbs, Berkeley, Calif. Their identity was confirmed by reference to traditional pharmaceutical literature.

Preparative Example 1

Preparation of BZL101 for in vitro and Mouse Experiments

Herbal extract was prepared as "boiled teas", which is how most are prepared for use in traditional treatment regimes. Aqueous extracts were prepared by adding 7.5 g of dry ground herb to 125 ml distilled water, bringing the mixture to a boil and then simmering for 45 minutes, The mixture was cooled, during which period most of the solids sank to the bottom of the vessel. The aqueous layer was carefully decanted off of the residual solids, centrifuged for 5 minutes at 1500 rpm, sterile filtered through a 0.45 µm filter and stored at 4° C. until used. Generally, the extracts were tested within 1-2 weeks of preparation although most of the active extracts were found to retain activity after storage at 4° C. for several additional weeks. An aliquot of each extract was dried under vacuum and the dry weight of the water soluble substances extracted from each herb determined.

Preparative Example 2

Preparation of BZL101 for Human in vivo Experiments

BZL101 is an aqueous extract of the aerial part of *Scutellaria Barbata* D. Don of the Lamiaceae family. Herba *Scutellaria Barbata* D. Don (Chinese pin yin transliteration—Ban Zhi Lian (BZL)) is grown mainly in areas southeastern of the Yellow River (Huang Po) in the provinces of Sichuan, Jiangsu, Jiangxi, Fujian, Guangdong, Guangxi and Shaanxi. The plant is harvested in late summer and early autumn after it blooms. The aerial part (leaves and stems) is cut from the root and is used as starting material (BZL). The aerial part of the herb is dried in the sun, packed as a whole plant. The herb is identified and verified through botanical, morphological and chemical characteristics to ensure purity.

A single dose of BZL101 is made through the following procedure and is termed BZL101 (Bionovo, Inc., Emeryville, Calif.).
- 180 grams of the raw herb is ground to fine powder (25 mesh)
- The powder is mixed with 1800 ml of distilled water to form a slurry
- The slurry is than simmered at 70-72° C. for 60 minutes
- The extract is decanted and filtered through 22 µm filter
- The supernatant weight after extraction is 168 gm
- The volume of the solution is 1750 ml
- The extract is concentrated with a vacuum evaporator to reduce the volume of water to 350 ml which constitutes a 5:1 concentration of the original solution
- The dry weight of soluble material in the extract is 12 gm
- It is packaged in a sterile, vacuum sealed container
- Testing for bacteria, yeast and heavy metals are preformed by an accredited laboratory

Comparative Example 1

In vitro Inhibition of Cancer Cell Activity Cell Lines and Culture

The extract obtained in Preparative Example 1, above, was tested against four human breast cancer cell lines, SKBR3, MFC-7, MDA-MB231 and BT474, and one murine breast cancer cell line, MCNeuA. All lines were maintained in 90% DME supplement with 2.0 mom L-glutamine, 100 IU/ml penicillin, 100 µg/ml streptomycin and 10% heat-inactivated fetal bovine serum. Cells at 70-80% confluence were used for plating for growth inhibition assays.

Figure 2:
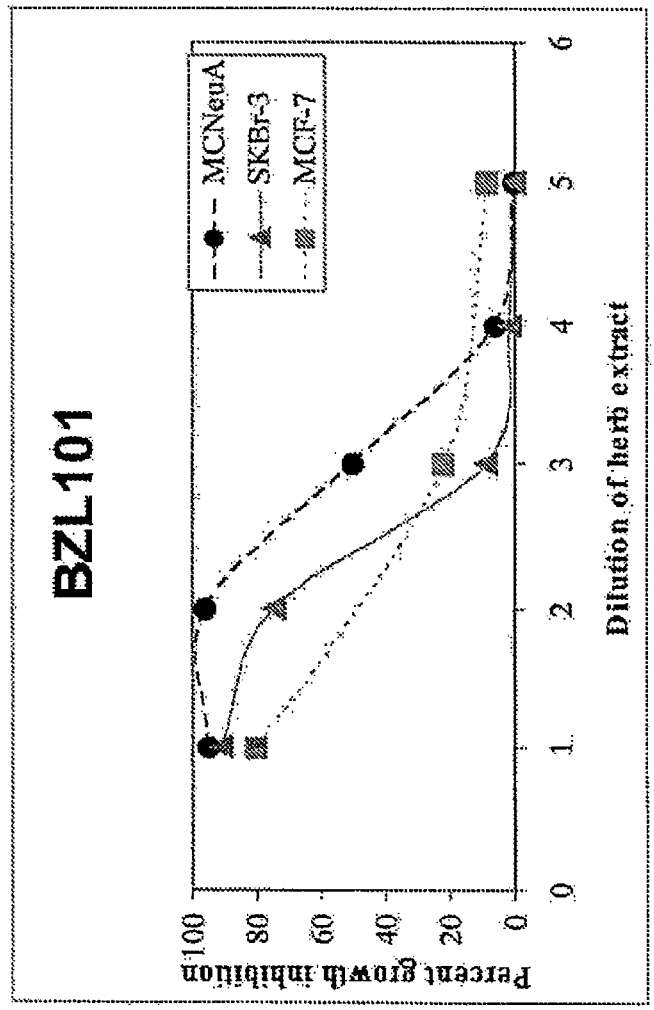
FIG. 2 shows dose-response curves showing the response of several breast solid cancer tumor cells to aqueous extract of the herb of the invention.
Figure 3:
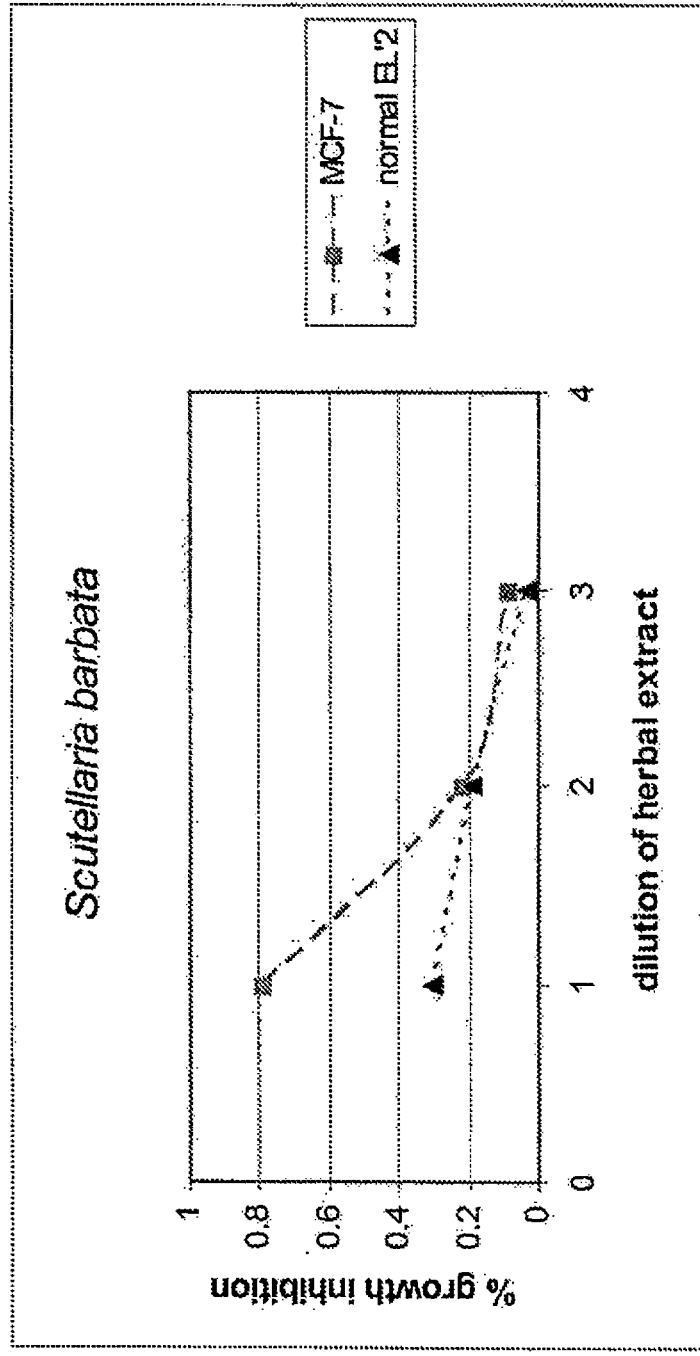
FIG. 3 shows dose-response curves comparing the response of breast solid cancer tumor cells and normal breast epithelium to aqueous extract of the herb of this invention.

Cells were plated in 96-well flat bottom plates at 5,000 to 10,000 cells/well. The difference in number of cells plated adjusts for differences in the growth rates of these cell lines. Cells were allowed to adhere to the well walls overnight; then the extracts were added to triplicate wells at a 1:10 final dilution in culture medium for initial screening. For generating dose-response curves, serial 3-fold dilutions, starting at 1:10 dilution over 6 rows of wells were used. Water was added to the control wells at 1:10 dilution in culture medium. The plates were incubated at 37° C., 5% $CO_2$, for 3 days and then assayed for growth inhibition using a crystal violet assay (Bernhardt, G., et al., *Standardized Kinetic Microassay to Quantify Differential Chemosensitivity on the Basis of Proliferative Activity*, 1992, J. Cancer Res. Clin. Oncol., 118:35-43). Cells remaining adherent to the well walls were rinsed with PBS, the fixed cells were stained with 0.02% aqueous crystal violet (50 µl/well) for 30 minutes after which the wells were washed thoroughly with distilled water. The crystal violet stain bound by the cells was solubilized in 79% ethanol (100 µl/well) and the plates analyzed on a microplate reader (Molecular Devices) ay 595 nm. The percent inhibition was calculated as the average optical density of the control wells minus average optical density extract well divided by the average optical density of the control wells. Dose-response curves on SKBR3, MCF7 and MCNeuA cells for several of the extracts are shown in FIGS. 1-3. As can be seen, the concentration at which the extracts inhibited the activity of the cells by 50% (the IC50) ranged from over 1 mg/ml down to about 10 µg/ml.

Induction of Apoptosis

Figure 4:
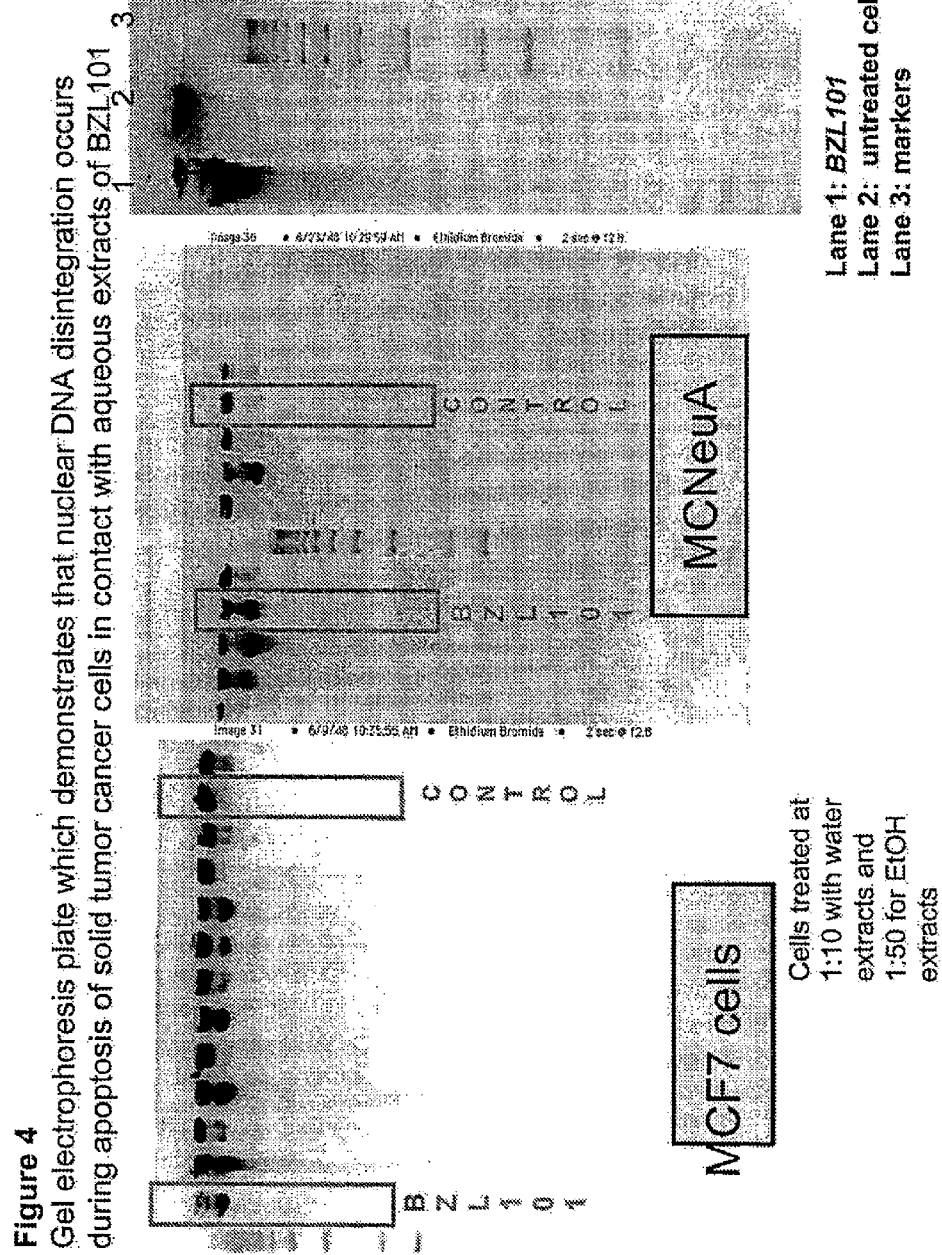
FIG. 4 shows gel electrophoresis plate, which demonstrates that nuclear DNA disintegration occurs during apoptosis of solid tumor cancer cells in contact with aqueous extracts of the herb of this invention.
Figure 5:
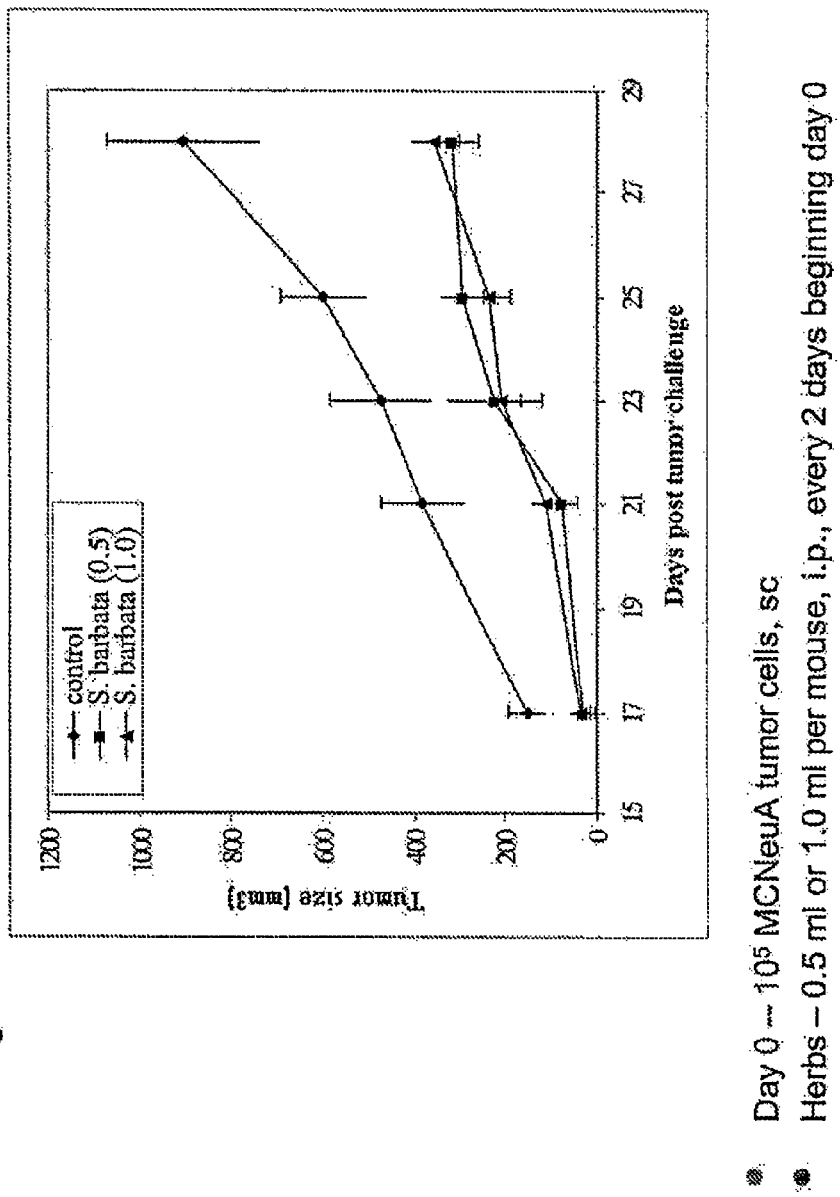
FIG. 5 shows the effect of the herb extract of the invention administered intraperitoneally (IP) on the tumors of mice in a xenograft model.
Figure 6:
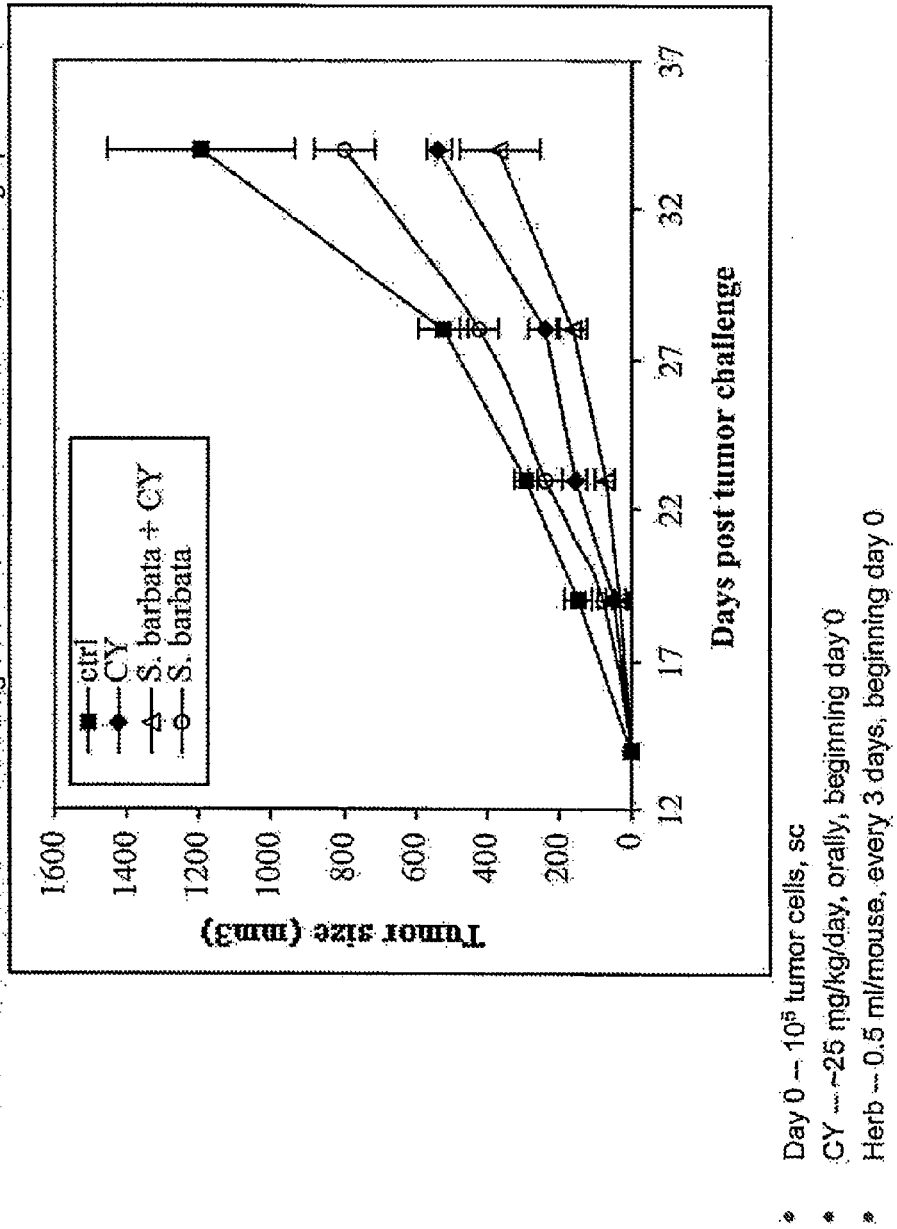
FIG. 6 shoes the effect of the herb extract administered by oral gavages and in interaction with cyclophosphamide administered in low dose in the drinking water on the tumors of mice in a xenograft model.

To assay for DNA fragmentation as a marker of apoptosis, a procedure for the isolation of genomic DNA that allows for the analysis of both high and low molecular weight DNA fragmentation during apoptosis was used. MCNeuA cells were plated at $5 \times 10^5$ cells/well in 6-plates and allowed to adhere overnight. Aqueous herbal extracts were added to each well at a 1:10 and a 1:50 dilution. Sterile water, diluted 1:10 in culture medium, was added to the control wells. After 24 hours, the cells were visually examined under a microscope and morphological changes noted. Attached and floating cells were harvested, washed with cold PBS and embedded in lysis buffer (50 mM NaCl, 20 mM Tris HCl, pH 8.0, 20 mM EDTA, 0.5% sodium sarkosyl, 50 µg/ml Rnase A and 100 µg/ml proteinase K) for 1 hour at 37° C. The cells were then washed with PBS and distilled water and placed in the wells of a conventional 1% agarose gel and electrophoresed overnight at approximately 1 V/cm. The gels were then stained with ethidium bromide and photographed under UV transillumination to give intense images. The images obtained are shown in FIG. 4.

Figure 7:
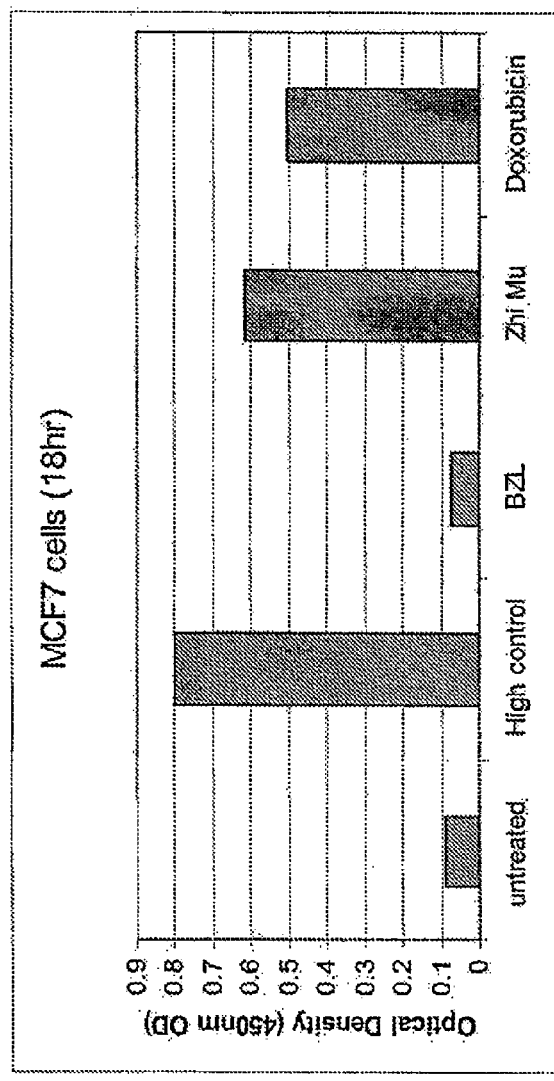
FIG. 7 shows that the herb extract induces apoptosis without activating caspases.
Figure 8:
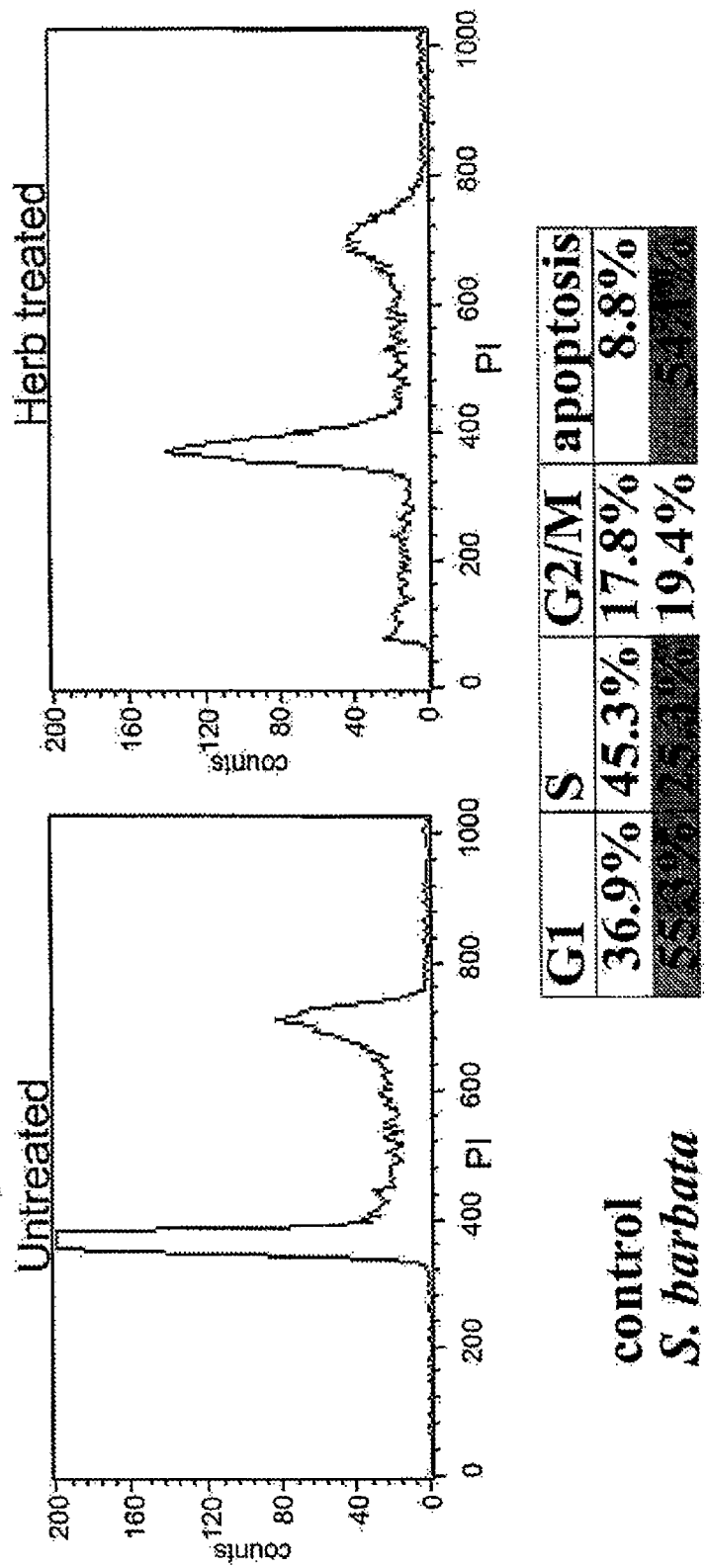
FIG. 8 shows that the herb extract in cell cycle analysis arrests the cells at the G1 phase.

BZL101 was evaluated for antiproliferative activity on five breast cancer cell lines (SK-BR-3, MCF7, MDA-MB-231, BT-474, and MCNeuA). These cell lines represent important prognostic phenotypes of breast cancer expressing a range of estrogen and HER2 receptors. BZL101, tested at a 1:10 dilution (15 µg/ml), demonstrated >50% growth inhibition on four of the five cell lines (Campbell, 2002). BZL101 showed >50% growth inhibition on a panel of lung, prostate and pancreatic cancer cell lines. BZL101 at the same dose did not cause >25% of growth inhibition on normal human mammary cells (HuMEC), demonstrating selectivity to cancer cells (Table 3). Moreso, BZL101 had a mild mitogenic effect on normal human lymphocytes. In cell cycle analysis, BZL101 caused an S phase burst and G1 arrest. (See FIG. 8). BZL101 also attenuated mitochondrial membrane potential causing caspase-independent high molecular grade (HMG) apoptosis. (See FIG. 7).

The results of this in vitro experiment are summarized in Table 3, below.

TABLE 3

In vitro growth inhibitory effect of BZL101 aqueous extract of *Scutellaria Barbata* 1:10 dilution− < 50% inhibition, + 51-75% inhibition, ++ > 75% inhibition.
BZL is active on all cancer cell lines but is not active on HuMECs.

| Lung | | Pancreas | | Prostate | | Breast | | | | MCNeuA | HuMEC |
|---|---|---|---|---|---|---|---|---|---|---|---|
| A549 | LLC | Panc-1 | 02 | PC-3 | LNCaP | MCF7 | BT474 | SKBR3 | MDA-MB-231 | | |
| + | + | + | ++ | + | + | ++ | + | ++ | + | ++ | − |

Example 1

Methods of Detecting Urinary Analysis of 8-oxoguanine, 8-oxoguanosine, fapy-guanine and 8-oxo-2'-deoxyguanosine as a Biomarker of Efficacy in the Treatment of BZL101 in Patients with Adenocarcinoma Rationale Reactive oxygen species (ROS) have been strongly associated with cellular aging, cancer, and other degenerative diseases by virtue of their potential to damage several cellular constituents, such as nucleic acids, proteins, and lipids. It is now well established that free radical mediated oxidation of DNA leads to a broad spectrum of chemical modifications which translate into single or double DNA strand breaks, and base as well as sugar modifications. Among the DNA base modifications induced by oxidative damage, 8-oxoguanine (8-oxoGua) is of particular relevance and has been proposed as a biomarker of DNA oxidation. The DNA guanine base oxidation product 8-oxo-2'-deoxyguanosine (8-oxodG) is potentially mutagenic and commonly quantified as a steady-state estimate of oxidative stress in tissues and urine using chromatographic techniques.

The urinary excretion of products of damaged nucleotides in cellular pools or in DNA may be important biomarkers of exposure to relevant carcinogens and may predict cancer risk or response to treatment. It is important to recognize that in steady state the excretion reflects the rate of damage. Among the many oxidative DNA damage products 8-oxo-7,8-dihydro-2'-deoxyguanosine (8-oxodG) is probably the most studied because of the relative ease of measurement and the mutagenic properties resulting in G→T transversion mutations upon replication of DNA.

Oxidized guanine in DNA is mainly repaired by oxoguanine glycosylase (OGG1) resulting in release of 8-oxoguanine. This enzyme shows a common genetic polymorphism with a variant Ser326Cys, which in complementation assays in vitro appears to increase susceptibility to mutagenic properties of ROS considerably, whereas 8-oxodG levels and incision activity in leukocytes and some target tissues generally show no difference between the genotypes. In addition, repair of 8-oxodG may to some extent occur by nucleotide excision repair and transcription coupled mechanisms. A specialized enzyme (MTH1 or NUDT1) sanitizes the nucleotide pool by cleaving phosphates of 8-oxodGTP which if incorporated during DNA synthesis is highly mutagenic and mice deficient in that enzyme develop tumors. 8-OxodG from this process as well as from putative nucleotide excision repair and possibly mitochondrial turn-over is excreted unchanged into the urine and may serve as a biomarker of oxidative stress and oxidative damage to nucleotides and possibly DNA. The urinary excretion of 8-oxodG has consistently been found to be increased among smokers and with a number of occupational exposures, including air pollution among bus drivers. Moreover, some case—control studies have suggested that the urinary excretion of 8-oxodG or 8-oxoguanine is increased among cancer patients, although this could very well be a consequence of the disease with ongoing oxidative stress, inflammation and tissue turn-over.

Furthermore, a great emphasis has being placed on the role of ROS-induced DNA damage in carcinogenesis and aging as a consequence of genomic degradation.

In recent years, there has been an increased interest in the use of mass spectrometry (MS) for the analysis of DNA oxidation products. MS typically provides structural information and selective detection in the picogram to femtogram range.

Therefore, given these characteristics, mass spectrometry is well positioned to play a significant role in the detection and characterization of DNA adducts. Besides the well-established role of DNA oxidative damage in many disease conditions, growing evidence points towards a significant involvement of RNA oxidative damage in the pathophysiology of several age-related degenerative disorders including cancer. Indeed, although little is still known about the consequences of RNA oxidation on the cellular homeostasis, it has been recently shown that oxidized RNA is associated with impaired protein synthesis as a consequence of translation errors. Moreover, RNA has been found to be significantly oxidized in age-related degenerative diseases.

BZL101 and 8-oxo-guanine

It is considered that differential induction of DNA damage by BZL101 in different cell types might be related to the extent of oxidative stress generated by BZL101 treatment. BZL101 induced a significant accumulation of ROS in SKBr3 cells as measured by staining with the ROS-sensitive probe CM-$H_2$DCFDA. Incubation of cells with ROS scavenger N-acetyl-cysteine (NAC) prior to addition of BZL101 has prevented most of the increase in ROS generation, confirming that the conversion of non-fluorescent CM-$H_2$DCFDA into fluorescent compound is indeed due to ROS. To confirm that BZL101 induces oxidative stress responses, the levels of transcriptional factor Nrf2 in BZL101 treated cells were examined. Nrf2 is a key regulator of phase II detoxifying and antioxidant enzymes that are upregulated in response to oxidative stress. Western blot analysis showed a significant and sustained increase in Nrf2 levels in BZL101 treated BT474 cells and SKBr3 cells. In MCF10A cells, there was also an increase in Nrf2 levels, though it was more transient in nature.

There is a different fold increase of ROS levels in different cells treated with BZL101 compared to control untreated cells. It is of particular interest that the increase in ROS correlates well with the degree of DNA damage induced in these cells. The lowest induction is seen in MCF10A cells which also have the lowest number of comets after treatment with BZL101, and the highest increase in ROS is observed in SKBr3 cells where the DNA damage is most extensive. In fibroblasts IMR90 and in BT474 cells the moderate increase in ROS paralleled the relatively lower extent of DNA damage compared to SKBr3.

To further implicate ROS in the induction of DNA damage, comet formation in cells pretreated with the antioxidants NAC and pyruvate prior to the addition of BZL101 were examined. Both compounds have significantly reduced the number of cells forming comets, in particular in normal cell lines. DNA damage repair in cancer cells in the presence of NAC or pyruvate was also greatly accelerated (not shown). At the same time, pretreatment of cells with the nitric oxide scavenger PTIO had no effect on the numbers of cells with comets (not shown), indicating that most of DNA lesions induced by BZL101 are oxidative in nature.

Figure 9:
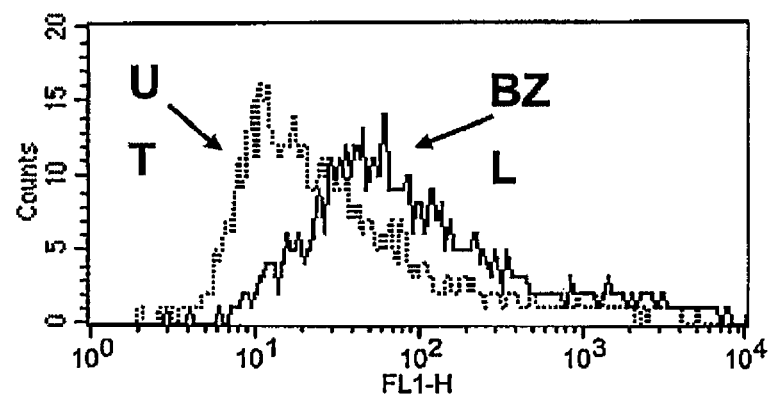
FIG. 9 shows that illustrates that BZL101 leads to oxidative DNA damage. Formation of 8-oxoguanine, the most ubiquitous marker of DNA oxidation, was quantified through flow cytometric analysis of fixed permeabilized cells incubated with avidin fluorescein, that was shown to bind relatively specifically to 8-oxoguanine. There is a clear increase in binding of avidin to BZL101 treated SKBr3 cells versus untreated cells.
Figure 10:
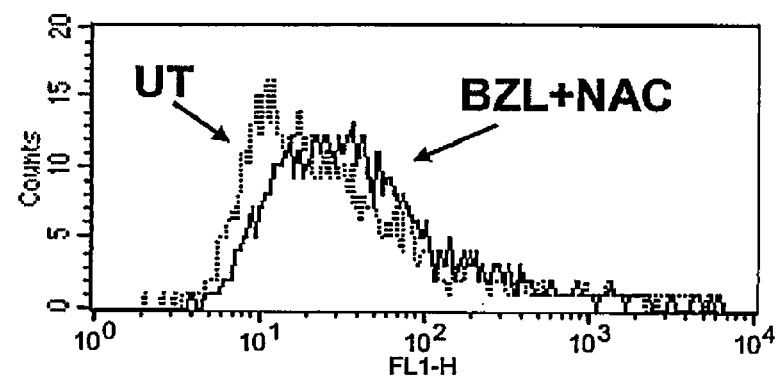
FIG. 10 shows that the conversion of non-fluorescent CM-H$_2$DCFDA into fluorescent compound is indeed due to ROS. Incubation of cells with ROS scavenger N-acetyl-cysteine (NAC) prior to addition of BZL101 prevented most of the increase in ROS generation.

To verify that BZL101 leads to oxidative DNA damage, it was determined whether the DNA of BZL101-treated cells contains 8-oxoguanine, the most ubiquitous marker of DNA oxidation. Formation of 8-oxoguanine has been quantified through flow cytometric analysis of fixed permeabilized cells incubated with avidin fluorescein, that was shown to bind relatively specifically to 8-oxoguanine. There is a clear increase in binding of avidin to BZL101 treated SKBr3 cells versus untreated cells. (See FIG. 9). This increase was completely abolished if cells were pretreated with NAC prior to addition of BZL101, confirming the specificity of observed staining. (See FIG. 10).

Analysis of the 8-oxoguanidine and apurininc/apyrimidinic (AP) bases in DNA. The Calbiochem kit was used for staining of the fixed and permeabilized cells with avidin fluorescein. Quantification of apurinic/apyrimidininc nucleotides in genomic DNA was performed using the DNA damage quantification kit from BioVision Research Products.

Example 4

Micro Array Gene Expression Signature Profiling for Patient Selection for Treatment with BZL101

A micro array gene expression analysis was performed, using Phalanx human gene chip containing 45,000 gene probes of 36,000 unique human genes. SKBR3 and BT474 breast cancer cells were treated with BZL101 for 18 hours and compared with untreated control cells.

The mRNAs that are induced by BZL101 was grouped into functional groups. Only RNAs induced at higher that 2.5 fold were considered. Among these genes there is only one that is difficult to assign (AMSH-LP).

There are very few functions that are affected by BZL, and they are:
Apoptosis
Cytokines with proliferative effects
NF kappa B pathway
Oxidative stress
DNA damage response
Cell adhesion There are obviously overlaps between these groups. Many of cytokines could go into NFkB pathway group. Virtually all oxidative stress responders could also go into NFkB pathway group because they are induced by transcription factor NRF2 with the involvement of NFkB. A number of genes in different groups are induced by TNF. DNA damage responders could go into oxidative stress group because they are induced by oxidative DNA damage.

The oxidative stress responders have links to the glycolytic pathway and DNA damage.
Apoptosis
TNFAIP3=A20 (six fold)
TNFRSF21=death receptor 6 (3 fold)
TNF (4.7 fold)
BBC3=PUMA (2.7 fold in SKbr3)
Cytokines with Proliferative Activities
Chemokine CXCL1(melanoma growth factor); seven-fold
Insulin growth factor like family IGFL1 (five fold)
Cardiotropin-like cytokine NNT-1 or CLC (4.6 fold) twice
Chemokine ligand 2 CCL2=macrophage chemoattractant protein MCP1 (3.3 fold)
Adrenomedullin ADM (2.8 fold in SKbr3 and 1.9 in BT474)
NFkappaB Pathway
a Interleukin 8(4.1 fold)
RelB (3.9 fold)
Sequestosome 1 (3.3 fold in SKbr3 and 2 fold in BT474)
Cell Adhesion
ICAM1 (4.3 fold)
Cadherin 5=Vascular endothelim (VE) cadherin (3.3 fold)
PLAUR=uPAR (3 fold)
DNA Damage Response
TIPARP (3 fold)
ATF3 (induced in both cell lines, stronger in BT474)
GADD45A
Oxidative Stress Response
Pregnancy-induced growth inhibitor OKL38 (4.3 fold in SKBr3 and 2.3 fold in BT474)
Glutamate cysteine ligase modifier subunit GCLM (about threefold in both SKBr3 and BT474)
Heme oxygenase (11 fold in SKBrs)
Cystathionine-beta-synthase (2.9 fold in SKBr3)
Other Groups
Associated molecule with the SH3 domain of STAM (AMSH) kike (2.8 fold in SKBr3)

A micro array gene expression chip containing 225 unique genes, 112 up regulated and 113 down-regulated for the diagnosis of patients with adenocarcinoma to test eligibility for treatment with BZL101, an extract of *Scutellaria barbata*. Tumors Expressing Genes, Up or Down Regulated, within the Common Paths Affected by BZL101 will be Eligible for BZL101 Treatment. These Tumors should Show Dependency or Damage in their Apoptosis, Cytokines with Proliferative Effects, NF Kappa B Pathway, Oxidative Stress, DNA Damage Response and Cell Adhesion Associated Genes.

TABLE 1

Genes up-reguated in response to BZL101 treatment in SKBr3 cells.

| Entrez Gene Description | Functional annotation | Entrez Gene Name | Average fold upregulation | Entrez Gene ID |
|---|---|---|---|---|
| cytochrome P450, family 1, subfamily A, polypeptide 1 | Xenobiotic response | CYP1A1 | 43.9 | 1543 |
| heme oxygenase (decycling) 1 | Oxidative response/NFkB pathway | HMOX1 | 10.9 | 3162 |
| similar to Epigen protein | | LOC255324 | 9.0 | 255324 |
| chemokine (C-X-C motif) ligand 1 (melanoma growth stimulating activity, alpha) | NFkB pathway | CXCL1 | 7.3 | 2919 |
| cytochrome P450, family 1, subfamily B, polypeptide 1 | Xenobiotic response | CYP1B1 | 6.8 | 1545 |
| hypothetical gene supported by AF086204 | | LOC440449 | 6.2 | 440449 |
| tumor necrosis factor, alpha-induced protein 3 | Oxidative/NFkB pathway/Cell death | TNFAIP3 | 6.1 | 7128 |
| insulin growth factor-like family member 1 | NFkB pathway | IGFL1 | 5.2 | 374918 |
| neuronal PAS domain protein 2 | | NPAS2 | 5.2 | 4862 |

TABLE 1-continued

Genes up-regulated in response to BZL101 treatment in SKBr3 cells.

| Entrez Gene Description | Functional annotation | Entrez Gene Name | Average fold upregulation | Entrez Gene ID |
|---|---|---|---|---|
| tumor necrosis factor (TNF superfamily, member 2) | NFkB pathway/Cell death | TNF | 4.7 | 7124 |
| cardiotrophin-like cytokine | NFkB pathway | CLC | 4.6 | 23529 |
| baculoviral IAP repeat-containing 3 | NFkB pathway/Cell death | BIRC3 | 4.6 | 330 |
| pregnancy-induced growth inhibitor | Oxidative response | OKL38 | 4.3 | 29948 |
| intercellular adhesion molecule 1 (CD54), human rhinovirus receptor | NFkB pathway | ICAM1 | 4.3 | 3383 |
| interleukin 8 | NFkB pathway | IL8 | 4.1 | 3576 |
| v-rel reticuloendotheliosis viral oncogene homolog B, nuclear factor of kappa light polypeptide gene enhancer in B-cells 3 (avian) | NFkB pathway | RELB | 3.9 | 5971 |
| chemokine (C-C motif) ligand 2 | NFkB pathway/Cell death | CCL2 | 3.4 | 6347 |
| sequestosome 1 | NFkB pathway/Cell death | SQSTM1 | 3.3 | 8878 |
| cardiotrophin-like cytokine | NFkB pathway/Cell death | CLC | 3.3 | 23529 |
| cadherin 5, type 2, VE-cadherin (vascular epithelium) | | CDH5 | 3.3 | 1003 |
| TCDD-inducible poly(ADP-ribose) polymerase | Oxidative/DNA damage response/NFkB pathway | TIPARP | 3.1 | 25976 |
| chemokine (C-C motif) ligand 2 | NFkB pathway | CCL2 | 3.0 | 6347 |
| plasminogen activator, urokinase receptor | NFkB pathway | PLAUR | 3.0 | 5329 |
| tumor necrosis factor receptor superfamily, member 21 | NFkB pathway/Cell death | TNFRSF21 | 3.0 | 27242 |
| glutamate-cysteine ligase, modifier subunit | Oxidative response/NFkB pathway | GCLM | 2.9 | 2730 |
| cystathionine-beta-synthase | Oxidative response/NFkB pathway | CBS | 2.9 | 875 |
| ring finger protein 24 | | RNF24 | 2.8 | 11237 |
| associated molecule with the SH3 domain of STAM (AMSH) like protein | | AMSH-LP | 2.8 | 57559 |
| adrenomedullin | | ADM | 2.8 | 133 |
| heat shock 70 kDa protein 6 (HSP70B') | Xenobiotic response | HSPA6 | 2.8 | 3310 |
| BCL2 binding component 3 | NFkB pathway/Cell death | BBC3 | 2.7 | 27113 |
| elongation factor, RNA polymerase II, 2 | | ELL2 | 2.6 | 22936 |
| activating transcription factor 3 | Oxidative/DNA damage response/NFkB pathway | ATF3 | 2.6 | 467 |
| chromosome 20 open reading frame 139 | | C20orf139 | 2.5 | 140809 |
| growth arrest and DNA-damage-inducible, alpha | DNA damage response/Cell death/NFkB pathway | GADD45A | 2.5 | 1647 |
| spermidine/spermine N1-acetyltransferase | | SAT | 2.5 | 6303 |
| solute carrier organic anion transporter family, member 4A1 | | SLCO4A1 | 2.4 | 28231 |
| NK3 transcription factor related, locus 1 (*Drosophila*) | | NKX3-1 | 2.4 | 4824 |
| chemokine (C-C motif) ligand 11 | NFkB pathway/Cell death | CCL11 | 2.4 | 6356 |
| maltase-glucoamylase (alpha-glucosidase) | | MGAM | 2.3 | 8972 |
| RAS, dexamethasone-induced 1 | NFkB pathway | RASD1 | 2.3 | 51655 |
| zinc finger, SWIM domain containing 4 | | ZSWIM4 | 2.3 | 65249 |

TABLE 1-continued

Genes up-regulated in response to BZL101 treatment in SKBr3 cells.

| Entrez Gene Description | Functional annotation | Entrez Gene Name | Average fold upregulation | Entrez Gene ID |
|---|---|---|---|---|
| nuclear factor of kappa light polypeptide gene enhancer in B-cells inhibitor, epsilon | NFkB pathway/Cell death | NFKBIE | 2.3 | 4794 |
| p53-regulated apoptosis-inducing protein 1 | Cell death | P53AIP1 | 2.3 | 63970 |
| NEDD9 interacting protein with calponin homology and LIM domains | | NICAL | 2.3 | 64780 |
| CCR4 carbon catabolite repression 4-like (*S. cerevisiae*) | | CCRN4L | 2.3 | 25819 |
| Rap guanine nucleotide exchange factor (GEF)-like 1 | | RAPGEFL1 | 2.2 | 51195 |
| carbonic anhydrase VIII | | CA8 | 2.2 | 767 |
| arrestin domain containing 2 | | ARRDC2 | 2.2 | 27106 |
| nasal embryonic LHRH factor | | NELF | 2.2 | 26012 |
| pleckstrin homology-like domain, family A, member 2 | | PHLDA2 | 2.2 | 7262 |
| claudin 1 | | CLDN1 | 2.2 | 9076 |
| immediate early response 5 | | IER5 | 2.2 | 51278 |
| phosphoinositide-3-kinase, catalytic, delta polypeptide | | PIK3CD | 2.2 | 5293 |
| pannexin 1 | | PANX1 | 2.2 | 24145 |
| chemokine (C-X-C motif) ligand 16 | NFkB pathway/Cell death | CXCL16 | 2.2 | 58191 |
| keratin 5 (epidermolysis bullosa simplex, Dowling-Meara/Kobner/Weber-Cockayne types) | | KRT5 | 2.1 | 3852 |
| myeloma overexpressed gene (in a subset of t(11;14) positive multiple myelomas) | | MYEOV | 2.1 | 26579 |
| small nuclear RNA activating complex, polypeptide 4, 190 kDa | | SNAPC4 | 2.1 | 6621 |
| estrogen receptor binding protein | | ERBP | 2.1 | 30836 |
| ubiquitin-conjugating enzyme E2E 2 (UBC4/5 homolog, yeast) | | UBE2E2 | 2.1 | 7325 |
| zinc finger protein 36, C3H type, homolog (mouse) | | ZFP36 | 2.1 | 7538 |
| polo-like kinase 2 (*Drosophila*) | | PLK2 | 2.1 | 10769 |
| sulfide quinone reductase-like (yeast) | | SQRDL | 2.1 | 58472 |
| solute carrier family 2 (facilitated glucose transporter), member 6 | | SLC2A6 | 2.1 | 11182 |
| tubulin, beta 6 | | TUBB6 | 2.0 | 84617 |
| RNA terminal phosphate cyclase-like 1 | | RCL1 | 2.0 | 10171 |
| ATP-binding cassette, sub-family C (CFTR/MRP), member 2 | | ABCC2 | 2.0 | 1244 |
| leucine rich repeat and fibronectin type III domain containing 1 | | LRFN1 | 2.0 | 57622 |
| pellino 3 alpha | | MGC35521 | 2.0 | 246330 |
| interferon regulatory factor 1 | NFkB pathway | IRF1 | 2.0 | 3659 |
| spermidine/spermine N1-acetyltransferase | | SAT | 2.0 | 6303 |
| optineurin | | OPTN | 2.0 | 10133 |
| sestrin 2 | Cell cycle regulation | SESN2 | 2.0 | 83667 |
| tubulin, beta 2 | | TUBB2 | 2.0 | 7280 |
| cytoplasmic polyadenylation element binding protein 2 | | CPEB2 | 1.9 | 132864 |
| fatty acid desaturase 3 | | FADS3 | 1.9 | 3995 |
| nuclear receptor coactivator 7 | | NCOA7 | 1.9 | 135112 |
| TNF receptor-associated factor 3 | NFkB pathway/Cell death | TRAF3 | 1.9 | 7187 |
| tripartite motif-containing 21 | | TRIM21 | 1.9 | 6737 |
| early growth response 1 | | EGR1 | 1.9 | 1958 |
| MOB1, Mps One Binder kinase activator-like 2C (yeast) | | MOBKL2C | 1.9 | 148932 |

TABLE 1-continued

Genes up-regulated in response to BZL101 treatment in SKBr3 cells.

| Entrez Gene Description | Functional annotation | Entrez Gene Name | Average fold upregulation | Entrez Gene ID |
|---|---|---|---|---|
| progressive external ophthalmoplegia 1 | | PEO1 | 1.9 | 56652 |
| DEAD (Asp-Glu-Ala-Asp) box polypeptide 31 | | DDX31 | 1.9 | 64794 |
| thioredoxin reductase 1 | Oxidative response | TXNRD1 | 1.9 | 7296 |
| endothelin 1 | NFkB pathway | EDN1 | 1.9 | 1906 |
| TIGA1 | | TIGA1 | 1.9 | 114915 |
| transmembrane 4 superfamily member 14 | | TM4SF14 | 1.9 | 81619 |
| axin 1 | | AXIN1 | 1.9 | 8312 |
| monocyte to macrophage differentiation-associated | Cell death | MMD | 1.9 | 23531 |
| CCAAT/enhancer binding protein (C/EBP), delta | | CEBPD | 1.9 | 1052 |
| leukotriene B4 receptor | | LTB4R | 1.9 | 1241 |
| pre-B-cell colony enhancing factor 1 | NFkB pathway | PBEF1 | 1.8 | 10135 |
| WD repeat domain 3 | | WDR3 | 1.8 | 10885 |
| NIMA (never in mitosis gene a)-related kinase 6 | NFkB pathway | NEK6 | 1.8 | 10783 |
| pleckstrin homology domain containing, family F (with FYVE domain) member 1 | | PLEKHF1 | 1.8 | 79156 |
| pleckstrin 2 | | PLEK2 | 1.8 | 26499 |
| FKSG27 protein | | FKSG27 | 1.8 | 126298 |
| coronin, actin binding protein, 1C | | CORO1C | 1.8 | 23603 |
| snail homolog 1 (*Drosophila*) | | SNAI1 | 1.8 | 6615 |
| MOB1, Mps One Binder kinase activator-like 1A (yeast) | | MOBKL1A | 1.8 | 92597 |
| cytochrome P450, family 27, subfamily B, polypeptide 1 | Xenobiotic response | CYP27B1 | 1.8 | 1594 |
| pseudouridylate synthase 1 | | PUS1 | 1.8 | 80324 |
| nuclear factor of kappa light polypeptide gene enhancer in B-cells inhibitor, beta | NFkB pathway | NFKBIB | 1.8 | 4793 |
| ubiquitin-conjugating enzyme E2E 1 (UBC4/5 homolog, yeast) | | UBE2E1 | 1.8 | 7324 |
| minor histocompatibility antigen HA-1 | | HA-1 | 1.8 | 23526 |
| PWP2 periodic tryptophan protein homolog (yeast) | | PWP2H | 1.7 | 5822 |
| tyrosylprotein sulfotransferase 1 | | TPST1 | 1.7 | 8460 |
| cyclin-dependent kinase inhibitor 1A (p21, Cip1) | NFkB pathway/Cell death | CDKN1A | 1.7 | 1026 |
| zinc finger protein 529 | | ZNF529 | 1.7 | 57711 |

TABLE 2

Genes down-regulated in response to BZL101 treatment in SKBr3 cells.

| Entrez Gene Description | Functional annotataion | Entrez Gene Name | Ave Fold downregulation | Entrez_Gene_ID |
|---|---|---|---|---|
| inhibitor of DNA binding 1, dominant negative helix-loop-helix protein | NFβB pathway/Cell cycle regulation | ID1 | 5.0 | 3397 |
| cyclin-dependent kinase inhibitor 2C (p18, inhibits CDK4) | Cell cycle regulation | CDKN2C | 3.3 | 1031 |
| zinc finger protein 339 | | ZNF339 | 2.9 | 58495 |
| peroxiredoxin 3 | Oxidative damage/NFβB pathway | PRDX3 | 2.9 | 10935 |
| KIAA0644 gene product | | KIAA0644 | 2.8 | 9865 |
| eyes absent homolog 2 (*Drosophila*) | | EYA2 | 2.6 | 2139 |

TABLE 2-continued

Genes down-reguated in response to BZL101 treatment in SKBr3 cells.

| Entrez Gene Description | Functional annotataion | Entrez Gene Name | Ave Fold downregulation | Entrez_Gene_ID |
|---|---|---|---|---|
| SMAD, mothers against DPP homolog 6 (*Drosophila*) | Cell cycle regulation | SMAD6 | 2.6 | 4091 |
| ecotropic viral integration site 1 | | EVI1 | 2.6 | 2122 |
| ras homolog gene family, member U | | RHOU | 2.6 | 58480 |
| gap junction protein, alpha 5, 40 kDa (connexin 40) | | GJA5 | 2.6 | 2702 |
| tensin | | TNS | 2.5 | 7145 |
| RAB26, member RAS oncogene family | | RAB26 | 2.5 | 25837 |
| chromosome 15 open reading frame 20 | | C15orf20 | 2.5 | 80119 |
| PTPRF interacting protein, binding protein 2 (liprin beta 2) | | PPFIBP2 | 2.5 | 8495 |
| centrosomal protein 1 | | CEP1 | 2.5 | 11064 |
| antigen identified by monoclonal antibody Ki-67 | Cell cycle regulation | MKI67 | 2.4 | 4288 |
| kinetochore associated 2 | Cell cycle regulation | KNTC2 | 2.4 | 10403 |
| hyaluronan-mediated motility receptor (RHAMM) | Cell adhesion | HMMR | 2.4 | 3161 |
| kinesin family member 20A | | KIF20A | 2.4 | 10112 |
| zinc finger protein 467 | | ZNF467 | 2.4 | 168544 |
| topoisomerase (DNA) II alpha 170 kDa | DNA damage response | TOP2A | 2.3 | 7153 |
| inhibitor of DNA binding 2, dominant negative helix-loop-helix protein | Cell cycle regulation | ID2 | 2.3 | 3398 |
| MAX dimerization protein 3 | Cell cycle regulation | MXD3 | 2.3 | 83463 |
| UDP-N-acetyl-alpha-D-galactosamine:polypeptide N-acetylgalactosaminyltransferase 12 (GalNAc-T12) | | GALNT12 | 2.3 | 79695 |
| transcription factor AP-2 beta (activating enhancer binding protein 2 beta) | | TFAP2B | 2.3 | 7021 |
| centromere protein E, 312 kDa | Cell cycle regulation | CENPE | 2.3 | 1062 |
| cell division cycle associated 3 | Cell cycle regulation | CDCA3 | 2.2 | 83461 |
| sema domain, immunoglobulin domain (Ig), short basic domain, secreted, (semaphorin) 3F | | SEMA3F | 2.2 | 6405 |
| myosin VIIA (Usher syndrome 1B (autosomal recessive, severe)) | | MYO7A | 2.2 | 4647 |
| Rho-related BTB domain containing 3 | | RHOBTB3 | 2.2 | 22836 |
| otoraplin | | OTOR | 2.2 | 56914 |
| centromere protein F, 350/400ka (mitosin) | Cell cycle regulation | CENPF | 2.2 | 1063 |
| kinetochore protein Spc25 | Cell cycle regulation | Spc25 | 2.2 | 57405 |
| CDC42 effector protein (Rho GTPase binding) 4 | Cell cycle regulation | CDC42EP4 | 2.2 | 23580 |
| baculoviral IAP repeat-containing 5 (survivin) | Cell cycle regulation/Cell death | BIRC5 | 2.2 | 332 |
| ankyrin 3, node of Ranvier (ankyrin G) | | ANK3 | 2.2 | 288 |
| solute carrier family 40 (iron-regulated transporter), member 1 | | SLC40A1 | 2.2 | 30061 |
| peroxisomal biogenesis factor 11A | | PEX11A | 2.2 | 8800 |
| Nedd4 binding protein 3 | | N4BP3 | 2.1 | 23138 |
| SLIT-ROBO Rho GTPase activating protein 2 | | SRGAP2 | 2.1 | 23380 |
| cytochrome P450 4Z2 pseudogene | | CYP4Z2P | 2.1 | 163720 |
| X-box binding protein 1 | ER stress | XBP1 | 2.1 | 7494 |
| ectodermal-neural cortex (with BTB-like domain) | | ENC1 | 2.1 | 8507 |

TABLE 2-continued

Genes down-reguated in response to BZL101 treatment in SKBr3 cells.

| Entrez Gene Description | Functional annotataion | Entrez Gene Name | Ave Fold downregulation | Entrez_Gene_ID |
|---|---|---|---|---|
| FGD1 family, member 3 | | FGD3 | 2.1 | 89846 |
| centromere protein A, 17 kDa | Cell cycle regulation | CENPA | 2.1 | 1058 |
| high-mobility group box 2 | DNA damage response | HMGB2 | 2.1 | 3148 |
| dedicator of cytokinesis 11 | | DOCK11 | 2.1 | 139818 |
| transducer of ERBB2, 1 | | TOB1 | 2.1 | 10140 |
| sortilin-related receptor, L(DLR class) A repeats-containing | | SORL1 | 2.1 | 6653 |
| HRAS-like suppressor 3 | Cell cycle regulation | HRASLS3 | 2.1 | 11145 |
| epithelial cell transforming sequence 2 oncogene | NFβB pathway | ECT2 | 2.1 | 1894 |
| single-stranded DNA binding protein 2 | | SSBP2 | 2.1 | 23635 |
| nuclear factor I/A | | NFIA | 2.1 | 4774 |
| delta sleep inducing peptide, immunoreactor | | DSIPI | 2.1 | 1831 |
| phosphodiesterase 8B | | PDE8B | 2.1 | 8622 |
| BUB1 budding uninhibited by benzimidazoles 1 homolog beta (yeast) | Cell cycle regulation | BUB1B | 2.1 | 701 |
| SWI/SNF related, matrix associated, actin dependent regulator of chromatin, subfamily a, member 2 | | SMARCA2 | 2.1 | 6595 |
| zinc finger protein 552 | | ZNF552 | 2.0 | 79818 |
| polo-like kinase 1 (*Drosophila*) | Cell cycle regulation | PLK1 | 2.0 | 5347 |
| phosphoglucomutase 1 | | PGM1 | 2.0 | 5236 |
| erythrocyte membrane protein band 4.1-like 1 | | EPB41L1 | 2.0 | 2036 |
| thioredoxin-related transmembrane protein 2 | | TMX2 | 2.0 | 51075 |
| kinesin family member 14 | | KIF14 | 2.0 | 9928 |
| LPS-responsive vesicle trafficking, beach and anchor containing | | LRBA | 2.0 | 987 |
| dehydrogenase/reductase (SDR family) member 3 | | DHRS3 | 2.0 | 9249 |
| pleckstrin homology domain containing, family K member 1 | | PLEKHK1 | 1.9 | 219790 |
| succinate-CoA ligase, GDP-forming, alpha subunit | | SUCLG1 | 1.9 | 8802 |
| epithelial protein lost in neoplasm beta | | EPLIN | 1.9 | 51474 |
| histamine receptor H1 | | HRH1 | 1.9 | 3269 |
| histone 1, H2ac | | HIST1H2AC | 1.9 | 8334 |
| cingulin | | CGN | 1.9 | 57530 |
| SAM and SH3 domain containing 1 | Cell cycle regulation | SASH1 | 1.9 | 23328 |
| tight junction protein 3 (zona occludens 3) | | TJP3 | 1.9 | 27134 |
| mucin 15 | | MUC15 | 1.9 | 143662 |
| chromosome condensation-related SMC-associated protein 1 | Cell cycle regulation | CNAP1 | 1.9 | 9918 |
| UDP-N-acetyl-alpha-D-galactosamine:polypeptide N-acetylgalactosaminyltransferase 10 (GalNAc-T10) | | GALNT10 | 1.9 | 55568 |
| aurora kinase B | Cell cycle regulation | AURKB | 1.9 | 9212 |
| ATPase, H+ transporting, lysosomal V0 subunit a isoform 4 | | ATP6V0A4 | 1.9 | 50617 |
| G-2 and S-phase expressed 1 | DNA damage/Cell cycle regulation | GTSE1 | 1.9 | 51512 |
| spectrin repeat containing, nuclear envelope 2 | | SYNE2 | 1.9 | 23224 |
| heat shock 60 kDa protein 1 (chaperonin) | | HSPD1 | 1.9 | 3329 |

TABLE 2-continued

Genes down-reguated in response to BZL101 treatment in SKBr3 cells.

| Entrez Gene Description | Functional annotataion | Entrez Gene Name | Ave Fold downregulation | Entrez_Gene_ID |
|---|---|---|---|---|
| nebulette | | NEBL | 1.9 | 10529 |
| protein kinase C, delta | | PRKCD | 1.9 | 5580 |
| neurexin 3 | Cell adhesion | NRXN3 | 1.9 | 9369 |
| transglutaminase 3 (E polypeptide, protein-glutamine-gamma-glutamyltransferase) | | TGM3 | 1.9 | 7053 |
| mesoderm posterior 1 | | MESP1 | 1.9 | 55897 |
| hexosaminidase B (beta polypeptide) | | HEXB | 1.9 | 3074 |
| RWD domain containing 2 | | RWDD2 | 1.9 | 112611 |
| fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | | FGFR2 | 1.9 | 2263 |
| Down syndrome critical region gene 1 | | DSCR1 | 1.9 | 1827 |
| cyclin A2 | DNA damage/Cell cycle regulation | CCNA2 | 1.8 | 890 |
| calcyphosine | | CAPS | 1.8 | 828 |
| methylcrotonoyl-Coenzyme A carboxylase 1 (alpha) | | MCCC1 | 1.8 | 56922 |
| keratin 15 | | KRT15 | 1.8 | 3866 |
| GPAA1P anchor attachment protein 1 homolog (yeast) | | GPAA1 | 1.8 | 8733 |
| actin related protein 2/3 complex, subunit 5, 16 kDa | Cell adhesion | ARPC5 | 1.8 | 10092 |
| ATP-binding cassette, sub-family A (ABC1), member 1 | | ABCA1 | 1.8 | 19 |
| epidermal growth factor receptor pathway substrate 8 | | EPS8 | 1.8 | 2059 |
| HMBA-inducible | Cell cycle regulation | HIS1 | 1.8 | 10614 |
| transcription elongation factor A (SII)-like 1 | | TCEAL1 | 1.8 | 9338 |
| breast carcinoma amplified sequence 1 | | BCAS1 | 1.8 | 8537 |
| distal-less homeobox 4 | | DLX4 | 1.8 | 1748 |
| protein phosphatase 1H (PP2C domain containing) | | PPM1H | 1.8 | 57460 |
| heat shock 70 kDa protein 8 | | HSPA8 | 1.8 | 3312 |
| Kruppel-like factor 13 | | KLF13 | 1.8 | 51621 |
| 15 kDa selenoprotein | | 15.九月 | 1.7 | 9403 |
| eukaryotic translation initiation factor 4E binding protein 2 | | EIF4EBP2 | 1.7 | 1979 |
| branched chain keto acid dehydrogenase E1, alpha polypeptide (maple syrup urine disease) | | BCKDHA | 1.7 | 593 |
| eukaryotic translation initiation factor 3, subunit 6 interacting protein | | EIF3S6IP | 1.7 | 51386 |
| zinc fingers and homeoboxes 2 | | ZHX2 | 1.7 | 22882 |
| SUMO-1 activating enzyme subunit 1 | | SAE1 | 1.7 | 10055 |

Example 3

Methods of Diagnosing and Treating Humans with Breast Cancer Using 8-oxoguanine Biomarker A group of up to thirty patients who have and who do not have breast cancer will be tested for the presence of 8-oxoguanine. All patients will be at least 18 years of age. Patients representing an individual having breast cancer will present both histological confirmation of breast cancer as well as clinical evidence of metastatic involvement. The testing will be done in a double blind fashion. Patients who enter into the test will have a blood sample drawn. The blood will be tested for presence of 8-oxoguanine biomarker by reacting the blood with a diagnostic tool that detects the presence of 8-oxoguanine. For each patient, a level of 8-oxoguanine will be output to a display indicating the level of 8-oxoguanine for that specific patient. The patient's level of 8-oxoguanine will then be compared to a predetermined level of 8-oxoguanine as determined from sampling a population of 50 individuals who have not been diagnosed with breast cancer, or normal individuals. The predetermined threshold level will include the average 8-oxoguanine level for the group of normal individuals plus and minus the standard deviation for the population. Patients in whom a level of 8-oxoguanine biomarker is detected to be above the threshold level will then be singled out as potentially having breast cancer. These patients will then be compared to any histological data present for that patient. Once it is confirmed that the patient does in fact have breast cancer, the patient will be administered 350 ml (equivalent to 12 grams dry soluble extract of 180 grams of BZL) BZL101 extract per day. These patients will then be monitored by having blood drawn at specified intervals, preferably once a month to detect levels of 8-oxoguanine in the blood. BZL101 will continue to be administered to the patient until an adverse event more severe than a grade I or grade II adverse event occurs, the patient self-elects to forego treatment or the disease progresses to a clinically significant degree. Throughout treatment, periodically (e.g. once per week), the level of 8-oxoguanine biomarker will be detected to track the progress of treatment.

Example 3

Methods of Diagnosing and Treating Humans with Breast Cancer Using Lactate Dehydrogenase and a 8-oxoguanine Biomarkers A group of thirty patients who have and who do not have breast cancer will be tested for the presence of lactate dehydrogenase and 8-oxoguanine biomarkers. All patients were at least 18 years of age. Patients representing an individual having breast cancer will present both histological confirmation of breast cancer as well as clinical evidence of metastatic involvement. The testing will be done in a double blind fashion. Patients who enter into the test will submit a urine sample. The urine sample will be tested for presence of lactate dehydrogenase and 8-oxoguanine biomarkers by reacting the urine with a diagnostic tool that detects the presence of both the lactate dehydrogenase and the 8-oxoguanine biomarkers. For each patient, a level of lactate dehydrogenase and 8-oxoguanine will be output to a display indicating the levels of lactate dehydrogenase and 8-oxoguanine for that specific patient. The patient's level of lactate dehydrogenase and 8-oxoguanine will then be compared to a predetermined levels of lactate dehydrogenase and 8-oxoguanine as determined from sampling a population of 50 individuals who have not been diagnosed with breast cancer, or normal individuals. The predetermined threshold levels will include the average lactate dehydrogenase and 8-oxoguanine levels for the group of normal individuals plus and minus the standard deviation for the population. Patients in whom a level of lactate dehydrogenase and 8-oxoguanine biomarker is detected to be above the threshold level will then be singled out as potentially having breast cancer. These patients will then be compared to any histological data present for that patient Once it is confirmed that the patient does in fact have breast cancer, the patient will be administered a therapeutic amount of an extract of BZL101 in order to treat the cancer.

CONCLUSION

The herbal extract BZL101, its uses for the inhibition of solid tumor cancer cells and the treatment of such cancers in patients are described herein. Although certain embodiments and examples have been used to describe the present invention, it will be apparent to those skilled in the art that changes to the embodiments and examples may be made without departing from the scope and spirit of this invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for the treatment of breast cancer, comprising:
   (a) contacting a portion of a biological sample comprising breast tumor cells obtained from a patient with a composition comprising an extract of *Scutellaria barbata* D. Don to produce a treated sample;
   (b) detecting a level of DNA oxidation in the treated sample and in an untreated sample comprising breast tumor cells obtained from the patient;
   (c) if the level of DNA oxidation in the treated sample meets or exceeds a predetermined threshold, which is three times the level of oxidation in the untreated sample, administering to the patient an effective amount of the composition comprising an extract of *Scutellaria barbata* D. Don; and,
   (d) if the level of marker of DNA oxidation in the sample is below said predetermined threshold, administering an alternative treatment to the patient.

2. The method of claim 1, comprising detecting the level of a marker of DNA oxidation.

3. The method of claim 1, wherein the marker of DNA oxidation is 8-oxoguanine.

4. A method of deciding whether to continue anti-breast cancer chemotherapeutic treatment with a composition comprising an extract of *Scutellaria barbata* D. Don, comprising:
   (a) obtaining a biological sample comprising breast tumor cells from a patient undergoing anti-breast cancer treatment with a composition comprising an extract of *Scutellaria barbata* D. Don;
   (b) contacting a portion of the biological sample with a composition comprising an extract of *Scutellaria barbata* D. Don to produce a treated sample;
   (c) detecting a level of a marker of DNA oxidation in the treated sample and in an untreated sample comprising breast tumor cells obtained from the patient;
   (d) if the level of marker of DNA oxidation in the treated sample exceeds a predetermined threshold, which is three times the level of DNA oxidation in the untreated sample, continuing to administer to the patient an effective amount of an extract of *Scutellaria barbata* D. Don; and
   (e) if the level of marker of DNA oxidation in the treated sample is below the predetermined threshold, discontinuing treatment with the composition comprising an extract of *Scutellaria barbata* D. Don and/or administering an alternative treatment to the patient.

5. The method of claim 4, wherein the marker of DNA oxidation is 8-oxoguanine or lactate.

* * * * *

SEQUENCE LISTING

```
<160> NUMBER OF SEQ ID NOS: 176

<210> SEQ ID NO 1
<211> LENGTH: 100
<212> TYPE: DNA
<213> ORGANISM: Homo sapiens

<400> SEQUENCE: 1
gattattagt ataaaagggg agataggtag gagtagcgtg gtaagggcga tgagtgtggg      60
gaggaatggg gtgggttttg tatgttcaaa ctgtcatttt                           100

<210> SEQ ID NO 2
<211> LENGTH: 87
<212> TYPE: DNA
<213> ORGANISM: Homo sapiens

<400> SEQUENCE: 2
gagaaaatat ccttgactgg gtatgcattt tagcaaagca aagagtgatt ctcaggcaat      60
caagttgaaa ccaactacac agtgttt                                         87
```

```
<210> SEQ ID NO 3
<211> LENGTH: 122
<212> TYPE: DNA
<213> ORGANISM: Homo sapiens

<400> SEQUENCE: 3
attccagctg tactggcctc tttgctgttg catcggctgt ttcctctgcc tcatactctt      60
ccccaggcat ctgcatggct aagtccttca cctccttcaa gtgtttgctc aaatgtcacc     120
tt                                                                    122

<210> SEQ ID NO 4
<211> LENGTH: 91
<212> TYPE: DNA
<213> ORGANISM: Homo sapiens

<400> SEQUENCE: 4
ggtaagggag ggatcgttga cctcgtctgt tatgtaaagg atgcgtaggg atgggagggc      60
gatgaggact aggatgatgg cgggcaggat a                                     91

<210> SEQ ID NO 5
<211> LENGTH: 131
<212> TYPE: DNA
<213> ORGANISM: Homo sapiens

<400> SEQUENCE: 5
gaattcgttc ggaaatatcc cctgacctga agttctggtt tccctgcacc ccagaccgga      60
cattttcttt tgtccttatc tcagtaagta ctgagtattg tgagaggaac aagtgagtct     120
cttttgtttc t                                                          131

<210> SEQ ID NO 6
<211> LENGTH: 73
<212> TYPE: DNA
<213> ORGANISM: Homo sapiens

<400> SEQUENCE: 6
attgtaaata gggattcttt gtctagggtt tggggtttaa gcctgttaat ttagtagaac      60
ctcatttttc tct                                                         73

<210> SEQ ID NO 7
<211> LENGTH: 268
<212> TYPE: DNA
<213> ORGANISM: Homo sapiens

<400> SEQUENCE: 7
cttagctgtg ctgtaggatg ggacctgggc ttctgtgttg aggtaacttc tattgtgagg      60
aagaagaggg cgaaattgtg tggcatgatt ttttgtatg aaaagtgaag ggcctattct     120
taattttgaa caactgcctg ctttctgatt tactttgat ccggatttgt tggattcctc     180
actgtactgt gtaggttgag cttacaaagg tgtggatttt gagcagtgcg attacccct     240 ttcagatttg gggttgctgt tgtttttg                                        268

<210> SEQ ID NO 8
<211> LENGTH: 314
<212> TYPE: DNA
<213> ORGANISM: Homo sapiens

<400> SEQUENCE: 8
ccctgtgtgg ccggctctta ggtggttccg ataagacaca atgcagatgc aactgggggg      60
ccctgcatcc ggctagctta cgtagccaaa cgggatttaa cgaggaagca aacgtgttgt     120
```

-continued

```
ctaatgttcc ctgtgtcaaa tgattcactc cgcccaggaa agggatgggg tcctggagga      180
agatctgcaa gtcacaagtt cccatcaatc actcgataat ataagagata ggagttttaa      240
acataactag tatcaggcaa ctgctatcac atccacaccc tgcagctcat tatgttaaat      300
agtcccttcg ggga                                                        314
```

<210> SEQ ID NO 9
<211> LENGTH: 197
<212> TYPE: DNA
<213> ORGANISM: Homo sapiens

<400> SEQUENCE: 9

```
gcagactgca gcgttctgag aaacatcttt gtgatgtttg tattcaggac acagagttga       60
acattcccta tcatagagca ggttgggatc actccttttg tagtatctgg aagtggacat      120
ttggagcgct ttcaggccta tgttgaaaaa agaaaaatct cccataaca actagacaga       180 agcattctca gaaactt                                                    197
```

<210> SEQ ID NO 10
<211> LENGTH: 467
<212> TYPE: DNA
<213> ORGANISM: Homo sapiens

<400> SEQUENCE: 10

```
cctgattagg tcaggctcac catgatactc tcccttttga tcaatgtgaa gtcagctgac       60
tggggacgtt acttgtaaca tctgcaaaat cccttcactt tgccatata caacataatc      120 acaggagtga tatcccatta cctttgccat agcctattgg ttagaatcaa attacgagtt      180 cccccctacca cttgaagact tacctttct tataagataa atcaatacat atgacaagag      240
ttagagtcgg ttttgaagga taagggtgat tcttttcttt tttttttttt ttttttgag      300 gtggaatctc gctctgtcgc ccaggctgga gtgcagtggc gggatctcag ctcactgcaa      360
gctccgcctc ctgggttcac gccatttca tgcctcagcc tcccgagtag ctgggactac      420
aggcacccgc caccacgcct ggctaatttt ttgtatttgg agtaggg                   467
```

<210> SEQ ID NO 11
<211> LENGTH: 177
<212> TYPE: DNA
<213> ORGANISM: Homo sapiens

<400> SEQUENCE: 11

```
ttccctaaat cctgagacag aaaaatggaa agaaatgatt tcacagtagg tagaaggaat       60
tccattagca cagcgcaatt aaaaaattgt ttcacgctgt gtaggcacaa atctgtccat      120
tagcacagcg gcaattaaaa aaattgtttt ccagctgtgt aggcacaaaa tctgttt        177
```

<210> SEQ ID NO 12
<211> LENGTH: 187
<212> TYPE: DNA
<213> ORGANISM: Homo sapiens

<400> SEQUENCE: 12

```
tcctctttcc ctgttcggac tgcagtctca gtagttagga gcactaggta gggtccttcc       60
aagctagtac gagtttccct tccttccacc ctttgatgag gacgtggtct ccaggctgat      120
gctgatgtgc tgaaaactcc aggggcagcg cctgtgctag gagaccttct gtcttaaggg      180
aagagaa                                                               187
```

```
<210> SEQ ID NO 13
<211> LENGTH: 80
<212> TYPE: DNA
<213> ORGANISM: Homo sapiens

<400> SEQUENCE: 13
ttgcatttac acaaagcagt tctagatgga agggaggaga tagaccccac ctctcaatgg    60
agtgtccctc ttcggtggcc                                               80

<210> SEQ ID NO 14
<211> LENGTH: 369
<212> TYPE: DNA
<213> ORGANISM: Homo sapiens

<400> SEQUENCE: 14
gttggactac gtggcttctg agacccttcc agagctaaca ttttatgatc tatgattaag    60
actgagatga cattgttcag cccactgtcc agagggtgac ccaccaactt tcataaaaac   120
aatcatcatt aacctatgtt aattggtcaa taaaacatca caattttata gcatgaaacc   180
tgagacctgc tgagatcaac actactggta agccaagtgg aagttcagcc ttagaaacga   240
aattgctgac tagtaacccc agtgtcatat tagtcaaagt gacatagact caaacttatt   300
ctggttgaaa tgaaaacaac tgatggagaa actgagtggc acataaaaca agcttggggt   360
tggaagaac                                                          369

<210> SEQ ID NO 15
<211> LENGTH: 198
<212> TYPE: DNA
<213> ORGANISM: Homo sapiens

<400> SEQUENCE: 15
tcgatggaaa ggaaatgaga ggttctgaga ggcgggctag tggcttgtac tatagcatag    60
cctgcctttg ctggtgtgtg gcgattaggc ctggtgaaac tgccatcaat aaatcaagag   120
tgatcagggt gaggaatagg aaagaaggaa atacagggaa atggggtgaa tatcaggtgg   180
atcagagaga tacagtcg                                                198

<210> SEQ ID NO 16
<211> LENGTH: 381
<212> TYPE: DNA
<213> ORGANISM: Homo sapiens

<400> SEQUENCE: 16
agctccttct ctgtgcttct tattctatac actgtcaggg cacaagtcat gtatgaccag    60
ttccttgtct tcaagaagct tatattcaga ttggaaaagt aaagttaaac tagatattaa   120
attgttatgg tctaaactgt gcactccagc ctgggtgaca gagtgagact ctgtttattt   180 cttttttattt ttttgggggg tacagagtct caggctggag tgcagtggca cgatcttggc   240
tcactgcaac ctctgcctcc caggttcaag caattctcct gcctcagcct cccgagttgc   300
taggattata agtggtagct aggattacag ctaccatgcc accacgcctc gctaattttt   360 gtattttgg tagagacggg g                                             381

<210> SEQ ID NO 17
<211> LENGTH: 352
<212> TYPE: DNA
<213> ORGANISM: Homo sapiens

<400> SEQUENCE: 17
agtaactctt gcctaaattc taatgcaatt tcctaatgga tgtccttcct ataactttgt    60
```

```
cccattataa ccctttcctc tacgactcac ccaaaagtat cttttttaata agaaaaatag     120 atgatgttta ataccttcga gtggcttgcc atttaggtac ctaaaacacg acgaattctc     180
tagatatcaa gcttgaattc gttatgtatc tttttggtgg acacaattca acaaacgtga     240
accatgtgcc aacatgagt  ggagaagcca cctatgcca  ggctccaaac aacaatctag    300
gaagatgggc cccaggatat aagatgctat gaacacagaa acaaatagg ac             352
```

<210> SEQ ID NO 18
<211> LENGTH: 224
<212> TYPE: DNA
<213> ORGANISM: Homo sapiens
<400> SEQUENCE: 18

```
agatttgatc acagatgata catgtaagaa tgtcatagca caaaaaatg cacagatatt      60 tttaaaagga caaatttcag gacactttcc atctgagttc ataagaaagt cctcttgagt    120
atccttcaaa gttaaaaccc tctcccttc  agattaatga aaatattagg atgcatagaa    180
cacaatgggc actggtgata tggcccatgg tagctgaatt agat                     224
```

<210> SEQ ID NO 19
<211> LENGTH: 175
<212> TYPE: DNA
<213> ORGANISM: Homo sapiens
<400> SEQUENCE: 19

```
tgtgcccttt caggtgctga aaggcctcga gacgagctcc caggaccact gagttctggc     60
cttggtgttc gagggctaaa ggagaccaag agggacactc acaaacccca gtggcaaccc    120
ctttcctcta ccatcccctg gcctcggttc cccagccttc gagcccaggt tcccc         175
```

<210> SEQ ID NO 20
<211> LENGTH: 342
<212> TYPE: DNA
<213> ORGANISM: Homo sapiens
<400> SEQUENCE: 20

```
tttatctaat acagaagttt taaagtgtgg tttctgtacc agaagcattg gcatcacctg     60
ggaacttgtt agaaatgcaa attctaggct gggcgcagtg gctcacgcct gtaatcccaa    120
cactttggga ggccgaggca ggcagatcac gaggtcaaga gttcaagacc ggcctgacta    180
acatggtgaa acctcatctc tactaaaaat acaaaaatag gccaggtgtg gtggtgcaca    240
cctgtaatcc cagctactca ggaggctgag gcaggagaat tgcttgaacc ccggaggcag    300
aggttgcagt gaactgagat agtgctactg cactccagcc ta                      342
```

<210> SEQ ID NO 21
<211> LENGTH: 193
<212> TYPE: DNA
<213> ORGANISM: Homo sapiens
<400> SEQUENCE: 21

```
ttatgcttga ccttagccta cttcacaatc ttttgactgg gtcttccaga tgagctggaa     60
ggtcctacct gttcaatggt ctcacaccat tctggatgat tggatgttat atcacacact    120
atacataaaa ctattacaac atgacagaat catgcattgc agacctgaca ttcttctaac    180
aggacttgat aag                                                       193
```

<210> SEQ ID NO 22
<211> LENGTH: 567

```
<212> TYPE: DNA
<213> ORGANISM: Homo sapiens

<400> SEQUENCE: 22
tttagctctc tcttcattgc tattttatac acgaggaaac taaatctcag agaggttaaa      60
tccaaggccc tttagctagc aaatgacaga gcttctattc aaactcaggt ctgcctcaag     120
ccaaagcctc gtcctgatcc atttcattaa attactacca agtattacag atctttccta     180
gggcaatcat tttcttctat ataggactcc tggagtcact ctgagtattt ctaatgaggc     240
tgacaacaaa gggaagcttg aagtttcta agcagtcact tccacagagt tgcttaattt      300
gccctaattc ctggtttttg cagcccctgt cctaggctct tgctcacata tggacttgaa     360
tttgtggaaa ggtcaaaaat gatattctag atggagagat agtcttggag tacaaagaac     420
ataagcagaa atgagtaaat aaagctctag gagagcgtgt gatccagctc aattaaaggt     480
tagataagcc atggtggcac ataagctttg aaggtagagt tcaaatcata ccattaggat     540
tttgactgcc aggcagaaga gtttgat                                          567

<210> SEQ ID NO 23
<211> LENGTH: 330
<212> TYPE: DNA
<213> ORGANISM: Homo sapiens

<400> SEQUENCE: 23
gtctctctat gtgttctctc ctcatggcag ctctgagttc tgagagtgag tgtgccagga      60
gactggaagt agaggctgtc tgtttttaag gccaggggttt ggaagctggc acagttgcat    120
ttacacaaag cagttctaga tggaagggag gagatagacc ccacctctca atggagtgtc     180
cctcttcggt ggccccttta atggccattt cataggggtga agattaaata agacaatgag    240
cacaacgggc ttagcatagc acctgaaaca tcttaagagc tcaatgaatg gtagccattg     300
tcattatcag aggtagtatc agggtcattg                                       330

<210> SEQ ID NO 24
<211> LENGTH: 383
<212> TYPE: DNA
<213> ORGANISM: Homo sapiens

<400> SEQUENCE: 24 taatgtatt aattccttta tcattagaaa ttagtttttc tcacttacta caattgtaca       60
ttacaccaat cacctatcaa attctgctca gtttccaaga ataattcctg acctcagctg     120
atccacctgc ctcggcctcc caaagtgccg ggattatagg catgagccac catgcctggc     180
ccataataag attttttata aaactttggt ttttctattt gttagttttt ggagacagag     240
tctcactgtg tcccccaggc tgaaagtgca gtggtgtgat catggctcac tgcagcctca     300
accccaccag gggttctcct actttagcct ccccagtagc tgggaatata gacattcaac     360
acgatgccca gctagtatct aaa                                              383

<210> SEQ ID NO 25
<211> LENGTH: 238
<212> TYPE: DNA
<213> ORGANISM: Homo sapiens

<400> SEQUENCE: 25
gtggaaaagg aattatcttc aaatcaattc tacacagaag cattcagaca aacttctttg      60
tgatgagtgc attggtcaca cagaattgaa ccttccccttt gattgagcaa ttctgaaaca    120
ctcttttgga gggtctgcaa gtggatattt tagagctttg ggacaactgt ggaaaagtaa     180
```

```
atatcttcac ataaaaacta cacggaagca ttctgagaaa cttctttgga ggtgtgca      238
```

```
<210> SEQ ID NO 26
<211> LENGTH: 282
<212> TYPE: DNA
<213> ORGANISM: Homo sapiens

<400> SEQUENCE: 26
tcctccccca gccatgccat gcagccctcc tcctttgctg tcctaagaag aagggcctcc      60
gcccacatgt gcacattgga gacagactgt atgtagctca tgtgttcaag aaaccagagc     120
aggtggaggc ccaggcacga cactggggag cactcccagc gcgggaagta attttctcag     180
tgaacgacaa agcctctttg tgtgcacatg ttcatgtgct gagcacacac ccagtacgca     240
cacacctacc atatgtctta agagtttata gaaattgtgg tt                       282
```

```
<210> SEQ ID NO 27
<211> LENGTH: 261
<212> TYPE: DNA
<213> ORGANISM: Homo sapiens

<400> SEQUENCE: 27
aaaaatagtt tatcaaggca aatttgctgt ttggaaggga cacccagaat aatcagcaag      60
ttttagagaa aaagggctca aaaaatagtt cattagctta atgacaaaat acaaaatgtt     120
tgattagttg taatccaaca tttttttaagt attttatcac cctttccaaa aaaaaaacaa     180
cctgttgctg ttgacttatg agatcccagg tgaatttcat tctgaattttt tgaggtactt     240
gccggggtgg ggtgggggtg g                                              261
```

```
<210> SEQ ID NO 28
<211> LENGTH: 179
<212> TYPE: DNA
<213> ORGANISM: Homo sapiens

<400> SEQUENCE: 28 tcccttttccc agagcctcca aagtctgctt gcctgagggc catgactaaa gcgatggcct      60
tttcttttatc ccgtttgtcc cgttccgcct gctcctcctg atctctatta taaaaaacca    120
aagttgccaa gttcaatagg gtttctaagt tttgcttcgg gcctaaggtg gacttttga     179
```

```
<210> SEQ ID NO 29
<211> LENGTH: 351
<212> TYPE: DNA
<213> ORGANISM: Homo sapiens

<400> SEQUENCE: 29
gtgggtggag gaagatctta ttgtgggcca cattgaggat gttgactttg acttggagtg      60
aattgggcac tcattagctt agaccagagg atttactttg aataatatga acagtctca     120
ataactgatc tattcagtat ggtagccgct agtcatgtgt ggctgttgaa tacttgtgat     180
gtggctacct tgaattgaga tgtgctatat gtaaaacaca catggatttt gaagatgtcg     240
tatgaaaact aagaaaagtg aaatcatctg atatataatt acagtaatag gatcactagc     300
tgctgtactg agaaaagata taggggtgga agtgtcaaat ggtttggatc a              351
```

```
<210> SEQ ID NO 30
<211> LENGTH: 362
<212> TYPE: DNA
<213> ORGANISM: Homo sapiens

<400> SEQUENCE: 30
```

```
atatccacta gcagatactc caaaagagtc tttcaaaact gctctgtgaa tagaaatgct    60
caactctgtt agctgacgac atacgtcaca aagcagtttc tgagaatgct tctgtctagg   120
ttttatggga cgatatttcc ttttcacca taagcgtcca agagctccaa gtggacgaat    180
tctctagata tctagagaat tcgtcgtgcc catagttgtg agtaattata ctcgcctcac   240
tgagatgcca tgagacatca ataatacatg tcggggaaat gtccagcaga ggttgatact   300
cactaatcat gaagccccat ctccttctct tctggccagg gttgctgagc attggaggtg   360
ac                                                                  362

<210> SEQ ID NO 31
<211> LENGTH: 189
<212> TYPE: DNA
<213> ORGANISM: Homo sapiens

<400> SEQUENCE: 31
aaggtggggg gcagcttaac ttcaagggca cttcaaggat agccaggtgg ctgtcagccc    60
agctttccag gatgggagca ggatcttgac agaagggttg actgggaggg gcagttgctg   120
gtttgggctt cgttaggttg cattttttgtt tgttgtcctt tcatttccct ggggcagcac   180
cccttcctg                                                           189

<210> SEQ ID NO 32
<211> LENGTH: 250
<212> TYPE: DNA
<213> ORGANISM: Homo sapiens

<400> SEQUENCE: 32
agcttgcttc tcatctacct acaacttatt tgagcccacc cacatccttc cataaattct    60
attttgctaa aaataggcag aggcgatgtc tgttgcttgc aaccaagtat cctaactgct   120
actccaccat gtagacccta attcaagtcc caggcctgct attatactta gcagctgatc   180
cttgtccagg aattgtaccc cgccattatc atgggcccag gttccttcta tcactgttct   240
actattgtgg                                                          250

<210> SEQ ID NO 33
<211> LENGTH: 204
<212> TYPE: DNA
<213> ORGANISM: Homo sapiens

<400> SEQUENCE: 33
aacaatgtct caattctcaa accagcagag actaggaagg ggtcatatga tgcaataatg    60
ctggaatgca gattaaacaa aggaggcttc tccttttaca aactgactaa acagggaggg   120
ttctcatgaa agatttatag agcatccagg gcaaagtctg accacttaac ttttcatgaa   180
ttggtcacca ctctaacaaa cctg                                          204

<210> SEQ ID NO 34
<211> LENGTH: 108
<212> TYPE: DNA
<213> ORGANISM: Homo sapiens

<400> SEQUENCE: 34
taaattgtgg ctcatgcccc agttccttaa agggaaactg cagtttgtgg cagataagaa    60
atgtaggatc ccatgttttc caaatttagt tctctttagt atttgctg                108

<210> SEQ ID NO 35
<211> LENGTH: 478
```

```
<212> TYPE: DNA
<213> ORGANISM: Homo sapiens

<400> SEQUENCE: 35
agcttgtcac agtctcagtt ttttattttc acacagagtc tggttttatt tttaaaaaga      60
gaaggaaaaa agtgataaat gctagtgagg tgccacttcc ctccttcttc caggctctaa     120
ccgccagcta gctctctttc acaaaaccca cggatgcaga atcaggacat gttaaaatgg     180
aacagtctttt agagagggtc tagtctttttt aaaataagta aggatttggg gactaacaga     240
gaggaagccc ctgacttgct gaattgttag gagcaggcgg ttctcgagat tctgagccca     300
ggatccttttt ctgtgaacca tgcacgtgct ggcactggcc tcaggagaca gtgccctgcc     360
ttggctgtca ggtccacgga gaagtctcag gtttgcccca tcactacgga tgccctaaga     420
agcaagggca taggaagctt taagggtcat cgagactggg acaagagaaa tgagtgca       478

<210> SEQ ID NO 36
<211> LENGTH: 216
<212> TYPE: DNA
<213> ORGANISM: Homo sapiens

<400> SEQUENCE: 36
agcttgtgct ggtgtgaatg tgtatgggtt acagctgtgt tttcatattg tttaaaatga      60
aataaaacca tgttttgatt ctattaaaaa tagagaagct ggctgggtgt ggtggctggt     120
gcctgtaatc ctagcacttt gggaggctaa ggtgggcaga tcacctgagg tcaggagttc     180
gagaccagcc tgcccaacat ggtgaaaccc ccatct                               216

<210> SEQ ID NO 37
<211> LENGTH: 123
<212> TYPE: DNA
<213> ORGANISM: Homo sapiens

<400> SEQUENCE: 37
ggtaggagtt caagaccatc ctggccaaca tggtgaaatc ccatctccgc taaaaataca      60
aaaaattagc cagatgtggt ggcatatgct gtaaccccag ctacttggga ggctgcagga     120
taa                                                                   123

<210> SEQ ID NO 38
<211> LENGTH: 233
<212> TYPE: DNA
<213> ORGANISM: Homo sapiens

<400> SEQUENCE: 38
ggttctgcgc accaaaatgt ttggtggaca tctgtgtccc cccccacccc aaaatccacc      60
ccagcacaca ctcaactctt ttaggccgag gggcacgtcc aactcatctg gtgaatacat     120
cagctgaatg caatctgctc tcacaaacag atgtcccagg aggcggagct tgcagtgagc     180
tgagattgtg cccctgcact ccagcccggg cgacagagca agactctgtc tca           233

<210> SEQ ID NO 39
<211> LENGTH: 529
<212> TYPE: DNA
<213> ORGANISM: Homo sapiens

<400> SEQUENCE: 39
atcaccagca tggatcaaat ctctgctctc ccctcatctt gttgaccata aaaataattt      60
ctaagaggca ctttaaaatg gacaaactaa atgacacact agccacccaa agtctcctat     120
attctaaagt gtgtgatgag acaaactgat tcaaaatagc cctagggtga gaatttcctg     180
```

```
ttcaaatctg cagtgacaca ttggtgagga atctactttc tccactcttg cctcactctg    240
acccttcaaa gggcagtctg tgaagatcac agataacgtt tgtgtctttc agaggtaacc    300
tgacctctcc actgaagggc gtgtggcttt ctgatgacag taggtaagtg ttgctccctct   360 ccctgttcct ctactagctc atctcattta gtagaagatt gtaagtactg ctgtgatgc     420 acctgaggta aagttgatat agacgaaaat caaggtagaa attattcac gtgaataatt     480 caaggtgaaa aacgagccaa aatataaact atgtttaagg atttcttag               529
```

```
<210> SEQ ID NO 40
<211> LENGTH: 177
<212> TYPE: DNA
<213> ORGANISM: Homo sapiens

<400> SEQUENCE: 40
gtctcggcta ctgactgcaa ccccgcctcc tgggttaagc aattctcttg tctcagcctc     60
ccgagtagct gggcctacag gtgtaccacg cctggctaat ttttgtattt ttagtagaga    120
cagggtttca ccatattgat caggctggtc tgaaactcca aacctgagga atccaa        177
```

```
<210> SEQ ID NO 41
<211> LENGTH: 293
<212> TYPE: DNA
<213> ORGANISM: Homo sapiens

<400> SEQUENCE: 41
atttctggat gtcaatgagg tattaacaca taagagagga acatttttt atgttctttt      60 cttctgttcc tagataccag aagcatcatg ggagtggtgg cgtaaggata ctgagagtag    120
atagagaagg cactaaactc agagagaggc tagaaaggtg gaagtggtat tagttattcc    180
ctgtgttttc tcctctcaca ttcttttgca atatgtctgc ttttgagtgt gatggtgttg    240
cacacttcct aggtactcaa acctccatgc ttagcattcc catggcactg atc           293
```

```
<210> SEQ ID NO 42
<211> LENGTH: 309
<212> TYPE: DNA
<213> ORGANISM: Homo sapiens

<400> SEQUENCE: 42
ttatcctgct gggtactatg aattatcctg ctgggtcact gggtggatcc ctaggcaggc     60
agtattgcct taatctgtat ctgagaggat ctggaactga gtttcagggc tattttaggg   120
tctatagctg ggaccaatgt cagcaggcct gcccagagga ctcaggctgc atgtagtcct   180
ctgtgtccct gtgctgctgg caggactgat cacagaccac tactgagagg ggctgagctg   240
agactcagaa ccatttcagg atctgctgta ggcctggggt cagcaagcat gtcctggcaa   300
atgtttctt                                                           309
```

```
<210> SEQ ID NO 43
<211> LENGTH: 180
<212> TYPE: DNA
<213> ORGANISM: Homo sapiens

<400> SEQUENCE: 43
accactcaca gattcactcc aaaggttact gcaaatgagc acccttcaaa tattcgcaca     60
acaccatggg gaaatgttct ttgctaacat aagcagagga tcccagcgcg aggagagagg    120
gaacctcagc tgcgaaggtt tccacattca aggtgggggct gaccaccagg aaacaaaggc   180
```

```
<210> SEQ ID NO 44
<211> LENGTH: 308
<212> TYPE: DNA
<213> ORGANISM: Homo sapiens

<400> SEQUENCE: 44
agcttctaac ttgcttgctg ctaccacctg ctgtgtggcc tggttcctat agcccacaga      60
cccataccag tccatggcct ggggcttggg gaccgttgct ataagaagtc agaaatagtg     120
gttccctagg aagggtctcc gtcagaacat ttttggcaca taactaatac cttgtatgac    180
agctgctcag gagagggtga agcaggcatt cactgctagg tctgatctct taagagagcc    240
ccttaaggcc caggaagctt ggccttgacc caggcaggaa gccacagggg gaatattctg    300
gatatgag                                                             308

<210> SEQ ID NO 45
<211> LENGTH: 217
<212> TYPE: DNA
<213> ORGANISM: Homo sapiens

<400> SEQUENCE: 45
ccacccttgt taccgggctg ctcaccagga cctgggtagt ttaccggggt gcacaaaggc      60
acgaacatat gacagagtgg gcaagatgaa ggaaggagcg ctgcaagcca gagggaaagg    120
gagacagaga agtcaggagc aggggctggg tgacggggct cactctctac ttaaagtggt    180
ccatgagaca tctccacctc atgccaaaga acggaga                             217

<210> SEQ ID NO 46
<211> LENGTH: 155
<212> TYPE: DNA
<213> ORGANISM: Homo sapiens

<400> SEQUENCE: 46
tgtctcgatc tcctgacctc gtgatccgcg caccttggcc tcccaaagtg ctgagattac      60
aagcatgagc caccgcgcct agcctgggtg ggggctgttt ttaaatctta tctcaagttc    120
atgtcggctt tggagatttc attaaacacg acaag                                155

<210> SEQ ID NO 47
<211> LENGTH: 567
<212> TYPE: DNA
<213> ORGANISM: Homo sapiens

<400> SEQUENCE: 47
ttcctgcaaa actaggccat cggctcctcc atgccccagc ctcagggagt cattagattg      60
tcagggctga gtcagtgccc aaggtcacac agcaattaac tagaggccca gactagaacc    120
aatgtctgac tcggacaccc taaggctgac ttttgaatag gtggaccccgg agcctcggag   180 ctgaggggag gagtcaggca cagaggatga gagacctgag acagcaggct gtgcttcctg    240
atttgacact cctctgattc catgttggct ctgggctcct taaaacaagg ccagtcctgc    300
aggtgggcgg gatgtgtggt ggggaccaga gcctctccag ccggaagtca gaggcccagg    360
gttttggaag gactccaggt ctttccttgc atctggaatt aaaaccttcc ccggctgagg    420
cgcgtagatc acctgacgtc gggagttcga gaccagcctg accaacatga agaaacccccg   480 tcactactaa aaatacaaac aattagctgg gtgtggtggc gcgtgcctg taatccaaac     540 tactcaagaa gctgatgcag gacaaat                                        567

<210> SEQ ID NO 48
<211> LENGTH: 290
```

```
<212> TYPE: DNA
<213> ORGANISM: Homo sapiens

<400> SEQUENCE: 48
ccacggagcc gtccccagcc cagctgggga cacgtccccc ttctctccga cacaccctgc     60
ctgccaccac gacacaccgg cctgttgggg gtctctttta agtgcttgcc actctgaggt    120
gactgtccct ttccaaagag gtttctgggg cccaggtggg atgcgtcggc ctgagcagga    180
ggatctgggc cgccaggggc tggggactgt ctcctgggga aggaagcgcc tgggagcgtg    240
tgtgctgacc caggaccatc cagggaggcc cgtctgtggg gcaagcggga              290

<210> SEQ ID NO 49
<211> LENGTH: 276
<212> TYPE: DNA
<213> ORGANISM: Homo sapiens

<400> SEQUENCE: 49
gtatttagga attagaggta aaactctatg ttattatctc tgaagataat gacaagcaat     60
tcaagcaatg aaaaattcaa atatacattt gcttcgccac ataactacgt cactgctggt    120
ggatacatga agaggaacc catactattc tggctgatgc ccagcttccc aggaattagt    180
gggatatagt gctggacatg acgttacctt gagtacatga cagtcagccc ctaaccaggc    240
tctgattcac aagactagga ggtactcgct ttaagt                              276

<210> SEQ ID NO 50
<211> LENGTH: 156
<212> TYPE: DNA
<213> ORGANISM: Homo sapiens

<400> SEQUENCE: 50
catgtatcta gaatttgctt tactatttga cttctgtgaa aagtttctgt gaagactgct     60
ttcagagtgg aggttatgat ctcaattctg ttggccctgc caaacatcac attcacgtca    120
tcatgcttgg actgtttgtc ttctcattga tattcg                              156

<210> SEQ ID NO 51
<211> LENGTH: 345
<212> TYPE: DNA
<213> ORGANISM: Homo sapiens

<400> SEQUENCE: 51
agtagggatt tctttgtaac tgccctgacc ctggattatg ccctactcct tattttgtct     60
aaacattagc tgggcatggt ggcatgggcc tatagtccca gctacgcagg aggctgagtc    120
aggagagtca cttgagtcca ggagcttaag gctacagtga gctatgatcc agccactaca    180
ccccagcctg ggcgacagat cctgtctcta aaaagaaaa aaaaaatcct tgagagtagc     240
ttggctttgc agaatgcagc tgtttcttgc ttttgagggt gtttgtttgc catttgaccc    300
tcttttttta aaccttatgt ttataaggga aagcctctta cagta                    345

<210> SEQ ID NO 52
<211> LENGTH: 150
<212> TYPE: DNA
<213> ORGANISM: Homo sapiens

<400> SEQUENCE: 52
tgtgtacaat aacagaaaaa gttgcaattc cttgcctcca ctgtgagaca aaccccagcc     60
acatctccag cacacaagaa cttccaaatg cctgaactgc agcagccagg tgtttctcca    120
gaacctcctc ccccaggagc ttgctacacg                                     150
```

<210> SEQ ID NO 53
<211> LENGTH: 189
<212> TYPE: DNA
<213> ORGANISM: Homo sapiens

<400> SEQUENCE: 53

```
atctgatgaa agagtagcat gaagatggag taagaattcg tcctgtggag gcaagggcaa        60
taacattcca gcaaatagaa tcacataagg aaaggcatgc aggagggaaa ggacagggga       120
caggacatac ttgggaaaga cgagggatc aaatttggct ggattatgcc atatcttgtg       180
caaaagagg                                                              189
```

<210> SEQ ID NO 54
<211> LENGTH: 190
<212> TYPE: DNA
<213> ORGANISM: Homo sapiens

<400> SEQUENCE: 54

```
cacttgcact gaggaatgga ggagcagggc gctgtctggc cagcggtgcc atagcaacca        60
ctggctccga tgctgccacc acctccaggg ttgttcttcc tatctgaaag ggactaagca       120
gaatgaggcc tctgctgccc cagggctgaa atgggtttct gcgaagtctg tttcttacag       180
tttgatccac                                                             190
```

<210> SEQ ID NO 55
<211> LENGTH: 643
<212> TYPE: DNA
<213> ORGANISM: Homo sapiens
<220> FEATURE:
<221> NAME/KEY: modified_base
<222> LOCATION: (630)..(630)
<223> OTHER INFORMATION: a, c, g, t, unknown or other

<400> SEQUENCE: 55

```
cattaactca gtctctgccc ccactttact tgggccatga gctttcatgc ctcgaattta        60
ataatgaatt ttataacaca taactcccta atgacactcc aaaggaagga attgtgtcat       120
ttttgttgat ggttgccatt tgttcactta tttttatcac ttttttcaaaa catgaggtca     180
attttacctc caatgggttc tccaggacga attctctaga tatcaagctt gaattcgtcg       240
tttccaacga aatcctcaaa gctatccaaa tatcctcttg cagattttac aaaaagagtg       300
ttccaaaact gctctatcaa aagaaagctt caacactgtt agttgagggc gcacatcaca       360
aataagattc tgagaatgct tctgtctagt tttcagggga agatatttcg ttttcacca       420
taggcctgaa agcgctccaa atgtccacat ccagatacta caaaaagagt gtttcaaccc       480
tgctctatga aagggaatgt tcaactctgt gacttgaatg caaacatcac aaagaagatt       540
ctgggaatgc tgctgtctgc ttttcatatg taatcccgtt tccaacgaaa tcctcaaagc       600
tagacaaata tccacttgca gattccacan aaagagtgtt tca                         643
```

<210> SEQ ID NO 56
<211> LENGTH: 139
<212> TYPE: DNA
<213> ORGANISM: Homo sapiens

<400> SEQUENCE: 56

```
atagtggagg ccatccaagg cttttatcct tgctaaggat cttcaacctc ctgcaacatg        60
ggaatctgga tgaagaggcc aatgaactgg aacttacaat gtaaccacca acctaattaa       120
cagtaagaca atgctatag                                                  139
```

<210> SEQ ID NO 57
<211> LENGTH: 225
<212> TYPE: DNA
<213> ORGANISM: Homo sapiens

<400> SEQUENCE: 57

```
gtggatcacc tgaagtcggg agtttgagac cagcctgacc acatggagaa acccatctct    60
acaaaaaata caaaattagc caggcatggt ggcacatgcc tgtaatccca gctactacgg   120
aggctgaagc aggagaatcg cttgaacctg ggaggcggaa gttgtggtga gccgagatca   180
tgccattgca ctccagcctg gcaacaaga gcgaaactcc atctc                    225
```

<210> SEQ ID NO 58
<211> LENGTH: 327
<212> TYPE: DNA
<213> ORGANISM: Homo sapiens

<400> SEQUENCE: 58

```
ccattagcct tctgatggca gggcaaataa taattctcat tgcaaagaaa taaatatggg    60
tttaaattcc aactttttag attttagaga atagccgggc acagtggctc acgcctgtaa   120
tcccagcaca ttggaaggcc gaggcagacg gataacgagg tcaggagatc gagaccatcc   180
tggctaacac ggtgaaacct cgtctctact aaaaatacaa aaaaattag ctgggcctgg    240 tggcacacgc ctgtaatccc agctactcag gaggctgagg caggagaatc gcttgagccc   300
aggaggcaaa ggttgcagtg agccgag                                       327
```

<210> SEQ ID NO 59
<211> LENGTH: 109
<212> TYPE: DNA
<213> ORGANISM: Homo sapiens

<400> SEQUENCE: 59

```
gttaatcaac aacatttttt ggccatttat tctgtgccag gccttttgcc gggttctggg    60
aattcagcag gaaagaagtc tgacacactg gctgcccttt agtgaagga               109
```

<210> SEQ ID NO 60
<211> LENGTH: 236
<212> TYPE: DNA
<213> ORGANISM: Homo sapiens

<400> SEQUENCE: 60

```
aataacagtg gccgctaggt gatgcccgaa gacaccgatg cctgcctgca aatgtccgtc    60
agcagggaaa agaattaatg aattaattaa tttccgtatt tatttagaga ccgagtctca   120
ctcactctac agcctgggcc gtagtgcagt ggcgcgatct cggctccctg cagcctccgc   180
ttccctggtt caagcgattc tcccgcctca gcctcccgag gagctggcat tacagg       236
```

<210> SEQ ID NO 61
<211> LENGTH: 445
<212> TYPE: DNA
<213> ORGANISM: Homo sapiens

<400> SEQUENCE: 61

```
tggtgaaatc catctctacc agccggcata gtggcaggtg cctgtagtcc tagctacttg    60
ggaggctgag acaggagaat cacttgaacc tgggaggcag aggttgcagt gagccaagat   120
cgcgccactg tactccagcc tggcaacaga gagagactcc gtctcaaaaa caaaatacaa   180
acaaaacagg aggacgagac agcgagagga acagcgtccg gggcgacccc cagtccaccg   240
```

```
cgggggcctg gcgcgcttgg ggcaaaggcc ctaggagacc ccttctggcc acaaaatcga      300
gtatgacaga aagggccag cggggcgct tccttccag ggccacttgc cggaatgtaa         360
gagggacgga gagacgtccg gaaaaggctg ccacgctcgg agcgctgcgc caggccaggc      420
acctaggcca ggggagcgga gacct                                            445

<210> SEQ ID NO 62
<211> LENGTH: 535
<212> TYPE: DNA
<213> ORGANISM: Homo sapiens

<400> SEQUENCE: 62
ggaagtactg cagatgtggt agaaatagaa agagaaccag aattagaaac agagcctgaa       60
gatgtgactg aactgctgca atcttgtgat caaacttgaa cagatgagga gctgcttctt     120
atgaatgagc aaagaaagtg atttcttgag atggaatgta ctcctggtga atatgctgtg     180
actactgcag aaatgagaac aaaggattta ggatataatc tcagctgata aagcagcagc     240
agggtttgag aggactgatt ccaattttga aagttctact atgggtaaaa tgctataatg     300
cctggggtgc tggctactgt agtcccagct aatcaggagg cagaagtaag atgatcactt     360
gagtctaaga gtttgagtcc tgcctggaca acacagtgag acacccatct ctattaaaaa     420
ctaaaaacaa atataacgct atcaaacagc atctcatgca acagagaaat cttccgtgaa     480
aggaagagtc aattaatcca gcaaacttca tggttgtctc cttttaaaca attgg          535

<210> SEQ ID NO 63
<211> LENGTH: 316
<212> TYPE: DNA
<213> ORGANISM: Homo sapiens

<400> SEQUENCE: 63
aaatgacagc aagaggtgtt gggggcaccc agtgaggagc tggggagaag ggaagaaggt       60
gctcccatgt tttctaagca cttccctggc cattggctct ttttccttt ctttccttt      120 tttttttttt tttttttttt tttttttttt taaaaagggg gtcttgcaat gttgcctaaa     180
ctggtctaaa attcttggac aaaattggtc ctcccaccta acccacccaa ttagctggaa     240
ttacaaccgt ttacaaccaa attgggttgc caagggcttt ttcttttaaa aaggagttta     300
actcggttgc ccatgc                                                      316

<210> SEQ ID NO 64
<211> LENGTH: 282
<212> TYPE: DNA
<213> ORGANISM: Homo sapiens

<400> SEQUENCE: 64
atccgggcat ggtggctcac gcctgtaatt ctaacacttt gggaagccga ggcaggccga       60
tcatctgagg tcaagagctc aagacaagcc tagccaacat ggcgaaacct catctctact     120
aaaaatacaa aaattagctg ggtgtggagg cacacgcctg taatcccagc tacttgggag     180
gctgaggcgg gagaatcgct tgaacctggg agttagaggt tgcagtgagc cgagatcatg     240
ccattgcact ccagtctggg agacagagtg agatcccatc tc                        282

<210> SEQ ID NO 65
<211> LENGTH: 279
<212> TYPE: DNA
<213> ORGANISM: Homo sapiens

<400> SEQUENCE: 65
```

```
ccatcttggc caggctggtc ttgaactcct aaccttgtga tccatgcccc tcggcctccc      60
aaagtgatga ctgtagtttt aagtcctagc atctgaaagt aaaagtcctc caattttgtt     120
cttcaagatt gtgttgggta ttcttcagcc tttgcatttc acattaaat ttagaatcag      180 cttctcaatt gctgattctt tagtaaaaga aaaacaaccc tgctggaatt ttgattggaa     240
gtttgttgta gcataaggct ttggaagctg caaaataaa                            279

<210> SEQ ID NO 66
<211> LENGTH: 261
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, g, t, unknown or other

<400> SEQUENCE: 66
ttcctgtggg tctaaaaccg naacgctttc ttccccgacc cctgctcccg tatcacccca     60
acctcaagtc ttttggcaca gccggctaca gactcgagtg tcagtttaat gcttgttccc    120
taaggtctcc ccagggctct taggacggcg tcaggattag gattcgggtt cgggtgcgcc    180
tcttcgcgcc tgcgccggcg ctggcagggg gagggcctct ctgcgcctgc cccggcgctg    240
ggggcctttg caagggtgga g                                              261

<210> SEQ ID NO 67
<211> LENGTH: 521
<212> TYPE: DNA
<213> ORGANISM: Homo sapiens

<400> SEQUENCE: 67
caagttgcta tacattgtac tttttaatgg aaaaatctct gtatttgagc tcttgttata     60
ttttctgtgg tatctcaaaa attctcttgg atataagcca tctggatttt tctgcagtcc    120
tctcaagttt caaaatagtg atacttagaa cgtattttgc agggtttcta tcggtcaagg    180
gcatgcagtt ctgaaaatct tgtgctgtga ggtcagacag gaccgttggc catctgccaa    240
ttgacttgca ttgtttacct ttttaactca caaccctgga aacgctgttg gtgtccccc     300 ggccttcact ggttttctga gtatctgccc ctttgcctgc ttgaagtgct tagtcctggc    360
gagtgaagcc tttaggagtt cccaatttct tgcttcacag gttactaaaa atgaagacat    420
atctgttaag tgttgctcaa gagaccaaaa cataatccta ggacaggatg tctggaaagg    480
atgtcttgcc tgtcacgcag cataatacat ggtaacaagt a                        521

<210> SEQ ID NO 68
<211> LENGTH: 253
<212> TYPE: DNA
<213> ORGANISM: Homo sapiens

<400> SEQUENCE: 68
ggtaggactg ttcttccttg atgcaggtgg gaggttggcc ccagggatgt gatgtgctgc     60
cctctctggc tccctctggc acagcgcttc ctcagatggt gcaattttcc cactcacata    120
aatctgactc catttcctga gtccctaatt ttcccaagga gaaagggca ggaagtagtg     180 gagagggccg ttgactaaag agggcccacc agtgactaag ccatttacat tcacaaagga    240
gacaggccct gca                                                       253

<210> SEQ ID NO 69
<211> LENGTH: 251
```

```
<212> TYPE: DNA
<213> ORGANISM: Homo sapiens

<400> SEQUENCE: 69
tggattagac aatggtttct taggtatgac accacaagca caaacaacaa aaggggaaag      60
agataaatcg gactttatca aaattaaaaa ctgtggtgtt caaaaggata ctgtcaagaa     120
agtgagccaa cataccacag aatgagagaa aatatttgca gtttatgcat ctcatatggg     180
acttgtacag gttatatacg gaactcttat aggtcaatga aaggataaat aacccattta     240
aagaatagac a                                                          251

<210> SEQ ID NO 70
<211> LENGTH: 351
<212> TYPE: DNA
<213> ORGANISM: Homo sapiens

<400> SEQUENCE: 70
ttgagtggac atcagaatga tctgaagagc ctatcaaagc atagagggct gagccccact      60
ccaataggtt ctgatctatg gatttcgcat ggggtctaag aatatgcatt tctaaacaaa     120
attcctagag gctactggtt ctgcttgtct aaagaccaca cacttgctga aaacaactgc     180
tttaggccat ataattaagg ctcctactct ctctagttgg cctcatatcc ttagttcact     240
caagctttga actacttatt aaaagtgact tctgcaatcc taaacatgta agacattata     300
cagcatcaag cccaccaaat agtccctaaa gataaactct ataagctgga c              351

<210> SEQ ID NO 71
<211> LENGTH: 397
<212> TYPE: DNA
<213> ORGANISM: Homo sapiens

<400> SEQUENCE: 71
ctaacctagc ttgggcccgc tgaaagtaac tgaacccaaa gcagcggccc agccagctcc      60
atgcaggaca acttcccatg tgaacgtgga ggagctgtga acagaaacc tactcactca      120 cagatcttta acaaatagcc cccgaactga accaaaccaa actgaaataa agggaggaac     180
ttaggccggg cacggtggtt cacacctgta atcccagcac tttgggggt caaggcaggt      240 gggtcacctg agctctggag ttcaagacca gcctggccaa catggtgaaa cctcatctct     300
atttaaaatg caaaaattag ccgggcatca tggcacatgc ctgtagtccc agctactcag     360
gaggctaagg cagaagaatg gcttgaaccc aggagga                              397

<210> SEQ ID NO 72
<211> LENGTH: 265
<212> TYPE: DNA
<213> ORGANISM: Homo sapiens

<400> SEQUENCE: 72
gttggttggg cttaggaaat gtaaattata gtgagaacca tatcaggtcc ctcaagggca      60 gaattttct tcttgagtaa aattttgaaa tctaggaaaa tcttgttttc cctagagtgt     120
cacatgatgg ctagacttaa aaatttctct tcccttatga cagaaatgaa aacttttattt     180 ttttaaatgg tatatacttc ttgcagttgt ttcatttaat agactttat gctgttattt      240 tggtcagagt aaatattgtt gtggt                                           265

<210> SEQ ID NO 73
<211> LENGTH: 416
<212> TYPE: DNA
<213> ORGANISM: Homo sapiens
```

```
<400> SEQUENCE: 73
tctaaaaaac tccctactat gcttagaccc tccttgagtg cattcctgcc cacaatccca      60
agccatcttc tccatccttg agtctgtgga atatgagagt cctggcatat tgctttagga     120
taggactgta tagttgactg ctgagatgag gagtcccaga aatcttcctt ccagctgtgg     180
cccaggaaga ttacccaatg aaacctgtgt gtggggtgt gtgtgggaca tatgctgggt      240
gaggtggggt caggagtaag taaaattaat attgtgctga agaatgctca ctgaaaatag     300
tcaccacccc tacagaagat ggaatcggga agagttttg acccaaatcg tccactcatg      360
ccccgtggag cttgtgctat gatgagaaca gacactaccc agggaaaata atccac         416

<210> SEQ ID NO 74
<211> LENGTH: 417
<212> TYPE: DNA
<213> ORGANISM: Homo sapiens

<400> SEQUENCE: 74
ttagatcaaa agaaagtcag aatacaacaa gatatagaag tacggaaaga cagatctgat      60
gcagtgagaa attctaacat acataataag attcatgaaa gagataaaaa acagttggat     120
cccagcactt tgggtagccg aggcaggtgg atcacttgaa gttgggagtt tgagaccagc     180
ctaggcatct ttcattcatt caaggagag aggggtgtg acggctggga ctgacaatga       240
aaacagagac agcctcacat gtggacaaac ctcctggtaa caacctaaat ccatgtactg     300
ctgccatgag gccatggaaa ttcagtctct ggttcctgga cagtgtcctc aactgttccc     360
cagcccaaga gagctgaag ctcaaagagg agggcaagtg actgcagatc agctcct        417

<210> SEQ ID NO 75
<211> LENGTH: 228
<212> TYPE: DNA
<213> ORGANISM: Homo sapiens

<400> SEQUENCE: 75
cctgggaggc tgagacgaag atcacttgaa tccaggaggc ggaggttgta gtgagccgag      60
atcgcgccac tgcactccag cttgggcaac aaagaggaaa actccatctc aaaaacaaaa     120
acaaaacaaa caaacaaaaa accccacaaa cctgcatgtg tagccccgaa cctaaaagaa     180 aaattttta aaaacccagc atatcaaagt ccttcaatac atatgatg                   228

<210> SEQ ID NO 76
<211> LENGTH: 220
<212> TYPE: DNA
<213> ORGANISM: Homo sapiens

<400> SEQUENCE: 76
gggctcgcac gggtaggggg ctccggcgga gttgggtgac cgtgaggcgg ttggtttgga      60
gaggttgtca ctaaggagga gtttactttt catttgtgga gatgatggga gcccaggaaa     120
tgtggtcaga aaaaggcccc tgagggggtc ctggaagcgt ccttagctgg tcctggggga    180
ctgggcgggg aagggagcgc agaaggaagc aggtgggctg                           220

<210> SEQ ID NO 77
<211> LENGTH: 352
<212> TYPE: DNA
<213> ORGANISM: Homo sapiens

<400> SEQUENCE: 77 cccccttcgcc aggcaacgcg cgagactgac aggcctcccc ctccctctgg ccttccgaag    60
```

| | |
|---|---:|
| cgcgcggtgg cggctaagcc tcagcggcag tctcctccct ccttccctcc ctccccgact | 120 |
| ccctccctcc cgccttccct ctccgctctc ctccctccac ccgctctcct tcccctccc | 180 |
| ccctccgaac ccgggcgcaa gggggaatt agaaactgct ctagaaggat tttaaacaac | 240 |
| tggctgttct ctccgccgcc acccctcccc ccgcgccgcc cgcgctcagc tcctcactgg | 300 |
| agagaaggcg ccgggaggag gagaaactgc ggcctggagt ctccggccgg ag | 352 |

<210> SEQ ID NO 78
<211> LENGTH: 309
<212> TYPE: DNA
<213> ORGANISM: Homo sapiens

<400> SEQUENCE: 78

| | |
|---|---:|
| tggacctcta gtgactgacc gacaggaaaa caggtaccag aaagaatgaa gacttttaca | 60 |
| tcaggtgttt ttagaaggga ttcgtggtta tctgagtaga gttatgatac cagagtggtg | 120 |
| tgttcatcca aggctgataa ggaaccttaa cttgacaaga taaacaagag tgaatcagct | 180 |
| aaatgacatt tgtgattctg cttatcctc tgaagatgaa aaataatcac tgtctcaggg | 240 |
| tcaaagtaat gactcatctc ttagaaattg aggtggaaat gtccagattt gggaagaata | 300 |
| atatttcac | 309 |

<210> SEQ ID NO 79
<211> LENGTH: 228
<212> TYPE: DNA
<213> ORGANISM: Homo sapiens

<400> SEQUENCE: 79

| | |
|---|---:|
| tgtatgttta ggattgtgat attttcctgt tggacaaggc tgttcatcat tatataatgt | 60 |
| ccccctttgt ctttttaac tgctgttgct ttaaagtttg ttttgtctga tataagaata | 120 |
| gctactccca ctcacttttg gtgtctattt gcatgaaata tctatttcca agtctttacc | 180 |
| ttaagtttgt gtgagtcctt atgtgttagg tatatctctt gaaagcag | 228 |

<210> SEQ ID NO 80
<211> LENGTH: 172
<212> TYPE: DNA
<213> ORGANISM: Homo sapiens

<400> SEQUENCE: 80

| | |
|---|---:|
| ggtctcttct agtttctttt ccttttcct acctagcata accattaaat tgaattcaca | 60 |
| acccacaaag aggtcacagc ctgaggactg gaaaacagtg aactagacaa cctcagcgct | 120 |
| ctggcgcttc cagaaaaccg cgtgtcactg cagcatcctc cgcatcatcc ag | 172 |

<210> SEQ ID NO 81
<211> LENGTH: 340
<212> TYPE: DNA
<213> ORGANISM: Homo sapiens

<400> SEQUENCE: 81

| | |
|---|---:|
| cttaggagaa ataaaaacat atattcacaa aagacgtgta tagcaaatgt tcataacagc | 60 |
| attatagata atagccaaaa agtgaaaaac acccaaatgt gattggataa acaaaatgtg | 120 |
| gcatatccct acaacagact actactcagc aataaaaagg aacaggccgg gcgcagtggc | 180 |
| tcatccctgt aatcccagca ctttgggagg ctgaggcagg cggatcacct gaggtcggga | 240 |
| gttcaagacc agcctgacca acacggagaa accccgtctc tactaaaaat acaaaatttg | 300 |
| ccaggcgtgg tggcgggtgc ctgtaatccc aggtactcga | 340 |

<210> SEQ ID NO 82
<211> LENGTH: 84
<212> TYPE: DNA
<213> ORGANISM: Homo sapiens
<220> FEATURE:
<221> NAME/KEY: modified_base
<222> LOCATION: (9)..(9)
<223> OTHER INFORMATION: a, c, g, t, unknown or other

<400> SEQUENCE: 82
gtatttcant tcttgcagc cagtctctca gtttgctgat gtcttatttc aattctgtga      60
gaccttatct tcttggttta tgca                                           84

<210> SEQ ID NO 83
<211> LENGTH: 209
<212> TYPE: DNA
<213> ORGANISM: Homo sapiens

<400> SEQUENCE: 83
acaaattgca gactgcagcg ttctgagaaa catctttgtg atgtttgtat tcaggacaca      60
gagttgaaca ttccctatca tagagcaggt tgggatcact ccttttgtag tatctggaag     120
tggacatttg gagcgctttc aggcctatgt tgaaaaagga aaaatcttcc cataacaact     180
agacagaagc attctcagaa acttgttgg                                      209

<210> SEQ ID NO 84
<211> LENGTH: 360
<212> TYPE: DNA
<213> ORGANISM: Homo sapiens

<400> SEQUENCE: 84
gttctcagat tgagtggaca tcagaatgat ctgaagagcc tatcaaagca tagagggctg      60
agccccactc caataggttc tgatctatgg atttcgcatg gggtctaaga atatgcattt     120
ctaaacaaaa ttcctagagg ctactggttc tgcttgtcta agaccacac acttgctgaa     180 aacaactgct ttaggccata taattaaggc tcctactctc tctagttggc ctcatatcct     240
tagttcactc aagctttgaa ctacttatta aaagtgactt ctgcaatcct aaacatgtaa     300
gacattatac agcatcaagc ccaccaaata gtccctaaag ataaactcta taagctggac     360

<210> SEQ ID NO 85
<211> LENGTH: 191
<212> TYPE: DNA
<213> ORGANISM: Homo sapiens

<400> SEQUENCE: 85
taggaggagt aggggcaggt tttggctcgt aagaaggcct agatagggga ttgtgcggtg      60
tgcgatgcta gggtagaatc cgagtatgtt ggagaaataa aatgtgcata gtggggattt     120
tattttaagt ttgttggtta ggtagttgag gtctagggct gttagaagtc ctaggaaagt     180
gacagcgagg g                                                         191

<210> SEQ ID NO 86
<211> LENGTH: 265
<212> TYPE: DNA
<213> ORGANISM: Homo sapiens

<400> SEQUENCE: 86
tattattact ttctaagtc ctttggtaag caacttcctc ttttcctctg ttctccattg       60
cttttaccta tttttaaaag ttttttaagct gttaccgatc gggtgcagat taaactgtga    120

```
ggtctggctc catccaatgg acacaggaca tagtaacaag acaagctgt atacagaata      180 aaaaatgctt cgctcctttg tacaaatgtg ctgtcaccaa tgtaccatgt gcaaggagaa    240
acctttctgc aaaaaataga attgc                                           265
```

<210> SEQ ID NO 87
<211> LENGTH: 179
<212> TYPE: DNA
<213> ORGANISM: Homo sapiens

<400> SEQUENCE: 87

```
gattgcttag tccagttgat tatgctcaga aagtatttcc taaagccttc aaatttactt     60
taaataccct tgagaccaac tcagtcctga agaatacccta caaaggccca gatgaaaaca   120
atttactgaa accctaactc taccattaaa ttttactatc aggttgatca gaggaggcc    179
```

<210> SEQ ID NO 88
<211> LENGTH: 172
<212> TYPE: DNA
<213> ORGANISM: Homo sapiens

<400> SEQUENCE: 88

```
ttctactaat aatacagaat tagctgggcg tggtgttgca tgcctgtaat ctcagctact     60
caggaggctg aggcaggaga atcgcttgaa cccgggaggc agaagttgta gagagccaac    120
atcgtgccat tgcattccag cctgggtgac aagagcaaaa ctctgtcgcg aa            172
```

<210> SEQ ID NO 89
<211> LENGTH: 231
<212> TYPE: DNA
<213> ORGANISM: Homo sapiens
<220> FEATURE:
<221> NAME/KEY: modified_base
<222> LOCATION: (180)..(180)
<223> OTHER INFORMATION: a, c, g, t, unknown or other
<220> FEATURE:
<221> NAME/KEY: modified_base
<222> LOCATION: (183)..(183)
<223> OTHER INFORMATION: a, c, g, t, unknown or other
<220> FEATURE:
<221> NAME/KEY: modified_base
<222> LOCATION: (193)..(193)
<223> OTHER INFORMATION: a, c, g, t, unknown or other
<220> FEATURE:
<221> NAME/KEY: modified_base
<222> LOCATION: (200)..(200)
<223> OTHER INFORMATION: a, c, g, t, unknown or other

<400> SEQUENCE: 89

```
agcttgggca agctgatacc tacatttggt tccgtcactt tgaagtttag cacaaaagag     60
caaatggtaa tgattggtca gaaatgtgtt taccaggcaa ataaagccca tacaccatcc    120
tgatggtctg tactgagctt tgttgggtgg ggtgaagttt gggatgaggg ctggatggtn    180
agntgggaac tgntggtggn tggaggggag gtgttggagt gggggaggtg g             231
```

<210> SEQ ID NO 90
<211> LENGTH: 180
<212> TYPE: DNA
<213> ORGANISM: Homo sapiens

<400> SEQUENCE: 90

```
tatgagatat tgtcagggtt ggcttccctg ggctcaagct ggagaatggg actgcctacg     60
aggctcttcc tgccactgct tctactttta tatttcattc agctcccaa atctgtttta    120 gctgtaggta aggttaagtc cttctcccgt gatctggatt ttcagattcc ccagtgggga   180
```

<210> SEQ ID NO 91
<211> LENGTH: 437
<212> TYPE: DNA
<213> ORGANISM: Homo sapiens

<400> SEQUENCE: 91

```
gccctcatgg tccctgtcct gctcatgttc aacactattt tctttagaat gagattctcc      60
tgaaaatttg ttttgcattg gatcctagag ctgaggagct attttactag atcctcaaat     120
ttcctttcca ctcacaaatg gagtagagtg tacaaaatcc ctcatcatat cagtggcaga     180
tcttaaatta gtaaccacca ctttccagtg agtaccatt aggtcttatg ggttttccc       240
acctgcaagt gtacaatttg cccatttact tcagtcttct ttcttctgca cagcttctga     300
taccatgcag gtcttgcagc ttatgatgtc ggtgaacata tgcagttatt tgtcaatgag     360
ttattttgtt tgtatgttta attaccttag ttactctgtt ttggggtgga ataaggggaa     420
atcagggaga ttaaaag                                                   437
```

<210> SEQ ID NO 92
<211> LENGTH: 235
<212> TYPE: DNA
<213> ORGANISM: Homo sapiens

<400> SEQUENCE: 92

```
gccatctcct tcagctctca atcctggagc agccattcta tgctgggcct tgaagagtct      60
catcctgagc atgtgctttt ctctctgtaa acccaggatc cacaggagat ctccgtacag     120
tctcctgccc ctcattccat ccagcccttt tcactggca ccttgctcca caaattcaag      180
tcaccttagc aatctcgaac tacagtttct gcctcttcag cttcacaaaa ccaca          235
```

<210> SEQ ID NO 93
<211> LENGTH: 319
<212> TYPE: DNA
<213> ORGANISM: Homo sapiens

<400> SEQUENCE: 93

```
ttttgttctt tcactccttc ccttctgctc tgtgaagaca tagcattact cccctttgga      60
ggatgcagca ttcatagcaa catctcggaa gccaggacca gaccctcacc agacaccaaa     120
tctgccagcc tctagaactg tgaggactgt ctattggtta taagttagtt tgcggtaatc     180
tgttatagta gcacaaacac actaagacag aagttgatac cagagaagtg gcctgttgcc     240
ttaacaaata cctaaatata tagaagtggt ttcggcacta ggtaatggat agaggctgga     300
agagttttga tatgaatac                                                 319
```

<210> SEQ ID NO 94
<211> LENGTH: 202
<212> TYPE: DNA
<213> ORGANISM: Homo sapiens

<400> SEQUENCE: 94

```
agctttctgt ggtcctggtc acttcacttg ggctaagggg ccaattaact tactgagcca      60
tcccatgcca atggggaagg gctggaggaa accccaccac catcccacac atagtctgga     120
cagccctcac tcctacccca ggagcacaga tccacatcca gagcaaatgc catctcatcc     180
tggacatctt ccttgatttt gc                                              202
```

<210> SEQ ID NO 95
<211> LENGTH: 426

```
<212> TYPE: DNA
<213> ORGANISM: Homo sapiens
<220> FEATURE:
<221> NAME/KEY: modified_base
<222> LOCATION: (409)..(409)
<223> OTHER INFORMATION: a, c, g, t, unknown or other

<400> SEQUENCE: 95
ccattaaaca ctaactccat tccctcctcc catcttacct ctggcaacca ccactgtact    60
ttctgtttct atggttttga ttattctaag tacctcatat aagtggaatc atgcactatt   120 tgtcttttt tgttgttggc agatttcact tagcatactg tcctcaagtt tcatccatgt    180
gtcagaattt ccttcctttt tgcagctgaa taatatttta ttatatgtgt gtaccacatt   240
ttgtttatcc attcattcat cagtggacac ttgggttgct cctacttgtt agctattatg   300
aatgatagag tttgggtgtg tgtccccacc caaatctcat atggaaatgt aatcttcaat   360
attggaagtg gggcttggtg ggaggtgatt ggatcatggg ggtggattnt tcagggccga   420
tttatc                                                             426

<210> SEQ ID NO 96
<211> LENGTH: 185
<212> TYPE: DNA
<213> ORGANISM: Homo sapiens

<400> SEQUENCE: 96
agcttcgagc tctaaaatgt tcatctgttt agcaactgct ggataaacat ctggtatgag    60
gtcaattctc tgtaagtatg tcactcctgt gccacatgat gtgttgatga tttaatgcaa   120
gcttgtttca cccgcggccc aacacagatt cataagcttt cttaaaacag tatgagttcc   180
tttgc                                                              185

<210> SEQ ID NO 97
<211> LENGTH: 311
<212> TYPE: DNA
<213> ORGANISM: Homo sapiens

<400> SEQUENCE: 97
ataatatgac atctattttt aaaacatcac cctgtaatgg actacagagg gaaagagcaa    60
aaacagggag acatctgcaa taatctaggt tagagatgag acggtggcta aggaattttg   120
gccatacttg gaaggtaaag ctgacaagat ttgctgaaag atttgatttg ggctattctc   180
caagagagta gtcaaggatg accctgagaa tgggtcatcc atccatggag ttgctgttca   240
ttggtgcagg gaagaaaata gaagaaactt gtgagaaggt ggtagaaggt aggagtttca   300
tgttggacat g                                                       311

<210> SEQ ID NO 98
<211> LENGTH: 267
<212> TYPE: DNA
<213> ORGANISM: Homo sapiens

<400> SEQUENCE: 98
gtctcatctg aaggcttgac taggggagga ttcatttcca ggctcactta tgtagttgtt    60
ggaaggattt agtttcttgc agcctgttgg aatgaaggcc ttagttaatt tctggctgtt   120
ggttggaggc ttgtctcaat tctttgctat gtggacgtca tagggcagga tgaaacatgg   180
cagctgactt cccctgggca agtaagagag tgaaagaggt tgggctggca cagtggctca   240
tgcctgtaat cccagcactt tgggatg                                      267
```

```
<210> SEQ ID NO 99
<211> LENGTH: 230
<212> TYPE: DNA
<213> ORGANISM: Homo sapiens

<400> SEQUENCE: 99
cagtgaccgt gcaagggaaa tgttataagg tcggtcctga cagtagttag cttccttggg     60
aattcatgtt gttgttcatt atgcgagaca attactgtgt agaagagcca aacacgctca    120
gagcaaaaat aaaacttaga tcaggaaagc aaacgaaaat agcacattct gtgttgatag    180
tgtcattcgc atataccca aagagtacca tcagaaagga tgaagggatg                 230

<210> SEQ ID NO 100
<211> LENGTH: 144
<212> TYPE: DNA
<213> ORGANISM: Homo sapiens

<400> SEQUENCE: 100
ctgagagcct gtgtttgagc ttttccacca gggtaaggag cagtagatgt taggagcctc     60
gtgcttagag ccaagtgaac cagcttttc tgggaaggag agaccaaatc atccctggga    120
ggatagagcc tgtcttctgc agtg                                           144

<210> SEQ ID NO 101
<211> LENGTH: 396
<212> TYPE: DNA
<213> ORGANISM: Homo sapiens

<400> SEQUENCE: 101
tttccctgac tttgaacctt ggctctgatg tcatgtagtt agttgaggcc aaaggaaaac     60
tgatggggac tgttcatgtc tgtgtgtgag ctggagtgaa ggaaggtgtg cctaggcagg    120
gccttcggtt cctggcagtc ccctccccag cattcttgta ttttcctgcc gtgaatctac    180
tggagataga gatctggctc tgttctgctc ttcctcttct ctctgagtgg ctttgggcat    240
atccatccct tgcactggaa ctccgttacc tcctctctac agcgaggggc taactgatct    300
tgcaggcccc ttgctcctag aatagcctgt gactctgact cccagcctcc tgtttatttc    360
tgaggcttct tcccagagtg ggtaaacacc tcctct                              396

<210> SEQ ID NO 102
<211> LENGTH: 546
<212> TYPE: DNA
<213> ORGANISM: Homo sapiens

<400> SEQUENCE: 102
tatctatgac ttcctcttct gccatcagcc agtaaacaaa aactctcttc ttttaagaca     60
ttcctgagat gaggtaaggc ccaccaaaat aattttccca ccttaaggtc aactaattag    120
taagcctaat ttcatctgca gtatcccttt gctatttaat catgggtggg acatcaggtg    180
gctgagatca tgggatcacc ttaaaattct gcgtgtcaca ttgtccttcc tatgtgtgat    240
ccatgagtgc cagcccaggg gaggtagaag ggcatgttgc tgtggccagc atagctggtg    300
acttctgaga agcccgagaa ccagaaggct agaaagcgag gcatttaatg gggtcccct    360 aacggcggaa tctgtgaacc aaaaagggat gtatggtcac tatgagttcc agatagaatc    420
ccatttgggg cctgtttttt ttgttgttgt tgaaccttag aaataataag gattatttgt    480
caaagggaac taagatatta ttaagcaagg aagggcctat agaatcagaa gatatttgag    540
ttacat                                                               546
```

```
<210> SEQ ID NO 103
<211> LENGTH: 464
<212> TYPE: DNA
<213> ORGANISM: Homo sapiens

<400> SEQUENCE: 103
atctttttct ttgcagtggt ttgcaaagca ccttgcaatt tcctctcttc ttaattcctg      60
gaattctgtt tgaacttgaa ttgcttaaag ctctctgtta agcaaactat ctcttgtgtt     120
ttttcctctg atgtccacag gctttgaaac agtagctttt ccataatctt tgacaaaagt     180
ttgcactaac tccctgaagg actggtttta gtacagcctt ctcgtccatc tggctcgttc     240 tgttttttt ttttttttt cctttcctca agatcttttc tctttgttta gttttttaaa      300
ggggaatctc ttgaaagtct cctctaacat attcttactc ccctttcaa gattaagctg      360 ttatcttggt gacaggtact gacaaatacc acatagactc acaaatggtc atgtggtttg     420
gctcacagat tagtgccttt ttcaggtgat aattatcccc tggg                      464

<210> SEQ ID NO 104
<211> LENGTH: 1243
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, c, g, t, unknown or other
<220> FEATURE:
<221> NAME/KEY: modified_base
<222> LOCATION: (37)..(37)
<223> OTHER INFORMATION: a, c, g, t, unknown or other

<400> SEQUENCE: 104
naagtaacga ctgccagctg aatcttttga gtgaatnctg cccgggttca ctggtctttg      60
gggtttaaac actcccttcc ctggctccat gtactccatt ctctctagga ccggtggata    120
agttcttatc acacgacagg ggcgagcaag attgcaaccg gatggcacat agggaatga     180 ctaggataag cgcgaccaaa aaggagaaaa accatagctg tagacattct gaccgaaccc    240
gctaaagagc cgcataacgc ccccgaacct cggccccatc ccgcgcagaa agccacaagg    300
ggactattcc cgttttttt ttttgggaaa ccggatcatc cggcccgcag acagaagcga     360
cgcgaacgca ccagaacgca gagggaccca ggagcaaccc gacagacaac ggccatagcg    420 accccacac gagaccacgg aagcgcaacc agccgcacca gaacagaggg aaacaagcag     480
cacaccagga acacaacgga caggcccggc gcccgcaaa acgacaggaa caaggaagcc     540
accgacaaca accgcacaag gacaggaacg aggaacaccc ggacacccgg agcaaggcca    600
caaaacgacg cacgcaacca aagagaacac caaaaaccca gacaaaggac cgaaagccag    660
cgaagagagg gacagagcca cggcccaaac cacgccacac gaacgaccaa cagaaaggaa    720
cgcaagcagc gaccacccac cgcgcaacca caaaagcccg gggccggagc aagaaaaaca    780
caaccgaaga caccagaac gaccgacagg ccagcaacaa cgaaaggaag gcggacaaga    840 gccccccga aggagcagac acaaacccaa acgccaagga gaaaccccac caaaaggcg     900 accaacgaaa caacacgaaa agcccacaa aaaacaacc cccacgggc aacaaaacag     960 aaaaaaaccg cgaaaaaaaa aaacggaaac aaccccacaa cacccaagac aaaaagaaca    1020
ccaaagggac caccaaaccc cgaacaaaca cgaaggagaa aagaaaaac acaggccaaa    1080 caccaaagaa acacagggaa gacgaaaaca aaacccaac gaccaaacac aagaaaaaca    1140
ggccgaagaa caacagaaga gaaacgcac agaggggaac aaacacagca ccgcccaaag    1200
agaaacagca cacacgccaa acaaaacaag ggcaggcaac gaa                      1243
```

<210> SEQ ID NO 105
<211> LENGTH: 179
<212> TYPE: DNA
<213> ORGANISM: Homo sapiens

<400> SEQUENCE: 105
cacatgtatt caaggctctg taaaggatgg aagacttgtc aatcatctct gtgtttgcat    60
tcacagtgtg tgacaaacaa ctggaactga gtaaatattt gttggatgaa taagtgaaca   120
catgaatgtg tggtttacag tatgctcagt atcctactgg caccaaatat aacctttttg   179

<210> SEQ ID NO 106
<211> LENGTH: 237
<212> TYPE: DNA
<213> ORGANISM: Homo sapiens

<400> SEQUENCE: 106
gtcaccaggt gttcctcact ctcagcactg cctgctgagt gcacgagaac ccactggcct    60
gtccatcacc ctgtttctcc cagtcctcct tccctcctca aaagaaggtt ttttctgtt   120 cagtaccatt cttttttaatt tttctaacgc gattttgtca aggagctttg gttctagaat   180
ttagatttca ttacaaaaac aggcttaagt gaaaccacgg aaagctcaat gtcccag      237

<210> SEQ ID NO 107
<211> LENGTH: 327
<212> TYPE: DNA
<213> ORGANISM: Homo sapiens

<400> SEQUENCE: 107
atgcttaaca gtctggaagc aagcattggt tacaattgtt tagtggctca ttgatttcag    60
cagggtatgg actgcttctg tcctttctct cttctaccct tatgggaaca agatggtggc   120
cacagttcca agcaccaact cgtcacatga gacaccatga gcagaagtag cagggggtca   180
aaggtcactt cccttcacat ctctctttga tcagaaggaa tatctttccc aagcagaatt   240
ccttcatgtt tcattggcca gaatgggacc agacgccaac cttagaccaa tcactggcaa   300
aagcaattgc tttgttgatg tagatca                                       327

<210> SEQ ID NO 108
<211> LENGTH: 599
<212> TYPE: DNA
<213> ORGANISM: Homo sapiens

<400> SEQUENCE: 108
actttttaat ctgacatgtt ggtaagttcc taagtgcttt tatcaaaaga actacttttt    60
aatcgttcta ctctagtgtc aatgttttaa aacaggaacc acatctcact cagagtcgca   120
cctcctgctt agatgctcca cagagtaggt atccacagga acatttgtt cagttaattg    180 tatgccaagt acagcctata aaattgagag tataggccag gcatggtggc tcacgcctgt   240
aatcctagct ctttgggagg ctgaggcagg tggatcacct gagcttagga gttcaagacc   300
agcctggcca acatggcgaa accctgtctc tactaaaaat aaaaaattag ccaggcgtgg   360
tggcaagtgg ctaatcctag ctctttggga ggccgaggtg gtggatcac ccgagcttag   420 gagttcaaga ccagcctggc caacatggca aaatcccgtc tctactaaaa ataaaaaatt   480
agccagtcat cgtggcaggc gcctgtaatc ccagctactc gggaggctga ggcaggagaa   540
ttgcttgaac ccaggaggca ggcattgaag tgagctgaga tcgtgccact gcactgcag   599

<210> SEQ ID NO 109
<211> LENGTH: 594
<212> TYPE: DNA
<213> ORGANISM: Homo sapiens

<400> SEQUENCE: 109

```
ataaatcgtg ctacaatcag atgtgctgtc atccaggctt tgctgttcca tttatagagc      60
acaggcagag tcgatttacc caaatactta agggccctag aattttcaga atggtaagtg     120
agcgctggct tcaacattaa gtcaccagca gcattaaccc ctaacaagag agtcagcctt     180
tcccttgaag ttttgaaaca ttgacttctc cactatagct atgaaaatct tagatggtat     240
cttcttccaa caggaggcta tttcgtctac attgaaaatc ttgtttagtg tagccaccct     300
catcaatgat cttaattaaa tcttctggat aacctgctgc agcttcttca ttagcacttg     360
ctgtttctcc ttgcatcttt atgttataaa gacatcttgg cgtgattgag tgaaaatggc     420
agataggaag caagactagt ttgtagcttc cacttagaca gacagagcag catgtggaga     480
ctcacattgt gaactttggc tcccagaact actgcaggaa catatcagga aagtcaagag     540
aatccacaga cccttgtgaaa gaactaggtc actgtgcagc atccctgaga tgcc           594
```

<210> SEQ ID NO 110
<211> LENGTH: 348
<212> TYPE: DNA
<213> ORGANISM: Homo sapiens

<400> SEQUENCE: 110

```
tacctttctc tctggctgcc cttaacgttt tttccttcat ttcaactttg gtgaatctga      60
gaatgatgtg tcttggagtt gctcttctcg aggagtatct ttgtggcgtt ctgtgtattt     120
cctgaatctg aacgttggcc tgccttgtta gattggggaa gttctcctgg gtaatatcct     180
gcagagtgtt ttccaacttg attccattct ccccgtcact ttcaggtaca ccaatccgac     240
gtagatttgg tcttttcaca tagtcccata ttcttggag gctttgccca tttcttttta     300
ttctttttt ctctaaactt cccttctctc ttcatttcat tcatttcc                   348
```

<210> SEQ ID NO 111
<211> LENGTH: 170
<212> TYPE: DNA
<213> ORGANISM: Homo sapiens

<400> SEQUENCE: 111

```
aatgtttatc tgtttagcaa ctgctggata aacatctgga ttgaggtcaa ttctctgtaa      60
gtatgtcact cctgtgccac atgatgtgtt gatgatttaa tgcaagcttg tttcacccgc     120
ggcccaacac agattcataa gctttcttaa aacagtatga gttcctttgc                 170
```

<210> SEQ ID NO 112
<211> LENGTH: 274
<212> TYPE: DNA
<213> ORGANISM: Homo sapiens

<400> SEQUENCE: 112

```
agtaagcaac agagatccaa tggaaaaata tcttatgagt acacagaaag agattggttt      60
gatcaggaac acagaaaatc ccaaagagcc tatgtaaaaa caagaaagaa tgcagttggc     120
taccactaga tggagcccgt atttaatgcc ttaatccaca tgtattatgg gtgagccaaa     180
taaaaaagat ggcaatccct ttgttatcac aggatacagc cacatgtcag gatgaacagg     240
caggtactat tgcaattatg aaagcagaaa aaag                                  274
```

<210> SEQ ID NO 113
<211> LENGTH: 327
<212> TYPE: DNA
<213> ORGANISM: Homo sapiens
<220> FEATURE:
<221> NAME/KEY: modified_base
<222> LOCATION: (172)..(172)
<223> OTHER INFORMATION: a, c, g, t, unknown or other
<220> FEATURE:
<221> NAME/KEY: modified_base
<222> LOCATION: (176)..(176)
<223> OTHER INFORMATION: a, c, g, t, unknown or other
<220> FEATURE:
<221> NAME/KEY: modified_base
<222> LOCATION: (182)..(182)
<223> OTHER INFORMATION: a, c, g, t, unknown or other
<220> FEATURE:
<221> NAME/KEY: modified_base
<222> LOCATION: (189)..(189)
<223> OTHER INFORMATION: a, c, g, t, unknown or other

<400> SEQUENCE: 113

| | | | | | |
|---|---|---|---|---|---|
| tacccttcta | taagaggtta | tataatatga | gacttgagaa | agggcaggat | ttatataggc | 60 |
| agaaagaggg | cactgcaagg | gatcatgggt | aggaatttga | atgcaagtga | tagcttcaga | 120 |
| gttgtgacgt | gtgtggatgt | gggtgtgtgg | gttatgagga | tgaggaaagg | cngacnaggc | 180 |
| cntctgccng | agcatcagag | tagcagccaa | tggcatttct | agggtctctt | ggaggaagga | 240 |
| gctggcatct | gagctacctc | gggctccagc | tcagctaagg | caggaagctg | caattctgag | 300 |
| ggggtcatt | gaaaggagcc | cgcgcga | | | | 327 |

<210> SEQ ID NO 114
<211> LENGTH: 206
<212> TYPE: DNA
<213> ORGANISM: Homo sapiens

<400> SEQUENCE: 114

| | | | | | |
|---|---|---|---|---|---|
| atgctttatc | cagttgcagt | gccttcaata | agatttttat | tccttttaga | cacacatatc | 60 |
| actaaagggc | agttgtactt | cccatattct | ctagcctttg | ttattatttt | ttcttaaaat | 120 |
| ttgcacctgg | gaattaaagg | ctaggagtcc | ttggcttaag | tctgctgcac | agaaggaatc | 180 |
| tttaaaaat | gtaagtgatc | tattag | | | | 206 |

<210> SEQ ID NO 115
<211> LENGTH: 139
<212> TYPE: DNA
<213> ORGANISM: Homo sapiens

<400> SEQUENCE: 115

| | | | | | |
|---|---|---|---|---|---|
| cccaaccaag | acatgccatt | cccagataac | ctcctctcca | ccagagagat | gtcagcccca | 60 |
| agataacctt | ccttctgacc | agagacattc | caaccctgca | ataaacttct | cctccacaca | 120 |
| gaaactttcc | aagcctgtg | | | | | 139 |

<210> SEQ ID NO 116
<211> LENGTH: 236
<212> TYPE: DNA
<213> ORGANISM: Homo sapiens

<400> SEQUENCE: 116

| | | | | | |
|---|---|---|---|---|---|
| actcttggct | gctctgcaag | actgagcccc | atgaaggagc | cacgtgcggc | gtggaaagag | 60 |
| tgctgagttc | aaattgtagc | cctgccacta | atttgctggg | ccagtcactt | aatcatctga | 120 |
| agtcacaagt | acctcatcag | aaaagtggtc | ccagctcttc | ctgctgtgga | aggatcagaa | 180 |
| gagaggaggc | acgacagaga | cctagtgaac | tccgaagccc | gagtgctaaa | tatttg | 236 |

<210> SEQ ID NO 117
<211> LENGTH: 441
<212> TYPE: DNA
<213> ORGANISM: Homo sapiens

<400> SEQUENCE: 117

```
atcagataaa atgcaggtta agtatgagca catcatcccc caattttttc atctataggc      60
taacatccca atttatatta aggattccat tttctttctc ttcctgcccc agttgggtct     120
ttctgtggct ccagccttgc cagattgagc cgggactgtc ctgctctgct gctcctgtgc     180
tcacaggagc tgtgaactac gaaatgttca ctgttttaag ccactgagct ccgtagtaat     240
ttgttctaca ccaacagtca acacacacac actaccagac tctatctgtc gactgtttgt     300
gtcctctggg atgcaggcat tcttcctgtt ttattacaca ctgctgcagg cctaggactc     360
tacaggtctg taatggggcc tggcccaaac tagctgttga gtgacgatgg gggctaaaat     420
tatacttgcg tgtattgaaa c                                                441
```

<210> SEQ ID NO 118
<211> LENGTH: 256
<212> TYPE: DNA
<213> ORGANISM: Homo sapiens

<400> SEQUENCE: 118

```
aatgcatggg acacaccaag ggtagtggta ggcacatggt cagtgttcgg tgaaagtggc      60
tttttaccac cacgatgatt gctgctcttg ttaggcagca cacattcacc tggtggcggg     120
agcctgtagt gtcacaagga aagcaacact cagcgttcac ataaggtctc tactgcttct     180
tagctaaggg acttgggaaa tcactccttc tctctggcca cagtttaccc tcctataaag     240
tggggataat gctact                                                     256
```

<210> SEQ ID NO 119
<211> LENGTH: 110
<212> TYPE: DNA
<213> ORGANISM: Homo sapiens

<400> SEQUENCE: 119

```
aaaattctga atgtggacct gcaccttgct attttttccc ccacttggat cttctttggt      60
gtgtatgtga ctgtgtttat atgtgtctcc tatgtgtcca tcttgttttt                110
```

<210> SEQ ID NO 120
<211> LENGTH: 124
<212> TYPE: DNA
<213> ORGANISM: Homo sapiens

<400> SEQUENCE: 120

```
cccgatctct gggaaatagg gctctagcgg gagctgtgag gctctgtccc cagtcaaggt      60
cctggctaac attttcctg gcaacttagg gatacagttg ggattttgtg gactatagca     120
gtgg                                                                  124
```

<210> SEQ ID NO 121
<211> LENGTH: 103
<212> TYPE: DNA
<213> ORGANISM: Homo sapiens

<400> SEQUENCE: 121

```
cctatttttcc tacattggac tgtgctcctc catcaagaaa ctgtttctta tacttggttc      60
ataggatcta gcacaaaact aaacatgtgg ttggggctca gtt                        103
```

<210> SEQ ID NO 122
<211> LENGTH: 88
<212> TYPE: DNA
<213> ORGANISM: Homo sapiens

<400> SEQUENCE: 122

```
ctttatttta acacccaac aacagtgaat tggaaaggat ctaataacag aacagaattt      60
gtagtcagac aactttgttt tgaaacta                                       88
```

<210> SEQ ID NO 123
<211> LENGTH: 231
<212> TYPE: DNA
<213> ORGANISM: Homo sapiens

<400> SEQUENCE: 123

```
acgttgacag ttttacatgt tctaataact cggaacagat gggacaagac ctgatgtgga      60
gaagtggggg tgatataatt accctgtatt acccccctta aatccattca cttgcactca     120
tcttaatgag caatcattaa aggagacagc actaaatatt cttgaggtaa ctgacaggcg     180
gaaagagttg cttatttata ttcaaatcat ttagctcctc aaaagaaagt g             231
```

<210> SEQ ID NO 124
<211> LENGTH: 706
<212> TYPE: DNA
<213> ORGANISM: Homo sapiens

<400> SEQUENCE: 124

```
cttggtagtt cctcgcaaat tgaacacaga gttaccacat gacccaacaa ttccactcct      60
agccgtatat ccaagagaaa tgaaaacata tgtccacgca gaaactggta cacaaatgtt     120
cacagcagct ttatttgtca tggccaaaac ctggtaacaa cccaaatgtc catcaacagg     180
tattcaacag gtattgtggt ccacccatac aatgggatcc taccaacaat aaaaaaaaat     240
ggagtactga tatgcacaaa aacacctgat gaaaaagaa ttgtgctgag tgaaagaggc     300
cagcatataca ctgtatgagt ccatttctat ggaattctag aaaatgggaa ttaatctata     360
gtgacagcaa gccaagcagt ggcggtgggg atggggaca gtgaggacga attctctaga     420
tatcaagctt gaattcgttc aaagtactat aagtcctagc aagagaaatt agaaaagaaa     480
aggacataaa aggcatccaa attggaaagg aagaattttt ccagttctgt gaagaaagtc     540
attggtagct tgatggggat ggcactgaat ctataaatta ccttgggcag tatggccatt     600
ttcacaatat tgattcttcc tacccatgag catggaatgt ttttccattt gtttgtatcc     660
tcttttattt cattgagcag tggtttgtag ttctccttga agaaga                   706
```

<210> SEQ ID NO 125
<211> LENGTH: 198
<212> TYPE: DNA
<213> ORGANISM: Homo sapiens

<400> SEQUENCE: 125

```
aatgattctg tctagtttct atttgaagat atttccttttt ctactgttgg catcaaatcg      60
cttgaaatct ccacttgcaa attccacaaa aagagtgttt caaatctgct ctgtgcaaag     120
ggacgttcca ctctgtgagt tgaatacaca cagcacaaag aagttactga gaattcttct     180
gtctagcatg aaatgaag                                                  198
```

<210> SEQ ID NO 126
<211> LENGTH: 265

```
<212> TYPE: DNA
<213> ORGANISM: Homo sapiens

<400> SEQUENCE: 126
agctttatag tcactatatt agtggattgc cctctgtgga tctgatagca attttttaaa      60
tgattcacgt ttcaacttgt taaacctttc ccattcctca ggccaggttt accccacgat     120
ggacttaaaa ataagcttgt cttgctacca ggaagatttt ccaccaggag cctgcataat     180
tggcccttcc cattccaaga tgcagaaggt agaataggaa acaaaagtgc tggtcctttc     240
tctcaagtac cagccaggac tataa                                           265

<210> SEQ ID NO 127
<211> LENGTH: 345
<212> TYPE: DNA
<213> ORGANISM: Homo sapiens

<400> SEQUENCE: 127
agcctctgtc tgctctgaag gaccccaga gtgaatagct ttttccaagt gtctcagtac       60
acacagggtc attcataaaa aaccaaggtc aacaaacact atccgagcat gtggaaccct     120
gtggtttcat gctctaagca cctcacatta tatacaggag aaaacggagg cttcatctcc     180
tgtaggccct gtctacacta gggcaggtgg gatggtcata gttccaggtg cccacagagg     240
tgggctgcag gaccccagtt ctgtcctttc aaggctgtgc tgggcaaggc cctggcccag     300
gcagaaccct gggaagcttg cggattctcc tgcccatcct ctagg                     345

<210> SEQ ID NO 128
<211> LENGTH: 307
<212> TYPE: DNA
<213> ORGANISM: Homo sapiens

<400> SEQUENCE: 128
caatgatgaa atcacctgat aatgcatttc tcagaacata gccccatcct tgagtgacgc      60
atgactgtat aaaaatacac aggtttcctt gtttctttgg gtcttcattt ctgaaggctc     120
ccatgccatg taaaatttac attaagtaaa tctgtatggt tttctcttgt tagtctgtgt     180 ttttttttata gaagcctcag tcataaacct agcgatgggt gaaaagatat attttttta     240 atcccctaca gaacccacaa aggcttctga gaaagggcag gtgtaccagg gcagaaaaac     300
aggagtg                                                               307

<210> SEQ ID NO 129
<211> LENGTH: 509
<212> TYPE: DNA
<213> ORGANISM: Homo sapiens

<400> SEQUENCE: 129
acaggtattt gttatccaga gtttatacat tatgcatggt tcattttcaa agaaatgtgg      60
aagagaaggg aacatgtgtg tcctccttag ataagtgaga atattcattc aaaatgagag     120
aattaaaata tgtgataatc tctcagcata tggggcagac aggtgtatat ggaccctgga     180
tgtgcattac ccaggcaagt aagttgtact tttgtaccca ggcaagtcaa gagtttaggc     240
atctcttcct tgccatcagt aataaggccc actggaccca tgggttgacg agggaaatgt     300
cagcagttgc aatacacgag ttcagttttt aaccctatga tgatagtaag atagttttt      360 cccctcatc tctgtctaat aattccacta tctggagtat ctgtgagcct ctttctgttt     420
tctatttttc ctgcttactt tcgctcttat tttatttctt gttatgcctg gttatctttg     480
attggttgtg agaaactgtc ctcgaaaaa                                       509
```

<210> SEQ ID NO 130
<211> LENGTH: 207
<212> TYPE: DNA
<213> ORGANISM: Homo sapiens

<400> SEQUENCE: 130
cccaattgtg gccgggcgca gtggctcatg cctgtaatcc cagcactttc agaggccgag    60
gctggcagat cacaaggtca agagatcaag accatcccgc caacatggtg aaaccccatc   120
tctactaaaa atacaaaaaa tttagccggg tgtgatggcg ggcgcctgta gtcctagcta   180
ctcaggaggc tgaggccaga gaatgga                                      207

<210> SEQ ID NO 131
<211> LENGTH: 404
<212> TYPE: DNA
<213> ORGANISM: Homo sapiens

<400> SEQUENCE: 131
cggagttgaa cttttctttt gaaagagaag ttttgaaaca ccctttttgt agaatctgca    60
aatgggtatg tagcctgctt tgaggccttc attggaaacg gaatatctt cacataaaac    120 tagacagaag cattctcaga aacttcgttg tgatgtgtgc attcaactcc cagagttgaa   180
cctctctttt gatagagcag ttctgaaaca atcttttgt ggtatccgga agtggacgtt    240
tggagcgatt cgaggcctat ggtgaaaaag gcaatatctt cacctaaaaa ctagacagaa   300
gcatcctcag aaactgcttt gtgatatgtg tagtcaactc acggagttga aactttgttt   360
tgatgcagca gttttgagac actcttttgt tagaatcttc aaga                   404

<210> SEQ ID NO 132
<211> LENGTH: 440
<212> TYPE: DNA
<213> ORGANISM: Homo sapiens

<400> SEQUENCE: 132
gctgaggaca ggaggtcccc ggggaggcag gagggaagcc tgggaaacct gggcagggta    60
gaggtcgcag cagagcagga gtgccgcaga tatggccagg ctgggccctg caaggcggga   120
aagaggctgg gctggtctgt ggggacacca gccatcagac tcggccagtg agcaccctct   180
gtcttccctc caggcgtcct tctggacatc cagcagcact ttggggacga attctctaga   240
tatcaagctt gaattcgttc ctcccaccat gattctgagg cctccccagc catgtggaac   300
tataagtcca attaaacctc tttttctctc cagtctcagt atgtcttcat cagccagcat   360
gaaaacagac taatacaagt agtaaacctg aacagaacaa caccaagtaa caagactgaa   420
tcaattttaa taaaaagtct                                              440

<210> SEQ ID NO 133
<211> LENGTH: 500
<212> TYPE: DNA
<213> ORGANISM: Homo sapiens

<400> SEQUENCE: 133
aacaataatt tcctgttaca ataaccagcc tgtgacccat tgtccatgat tatctcaaaa    60
atgtctttaa tggcccggcg tggtggctca cgtctgtaat cccagccctt ggggaggctg   120
aggcgagctg attgcttcag gacaggagtt tgagaccagc ctgggcaaca taccaagacc   180
tcatctctac aaaaaataca aaaaattag ctgggcatgg tggcacgtac gacgaattct    240
ctagatatca agcttgaatt cgttcctttc ctttgaagga gtagtttgaa aacaatgtat   300

```
ttgtagaatc tgcgaagcca tatttgggag tgctttcagg cctctggtga aaagggaaat    360
atcttcagat aaaaactagg cagaagatac ctgtgaaacg gcttttgat gtgtactttc     420 atctcagagt taaaccttc ctttgatgga gtagtttgta aacactgttt ttgtataatt     480
ggtgaagaga aattttggag                                                500
```

```
<210> SEQ ID NO 134
<211> LENGTH: 538
<212> TYPE: DNA
<213> ORGANISM: Homo sapiens

<400> SEQUENCE: 134
tgctagtttt aagaatggat gtccgaggag ttcctgggct gttgctctct gagagggctc     60
cctcaccaac atcaagtcta ggaatccccg gagcactgaa gaaacctgtg aaaacacaca    120
gataccaatc tgaggactaa cacagacacc taacccagtc cccaaaatgt ttccccatt    180 catcctatca acaacttcaa attccagaaa gttaccttaa ggaaaagat gttgtgaaag    240 caaaagcatg tcttgtcttt gttaacattt cgtgttttcc ttaccttttt caagtgtgaa    300
ataataggtg taaatgacag ctcaactaag aatgaaaact tatttactac ataaaataac    360
agtggcaatc acagtgataa gagcagctat tacaaaatat ttagtatgtg caggtgctgg    420
tcacacgtgc ttgatgaagc atagtataaa cagggagccg ttttattttt ctaacaactg    480
caaccacaca ggctctgtgg aaccccttc tttaagagaa acaagcttct gtaaggat      538
```

```
<210> SEQ ID NO 135
<211> LENGTH: 234
<212> TYPE: DNA
<213> ORGANISM: Homo sapiens

<400> SEQUENCE: 135
cacggaagag ctggcaggaa ggctggctca gaagtgattg gaatggtctg gagagagagg     60
atgagaacag gaggatgtcc cactctccat gggacagaga ggcgctgggg ctctgagagc    120
tatgtaggtg gtgaacttga tgccaggccc cagcttggag agtgtacgtg cagccagctg    180
cctcctgttg agatttcttg tgcctccttt gcaagctctg gagtctttgg gttc          234
```

```
<210> SEQ ID NO 136
<211> LENGTH: 191
<212> TYPE: DNA
<213> ORGANISM: Homo sapiens

<400> SEQUENCE: 136
caatttagtt tctgacaatg cttccatcta gttttatgt gaagattttc cttttcccca      60
caggcctcaa agccctccaa atgtccactt gcagattcta gaaaagagg gtttcagagc    120 tgctctgtca agaggaaagt tcaattcttg aagtggaaca aaaacatcac aaagcagttt    180
ctgagaatgc t                                                        191
```

```
<210> SEQ ID NO 137
<211> LENGTH: 161
<212> TYPE: DNA
<213> ORGANISM: Homo sapiens

<400> SEQUENCE: 137
tggatgggga ggagctgacg aaggcatttc ggaggaggtg acgtcttacg gggaaatttg     60
tgtgttggaa tcaaagtgag ggaagggctt tggggtggag tggccaacag gagctaaggc    120
ttggaagcca tagagaatct tatcggcact ctggctgggg a                        161
```

<210> SEQ ID NO 138
<211> LENGTH: 235
<212> TYPE: DNA
<213> ORGANISM: Homo sapiens

<400> SEQUENCE: 138

```
ggaactctgc ctcccgggtt cacaccatcc tcctgcttca gcctcctgag tagctaggac    60
tacaggcgcc caccaccgtg cccggctaat ttttgtatt tttagtagag atggggtttc   120
tctgtgttag ccaggatggt ctccatctcc tgaccttgtg atccgcccac ctcagcctcc   180
caaagtgctg ggatgacagg cgtgagccac tgcacctggc cagcctgact cattc        235
```

<210> SEQ ID NO 139
<211> LENGTH: 232
<212> TYPE: DNA
<213> ORGANISM: Homo sapiens

<400> SEQUENCE: 139

```
atctctgcct cccgggttcc accatcctcc tgcttcagcc tcctgagtag ctaggactac    60
aggcgcccac caccgtgccc ggctaatttt ttgtattttt agtagagatg gggtttctct   120
gtgttagcca ggatggtctc catctcctga ccttgtgatc cgcccacctc agcctcccaa   180
agtgctggga tgacaggcgt gagccactgc acctggccag cctgactcat tc           232
```

<210> SEQ ID NO 140
<211> LENGTH: 441
<212> TYPE: DNA
<213> ORGANISM: Homo sapiens

<400> SEQUENCE: 140

```
tacttcatta gaaccccggc aaaaccgatt atacttagag ataggttctg gccaaaaacc    60
atctttctgt atgttggtgt ggtgtaacag tcattattac tgtcgagtca ggtgtctgtg   120
caaatagtga gcaagcaagg tgctggcttt cctgactgct cctgagctct caagcctttg   180
tcttttttgtt gttgttgtgg agacggagtc tcattctgtc acccaggctg gagtgcactg   240
gcacgatctt gacttactgc aatctctgcc tcctgggttc aagtgatttt cctgcctcag   300
cctcccaagt agctgcgatt acaggtgtgc accaccatgc ctggctaatt tttgtatttt   360
tagtagagat gggggtttca ccatgttggc caggctggtc ttgaactcct gacctcaagt   420
gatccacctg cctcagcctc g                                             441
```

<210> SEQ ID NO 141
<211> LENGTH: 393
<212> TYPE: DNA
<213> ORGANISM: Homo sapiens

<400> SEQUENCE: 141

```
atttgttagc atccacagta cataagaaaa tgttggggca tcaaacatga aacttcatca    60
gttaccactg tgtttgccta caagtaaaag aaaaacctca ttatagtggc ttaagcaaag   120
agaggttgat ttgttctcat atgaagaagt ctggaagtaa gcagttgtct gcttaggttt   180
agtaactcaa agttatcatg acctttctct gtggtttcca gatagctgct tgggctctgt   240
attcacagga agaagaagaa aagggaagag attatattat aaatttcaac atgtatctcg   300
ttggcaagag ctatgtcaaa gggcacccct aattgcaagg gagaccagga aatcaagact   360
tcagctctta cagtcttgac agtagacaca aac                                393
```

<210> SEQ ID NO 142
<211> LENGTH: 234
<212> TYPE: DNA
<213> ORGANISM: Homo sapiens

<400> SEQUENCE: 142
tgggcatgaa caaccacccc acgccccag gtgttcacgc tgcccaaggt gagtgccaag    60
ctgaagttga agctgacggc cctggagggc tcaagagtgc ggcgggtcag cgtggcccac   120
ttcggcagtc gtcgagccga ggactacggg gagcaccacc tggcagtcct taccaacctg   180
ggcgacatcc aggtggtctc gctgcccctg ctcaagcccc aggtgcgcta cagc         234

<210> SEQ ID NO 143
<211> LENGTH: 169
<212> TYPE: DNA
<213> ORGANISM: Homo sapiens

<400> SEQUENCE: 143
ctgcagtggc atgatctctg ctcactacaa cctccgcctc ccgggctcaa gcaattctcc    60
tacctcagcc tcccgagtgg ctgggattat aggcatgcgc cactatgcct ggctaatctt   120
tgtatgctta gtagagatgg ggtttcatca tgtcggccag gctggtcta              169

<210> SEQ ID NO 144
<211> LENGTH: 186
<212> TYPE: DNA
<213> ORGANISM: Homo sapiens

<400> SEQUENCE: 144
tgcttgctct atgggcagac tataacacag gaagcccttt tctatgcctt gtgtctcgta    60
acctctccag caaccttata agatactcac ctgaggctta cagaggtgaa ggggtttttc   120
accttactca tcttgtaagt ggcagactga gaatttaaac tcattttga gtccaaagtc    180 tgtgct                                                              186

<210> SEQ ID NO 145
<211> LENGTH: 317
<212> TYPE: DNA
<213> ORGANISM: Homo sapiens

<400> SEQUENCE: 145
tctgctgcct tctttgaaag gttatatgtg ttgttatttt gagatatgac tataaataca    60
ttgacaattt tcctatcaag tagtatcccc tcccttgaa gtttggcaaa ctttgtaact   120
gtctcaacta aaagaaggta gtgaaaataa tgcagctaag ttttcaaagc tctgctggaa   180
acagagcatg ttctcgctct gtttctcctt ctctctttct gtctcttctt ttcatgtctt   240
tttttctgtc actattaccc aacacctcaa caactcagtc agtagtcccc ataacaaatg   300
acaatttggt agagaga                                                  317

<210> SEQ ID NO 146
<211> LENGTH: 315
<212> TYPE: DNA
<213> ORGANISM: Homo sapiens

<400> SEQUENCE: 146 agcttttat ttctctgccc gtggctaggc tacaaattta tcaagctttt gcactctgct     60
tcctatttga atatgtgttg caactttaag tcatttcttt gcttatgtgt ttgagtgcag   120
gttgttagaa gcagccaggc cacttcttga acacttgct gcttagaggt ttcctctacc    180
agattcccta aatcatcatt ctttaggtca gacttccata gatccctagg gtgtgaacca   240

```
aatgcagcca agctctctgc taagacgtaa catacttgac ctttgctcta gttcccgata    300
agttcctcat ttcca                                                     315
```

<210> SEQ ID NO 147
<211> LENGTH: 182
<212> TYPE: DNA
<213> ORGANISM: Homo sapiens

<400> SEQUENCE: 147

```
agcactatag ttgtagcagg aatcttctta ctcatccgct tccaccccct agcagaaaat    60
agcccactaa tccaaactct aacactatgc ttaggcgcta tcaccactct gttcgcagca   120
gtctgcgccc ttacacaaaa tgacatcaaa aaaatcgtag ccttctccac ttcaagtcaa   180
ct                                                                  182
```

<210> SEQ ID NO 148
<211> LENGTH: 507
<212> TYPE: DNA
<213> ORGANISM: Homo sapiens

<400> SEQUENCE: 148

```
cagctacatc ctaaagacat tcattcctag attatttcaa acagcacaaa atggaagcaa    60
caagaagttc caagaagaga aggatttgta ataaaactaa agcacattgg aaatgatatt   120
gtaaccatcc aataagttca ttttttgccca cggcccggat agagccaatt tgtcaagaca   180
ggggaactgc aatagagaaa gagtttaatt catgcagagc catctgaatg ggaaaccagg   240
gttttattat tattcaaatc agtctcccca aaaattcaga gactagggtt tttcaaggac   300
agtttggcag gtaggggggcc agggagtgct aattggttgg atcagagatg agatcataga   360
gagtctgagg gtacatagct aggaagaggc ggctctggga tttgaactcc tcttctctga   420
gaggatgcgt catctgcctt gctcgtgcag cctcccctgc aggcttcagc agagcgggtg   480
gggccgatga ctgctgtact ggaaggg                                      507
```

<210> SEQ ID NO 149
<211> LENGTH: 466
<212> TYPE: DNA
<213> ORGANISM: Homo sapiens

<400> SEQUENCE: 149

```
aggattgtag gagttgtatg ccaggaaatg gggatgaaga ctgtgaaagg aaaataaatc    60
ttggggcccc caaattacta aactaaaggg aaaagtcaag ctgggaactg cttaaggcct   120
atctgcctcc cattctattc aaagtcaccc ctctgctcac tgagagaaat gcatatctga   180
ttgcttcctt tgcagaggct aatcagaaac tcaaaagaat gcagccattt gtctcttatc   240
tacctatggc ttagaagccc ctccccctccc tacttcacat cttcccacct ttgcttctag   300
ttgtcccgcc tttccagacc aaaccaatat tcatcttaca tatatttgat tgatgtctca   360
tatctcccta aaatgtatga aaccaaactg tgttctaacc accttgggca catgtcatca   420
gaacctcctg aggctgtatc atgggcgcac atcttcaaca ctggga                 466
```

<210> SEQ ID NO 150
<211> LENGTH: 333
<212> TYPE: DNA
<213> ORGANISM: Homo sapiens

<400> SEQUENCE: 150

```
cagcctgggt gacagagtga gactctgtct cacttaagag tgtgcccacc tttatcctaa    60
```

| | |
|---|---|
| gtgatgtgag ctaagctgct ccatgcccca gtctttctgg gataaactca gatttcactt | 120 |
| taaaaaagag acagaatggc tttttggtga gtaacgcacc aatttgctga ggaactcacc | 180 |
| tctattacag acttttgtat ccgaacagtg agatttccat aaagataaaa gactggcttt | 240 |
| tcttttcca cccccacaat gccacaggaa aggagctctt aaagcctaat gtgaaattat | 300 |
| ccagggaatc acctttcctg caggaaggaa gac | 333 |

<210> SEQ ID NO 151
<211> LENGTH: 433
<212> TYPE: DNA
<213> ORGANISM: Homo sapiens

<400> SEQUENCE: 151

| | |
|---|---|
| tcttccctcc caggcttaat catattttgg aacgggtgag gtcttttgtt gggtgggcac | 60 |
| cccctgattg cttgtctgtt tattttttaa tgtgcaacta atttgatttg aatttccttc | 120 |
| agtttccagg ccttcctagg gaaagctaag ggagagggaa tatgcttttt aaaaatcgtt | 180 |
| ttctttcttt ctttctttct tctttcttt ctttcttttt ctttcttttct ataattcctt | 240 |
| acagttctgc tataggtt ataagaactg ttctcatttg gccctcacaa agtccctgag | 300 |
| gtaggccagt gttgttttcc ccacaaggtg gcagactcgg tttggcatac aaaatacaca | 360 |
| gtacactcat ctctgtcctc ccacagttta caatcatggt aagttacact acacaagaca | 420 |
| atatggccaa gtg | 433 |

<210> SEQ ID NO 152
<211> LENGTH: 417
<212> TYPE: DNA
<213> ORGANISM: Homo sapiens

<400> SEQUENCE: 152

| | |
|---|---|
| tgccgggccc cagccaggcc tgtcccctcc cgctggcccc gggctcgcgg gtgacctctg | 60 |
| agcctcagct ccccgccacg cttggcggtg tgcccccgg aaaaatcaca cacacatttc | 120 |
| cttccaccca ggaacatgag gagccatctc cctagaacct ccagggcctc tctttgagcc | 180 |
| tcagtttacc cagatgcaca gtgagattgc tggacaaaac tttcatgaaa cccatactcc | 240 |
| gtgctgttct gcctgggagc agccagggct gaccttggtg gaaactcaag gaggggctcc | 300 |
| caagtttggg aggagggga gacagcccag ctctctcaga accctgtgg tcggggttgg | 360 |
| ggttagggag gatcagagct ggggtggga gtgggggcag gctcagccag gatttag | 417 |

<210> SEQ ID NO 153
<211> LENGTH: 563
<212> TYPE: DNA
<213> ORGANISM: Homo sapiens

<400> SEQUENCE: 153

| | |
|---|---|
| aagaaacaaa aagattcctg tatagctgta taatgagttt gtgttttaag ctaagtttta | 60 |
| ttacataaga gtcaaaattt ttttaaatta agtttatga agttaaaaag ctaccatagg | 120 |
| ctgtttatta tcggagaaag aaaaaacaat tttaataaat gtagtatagc ctaagtgtac | 180 |
| agtgtttaca aagttgacag tagggtacag taacttcctg agccatcact ttcactgcca | 240 |
| aatcactcac tgactcaccc agagcagcct ccagtcctgt gagcaccatt cattcaacaa | 300 |
| tggtacacct gtacaccact gtacaccact acaggccagg tacggtggct cacgcctgta | 360 |
| atcccagcaa tggaggctg aggtgggtgg atcacaaggt caggagatcg agaccatctt | 420 |
| ggctaacatg gtgaaacacc gtctctacta aaaatttttt taaaaaatta gccgggtgtg | 480 |

```
gtgacatgcg cctgtagtcc cagctactcg ggagtctgag acaggagaat cactaaaacc    540
tgaaaggcag aggttgcagt gag                                            563

<210> SEQ ID NO 154
<211> LENGTH: 179
<212> TYPE: DNA
<213> ORGANISM: Homo sapiens

<400> SEQUENCE: 154
tcaatttaga gtcctcctgc tcttttcttt ataatgttcc attgtcgcat gctacagtat     60
ttataataat ttgaaattat atctgtatgt tcatgtgttt gatgtctgtt ttctcaacct    120
gactgacaat tctatttgtt ttgttcacca acttacacct aatatttgga catggtctg    179

<210> SEQ ID NO 155
<211> LENGTH: 130
<212> TYPE: DNA
<213> ORGANISM: Homo sapiens

<400> SEQUENCE: 155
ggtgactgta atcctagcta cttgggaggc tgaggcagga gaatcacttg aactcgggag     60
acagagattg cagtgagcca agatcacgcc actgcactcc agcctgggca acagagcgag    120
actcggtctc                                                           130

<210> SEQ ID NO 156
<211> LENGTH: 227
<212> TYPE: DNA
<213> ORGANISM: Homo sapiens

<400> SEQUENCE: 156
cgttgggata caagtgtgag ccactgtgcc cagccttccc ctctcttttc actttattta     60
gtcctaaagg agagaggatg tcactgttgt catgagctgt atgtagacca cgccccttc    120 taggacaagg cttgagggat aaaccccag tggggagtgt gttccctgag gccctggtct    180
gtgtctttaa tcatattggg ttttactgg cagatccacg tggtaac                  227

<210> SEQ ID NO 157
<211> LENGTH: 238
<212> TYPE: DNA
<213> ORGANISM: Homo sapiens

<400> SEQUENCE: 157
ccacatcttc tgactccggt ttcatagatt tcctgtagaa tatatcataa attttagttg     60
aacaaacaca gtcttctgcc tggaattttg tctgttgtcc tggtgctcct ggcgtgctga    120
aggacttgtt agatcattgt cctatgtgtc attctgtaca acgccaagaa attattatca    180
taggaagcta aatcaaaaga aatcgtagca gtgcttcatg gtggggctgc tctggaag     238

<210> SEQ ID NO 158
<211> LENGTH: 236
<212> TYPE: DNA
<213> ORGANISM: Homo sapiens

<400> SEQUENCE: 158
atcccttaat tctttccgcc tgggattcaa ttgcgccaag aggactaatt gtgctaaagc     60
tataaaagtg tgctttgctc tcagtaacga cacaagctgg atgttgttag tgtgtcccgg    120
aaggaggtta ctcaggtgta atctgggtta ggctttaggt ggaattcatc ctcagagttg    180
gtcactccct ggtcgagcac gaggtaatat aaaatgcttc gcgttttaa catgac         236
```

<210> SEQ ID NO 159
<211> LENGTH: 136
<212> TYPE: DNA
<213> ORGANISM: Homo sapiens

<400> SEQUENCE: 159

```
agtagccatg tcctacttct ctcccaccta cagtgtcctg cagatgacag tgggagtgcc      60
acaaggatgg gtgaatggag cagcatacag ggctgataat tacaaatggc ccaacaagga     120
ggtggccacg tgtgct                                                     136
```

<210> SEQ ID NO 160
<211> LENGTH: 248
<212> TYPE: DNA
<213> ORGANISM: Homo sapiens

<400> SEQUENCE: 160

```
aagtagcttg ttatacagca gtaatgacta aaacacttat tatcactacc accaccacac      60
tggtattacc tgttaaacat aaacacagct gcacagtagt taaagtggtg aaaacagatt     120
ttactggcca agggccttgg ctcatgcctg taatcctggc actttgggag gctgagacag     180
gaggattgct tgaggccagg agtttgagac caacctgggc aacacagtga gacccttgtc     240
tctacaag                                                              248
```

<210> SEQ ID NO 161
<211> LENGTH: 186
<212> TYPE: DNA
<213> ORGANISM: Homo sapiens

<400> SEQUENCE: 161

```
cccacgcgcc cccgcaagct caggtctcca gcgaaagctg agtaactgag ccgggggaac      60
accaggagag agaacggggt gcgggaatgg agtcatactg aggacccaga gtacaagaaa     120
agagatccag agtgacagga gagagtgtga gtggtgagca gagtcacagt gaaggtctca     180
gggggc                                                                186
```

<210> SEQ ID NO 162
<211> LENGTH: 232
<212> TYPE: DNA
<213> ORGANISM: Homo sapiens

<400> SEQUENCE: 162

```
atctctgcct cccgggttcc accatcctcc tgcttcagcc tcctgagtag ctaggactac      60
aggcgcccac caccgtgccc ggctaatttt ttgtattttt agtagagatg ggtttctct     120
gtgttagcca ggatggtctc catctcctga ccttgtgatc cgcccacctc agcctcccaa     180
agtgctggga tgacaggcgt gagccactgc acctggccag cctgactcat tc             232
```

<210> SEQ ID NO 163
<211> LENGTH: 457
<212> TYPE: DNA
<213> ORGANISM: Homo sapiens

<400> SEQUENCE: 163

```
tctatgaaaa gaaagttaaa ctctgtgagt tgaacgcaca catcacaaag gagtttctga      60
gaatcattct gtctagtctt tatacgaaga tatttccttt ctaccattga cctcaaagcg     120
gctgaaatct ccacttgcaa attccacaaa aagagtgttt caagtctgct ctgtgtaaag     180
gatcgttcaa ctctgtgagt tgaatacaca caacacaagg aagttactga gaattcttct     240
```

```
gtctagcaga gatcacctga ggtcaggagt tcgagaccag cctggccaat atggtgaaac    300
cccgtctcta ctaaaaatac aaaaaagtag ccaggcatgg tggcacgcgc ctgtagtatt    360
ggctaactcg ggaggctgaa gcaggagaat cgcttgaacc cgagaagcag aggttgcagt    420
gagccgagat agtgccactg tactccagcc tggggac                             457

<210> SEQ ID NO 164
<211> LENGTH: 588
<212> TYPE: DNA
<213> ORGANISM: Homo sapiens

<400> SEQUENCE: 164
agcacagtta gcactagatt tccttccttt tctcctcctt tgatttctta aagaaaagaa     60
aatgtttatc atcattagat aattactctg tggacatatt agttttatta gcaacaatga    120
agtcttctct atattttatt gccatattga cttcttttca gaagcaaaaa tatgcttctt    180
ggatttggtt aaaatccagt catagatccc acacacgctc aaagggaagg cccacaaaa     240 ggccagggat gccagaagat gggatcatgg ggacgcccat gagcctagag tctgtctgcc    300
acaacttgag aaagctttcc tccattgaag agaataaaac tgttagccac tggttcaagt    360
agcttgctat ttcatgtata tattcttagt ccattggagt cttagtctga gctactataa    420
cagaataccc gagactgggt aatttataaa caatagacat ttcttttctc atggttctgg    480
aggctgggaa gtccaagagc aaggcgccag caggttccat tgtctggcaa gggctgatct    540
ttgcatctaa cacagtgcct tgagcactgc atcctccaga ggaaagga                 588

<210> SEQ ID NO 165
<211> LENGTH: 128
<212> TYPE: DNA
<213> ORGANISM: Homo sapiens

<400> SEQUENCE: 165
ggcagtggta tagattcttt tctgtttaat ttgtacagca ggtgcttgcg ctggtaggta     60
ccagtgcagg ttgtacccct ttctatggga acctggataa gtttccaggc aaggcttcat    120
agacagct                                                             128

<210> SEQ ID NO 166
<211> LENGTH: 316
<212> TYPE: DNA
<213> ORGANISM: Homo sapiens

<400> SEQUENCE: 166 taactttat atgcaccaaa aagttgtgtg actcacttta tagcgatatt caccttattg       60
taatggtctg gaaccaaacc cacaatatct ctgagttgct cctttatttt agaggcattt    120
aatcagcata tattgtatgc ttacagggtc agctatagcc acataattta tgaaaaacca    180
atatgcaggg ctgtgtattc agaaattatt aagaatttca agacaatgac agcagaacat    240
taaaccattt tgaggccctg tgtgaatgca taggtttcaa gaccatgaaa ccagctttgt    300
gtccttagaa ctgtgg                                                    316

<210> SEQ ID NO 167
<211> LENGTH: 402
<212> TYPE: DNA
<213> ORGANISM: Homo sapiens

<400> SEQUENCE: 167
atgcttcatc cttttcagtc agctgctaac aagaatgcat taaatccaca ctggaggatg      60
```

```
ggggattttc aagatctctt attaagtggt aagagcaaac tgcagagaaa tgtgcataat        120
aaaacagtga ctgaacttct ctctgtctct gtgtatttgt atatgattat atgagcataa        180
aggaagtatg gaatgatacg taccaggctg tcaccactgt gttcttggga tgggatggcc        240
atgagcagat aaacaatgga aaaaaaaaat cttcactgca aaatgactca tgcgaacggt        300
aacatgtata acattttaat ctcatttatt taattacagg ttaagatgta tatctctgta        360
tagctatgtg tgtgcataca tagacacaca gacacatata ct                          402

<210> SEQ ID NO 168
<211> LENGTH: 430
<212> TYPE: DNA
<213> ORGANISM: Homo sapiens

<400> SEQUENCE: 168
aaaagaggtt cctaggatga gctgcatcag aatcacctat ggtaattatt taaaaagcaa         60
actgatggcc tctatcccag atcaactaaa tccaaatttc tagtagatgg acccaggaa        120 tctgtatgtt agtggtccat gacctagttg attccttta gaaacaaagt taggagaatt        180
cacatccgtt ggcccctatg gagacaacaa aactgactcc ttgcccaacc accattatga        240
ctaagcatat aaagtcgcac cattggagag gaaaaacaaa aatctttaca accctgagat        300
aagctaaaaa tgaggaagaa gattctacct agtcttccaa atcaatgaag ccttgagccc        360
tttcctataa attgctaact ctctaatgta aacaacttca tccctgactt ttgcaacact        420
gacacctaca                                                              430

<210> SEQ ID NO 169
<211> LENGTH: 227
<212> TYPE: DNA
<213> ORGANISM: Homo sapiens

<400> SEQUENCE: 169
ctttcttggc agtggccatg ggcccagcaa aacagacctc tgaaaggcga gcagattaat         60
cattttgaag gcatgctcgc ctcaacagtt cccctgcagg atgtcggaga accggagaga        120
ggggactgct gtagttcaca aggggcacag ggaaatgcct gaagactcac aaaaacaagg        180
gggtgaacaa cagaaaaaga atgagtgctt ttaaattgta catgctg                      227

<210> SEQ ID NO 170
<211> LENGTH: 93
<212> TYPE: DNA
<213> ORGANISM: Homo sapiens

<400> SEQUENCE: 170
gagactcgct tgaaccgggg aggcggaggt tgcagtgagc cgagatcatg ccaccgcgct         60
ccagtctggc gacagagtga gactccgtct tgg                                     93

<210> SEQ ID NO 171
<211> LENGTH: 472
<212> TYPE: DNA
<213> ORGANISM: Homo sapiens

<400> SEQUENCE: 171
taattattgt tgttattaat ctctctatgc ctgatagcaa aagtgtttta tgaggaaagt         60
gtataccata ttaaaaatgt aggaggaaag cgaaggatcc gagttcagga caaactctta        120
gagtgttttt ttcttcttct tcaattatgc ctccttatgt tttcatcaga tgagaatgac        180
taggacaatt taagtaaaat tgataaggaa tatcagggaa aaatgtgtgt aggagcaagt        240
```

```
cacagatgta tctgttggtg agttaaaaat caacacgaac aatgagaact tcgtgacaaa    300
atctaccaat ctattatctt gcacaactgt tgatagtgaa ctttataata agaggtcatt    360
ccagtggtta taaagcccag tctcctcatt ctacaggaaa aacagaggta tggagaagat    420
caatgactga atttacatgt cttgtgacag gattggaact tgtagccagg ac           472
```

<210> SEQ ID NO 172
<211> LENGTH: 196
<212> TYPE: DNA
<213> ORGANISM: Homo sapiens

<400> SEQUENCE: 172

```
atgtggggc ctcatgttcc cagagagaca ctaaagcttt gctgactggt ctcctcatcc      60
tgggtcagga cgagtgtttt cttctctgtg gatagggcag gagaagttca cctttatgct    120
gccatatgtg aattctgggt taacaaggtc acctcctcct caggctgtgg ttttcaggct    180
gtttcaacag gttgga                                                    196
```

<210> SEQ ID NO 173
<211> LENGTH: 444
<212> TYPE: DNA
<213> ORGANISM: Homo sapiens

<400> SEQUENCE: 173

```
tttgcaaaca tgcattcgac aaaagtctaa tatccagaat ccaaaagaa cttagaaaaa      60 tcaacaagca aaacctaac aaccccatta aatgggcaaa ggagaggacc agacacttct    120
caaaagaaga caaacacgta gtcaacaagt atatggaaaa atattcaaca tcaccccagc    180
agcagagcgg gtgctcacgt caaccacgtt cttcctacaa atggcctagg tgcagggacc    240
gacctgacca ctagagaaag tgtcactgtg gcaagggaac ttcaccagcc aagggccaac    300
cttgccagcc ggtggcctca ggcctgctgg ttactctctt ttgcaaaggg gtcttggttc    360
ttgtgagtgg gaccattggg tcaaagggca gggaggtttc tgtggttctc attcggtcct    420
gcttctgccc tccagacaga tgga                                          444
```

<210> SEQ ID NO 174
<211> LENGTH: 175
<212> TYPE: DNA
<213> ORGANISM: Homo sapiens

<400> SEQUENCE: 174

```
aacagaatct tcaaggttga gatgaaactc catcatactt actagcaata acctctagca     60
aagttgaggt ggtctgtttt ggctaaataa aatggacata gcattgctgg gcccctgtga    120
agggctggaa gcagggaaat gtcagcagtg gcaagcgtgc cctctgggga gtagg         175
```

<210> SEQ ID NO 175
<211> LENGTH: 186
<212> TYPE: DNA
<213> ORGANISM: Homo sapiens

<400> SEQUENCE: 175

```
cccacgcgcc cccgcaagct caggtctcca gcgaaagctg agtaactgag ccgggggaac     60
accaggagag agaacgggt gcgggaatgg agtcatactg aggacccaga gtacaagaaa    120
agagatccag agtgacagga gagagtgtga gtggtgagca gagtcacagt gaaggtctca    180
gggggc                                                              186
```

```
<210> SEQ ID NO 176
<211> LENGTH: 405
<212> TYPE: DNA
<213> ORGANISM: Homo sapiens

<400> SEQUENCE: 176
caggagccct tcaggtcaca aaggaaaaat cccgctctat gaccaccatc tcatttacct      60
taaactagct actctttggg agaatgattc aactgatttt gactgttctc aggggtagac     120
ttgtgaagtt gtccagtgat gttgagaaca tatacttttc atcctatcaa aagctatttt     180
cttaagtcaa ttcaggcttc tataacaaag taccatacac tgggtggctt ataaacaaca     240
gaaacttact tctcacagtt ttggaggctg gaagtcaaag atcagggaac cagcttggtt     300
gggttctgtg agggccctct tcagggttgt aaactgtctt ctcattgtat tcacatgata     360
gaaagagggt gaggagagct ctctgggatc ccttttataa gggca                     405
```